US006184024B1

(12) United States Patent
Lai et al.

(10) Patent No.: US 6,184,024 B1
(45) Date of Patent: Feb. 6, 2001

(54) CHIMERIC AND/OR GROWTH-RESTRICTED FLAVIVIRUSES

(75) Inventors: Ching-Juh Lai; Michael Bray, both of Bethesda; Alexander G. Pletnev, Rockville; Ruhe Men, Kensington; Yi-Ming Zhang, Bethesda; Kenneth H. Eckels, Bethesda; Robert M. Chanock, Bethesda, all of MD (US)

(73) Assignee: The United States of America as represented by the Department of Health and Human Services, Washington, DC (US)

( * ) Notice: Under 35 U.S.C. 154(b), the term of this patent shall be extended for 0 days.

(21) Appl. No.: 08/250,802

(22) Filed: May 27, 1994

Related U.S. Application Data

(63) Continuation of application No. 08/173,190, filed on Dec. 23, 1900, now abandoned, which is a continuation-in-part of application No. 07/957,075, filed on Oct. 7, 1992, now abandoned, which is a continuation of application No. 07/218,852, filed on Jul. 14, 1988, now abandoned, said application No. 08/173,190, is a continuation-in-part of application No. PCT/US92/07916, filed on Sep. 18, 1992, which is a continuation-in-part of application No. 07/761,222, filed on Sep. 19, 1991, now abandoned, and a continuation-in-part of application No. 07/761,224, filed on Sep. 19, 1991, now abandoned, which is a continuation-in-part of application No. 07/610,206, filed on Nov. 8, 1990, now abandoned.

(51) Int. Cl.$^7$ .............. C12N 7/04; C07H 21/04

(52) U.S. Cl. ............. 435/235.1; 435/69.3; 435/236; 435/320.1; 435/348; 435/440; 424/93.1; 424/93.2; 424/218.1; 536/23.72

(58) Field of Search .............. 424/89, 93.1, 204.1, 424/218.1, 93.2; 435/69.7, 320.1, 69.1, 252.3, 172.1, 69.3, 236, 348, 440; 536/27, 23.72, 23.1; 530/395

(56) References Cited

U.S. PATENT DOCUMENTS 4,810,492    3/1989  Fujita ........................ 424/186.1

FOREIGN PATENT DOCUMENTS

WO 8803032   5/1988  (WO).
WO90/01946   3/1990  (WO).

OTHER PUBLICATIONS

Fujita et al., Studies in the development of Japanese encephalitis vaccine: expression of virus envelope glycoprotein V3(E) gene in yeast. Bulletin of the World Health Organization 65(3):303–308, 1987.*
Miller, M. J., Viral Taxonomy, Clin. Infect. Dis. 25: 18–20, 1997.*

Pletnev et al.; Proceeding of the National Academy of Sciences; vol. 89, Nov. 1992; Washington US; pp. 10532–10536; Construction and characterization of chimeric tick–borne encephalitis/dengue type 4 viruses.
Y. Zhang, et al.; Journal of Virology, vol. 62, No. 8, Aug. 1988; *Immunization of Mice with Dengue Structural Proteins and Nonstructural*Protein NS1 Expressed by Baculovirus Recombinant Induces Resistance to Dengue Virus Encephalitis; pp. 3027–3031.
M. Bray, et al.; Journal of Virology, vol. 63, No. 6, Jun. 1989; Mice Immunized with Recombinant Vaccinis Virus Expressing Dengue 4 Virus Structural Proteins with or without Nonstructural Protein NS1 Are Protected against Fatal Dengue Virus Encephalitis; pp. 2853–2856.
C. Lai et al.; Proceedings of the National Academy of Sciences USA, vol. 88, Jun. 1991; *Infectious RNA Transcribed from Stably Cloned Full–Length cDNA of Dengue Type 4 Virus*; pp. 5139–5143.
L. Markoff; Journal of Virology, vol. 63, No. 8, Aug. 1989; In Vitro Processing of Denque Virus Structural Proteins: Cleavage of the PreMembrane Protein; pp. 3345–3352.
H. Hori et al.; Journal of Virology, vol. 64, No. 9, Sep. 1990; *Cleavage of Dengue Virus NS1–NS2A Requires an Octapeptide Sequence at the C Terminus of NS1*; pp. 4573–4577.
H. Holzman, et al.; Journal of Virology, vol. 64, No. 10, Oct. 1990; A Single Amino Acid Substitution in Envelope Protein E of Tick–borne Encephalitis Virus Leads to Attenuation in the Mouse Model; pp. 5156–5159.
M. Bray, et al.; Virology, vol. 185, 1991; *Dengue Virus Premembrane and Membrane Proteins Elicit a Protective Immune Response*; pp. 505–508.

(List continued on next page.)

*Primary Examiner*—Donna C. Wortman
(74) *Attorney, Agent, or Firm*—Knobbe, Martens, Olson & Bear, LLP

(57) ABSTRACT

The invention includes a chimeric virus for use in a vaccine preparation having a genome comprising nucleic acid sequences encoding at least one structural protein from one flavivirus and nucleic acid sequences encoding nonstructural protein from another flavivirus. The genome preferably includes mutations within the viral genome that reduce virus virulence and in a particularly preferred embodiment these vaccines are directed to flaviviruses such as dengue virus, tick-borne encephalitis virus and Japanese encephalitis virus. The invention also includes a baculovirus having a recombinant dengue cDNA sequence which encodes: (1) dengue virus capsid protein, pre-matrix protein, envelope glycoprotein and NS1 and NS2a nonstructural proteins or (2) dengue envelope glycoprotein or (3) dengue nonstructural proteins NS1 and NS2a. The invention further includes a baculovirus having a recombinant Japanese B encephalitis virus cDNA sequence which encodes the Japanese B encephalitis virus capsid protein, pre-matrix protein, envelope glycoprotein and non-structural proteins NS1 and NS2a. The invention further includes a vaccine and a method to produce that vaccine.

52 Claims, 30 Drawing Sheets

OTHER PUBLICATIONS

M. Bray, et al.; Proceedings of the National Academy of Sciences USA, vol. 88, Nov. 1991; *Construction of Intertypic Chimeric Dengue Viruses by Substitution of Structural Protein Genes*; pp. 10342–10346.

S.B. Halstead, et al.; Science, vol. 239, Jan. 1988; *Pathogenesis of Dengue: Challenges to Molecular Biology*; pp. 476–481.

Lai, C–J. et al. "Immunization of Monkeys with Baculovirus Recombinant–expressed Dengue Envelope and NS1 Glycoproteins Induces Partial Resistance to Challenge with Homotypic Dengue Virus" Vaccines 90 (1990) Cold Spring Harbor Press, pp. 119–124.

Osatomi, Kiyoshi et al. "Complete Nucleotide Sequence of Dengue Type 3 Virus Genome RNA", Virology (1990) 176:643–647.

Hahn, Y.S. et al. "Nucleotide Sequence of Dengue 2 RNA and Comparison of the Encoded Proteins with those of Other Flaviviruses", Virology (1988) 162:167–180.

Mason, P.W. et al. "Sequence of the Dengue–1 Virus Genome in the Region Encoding the Three Structural Protein and the Major Nonstructural Proteins NS1", Virology (1987) 161:262–267.

Deubel, V. et al. "Nucleotide Sequence and Deduced Amino Acid Sequence of the Structural Proteins of Dengue Type 2 Virus, Jamaica Genotype", Virology (1986) 155: 365–377.

Irie, K. et al. "Sequence analysis of cloned dengue virus type 2 genome (New Guinea–c Strain)", Gene (1989) 75:197–211.

Mackow, E. et al. "The Nucleotide Sequence of Dengue Type 4 Virus: Analysis of Genes Coding for Nonstructural Proteins", Virology (1987) 159:217–228.

Heinz, F.X., *Adv. in Virus Res.*31: 103–168 (1986).

Henchal, E.a. et al., *Am. J. Trop. Med. Hyg.*31:548–555 (1982).

Hoke, et al., *Am. J. Trop. Med. Hyg.*43:219–226 (1990).

Castle, E. et al., *Virology*145:227–236 (1985).

Chakrabartri, S., *Mol. Cell. Biol.*5:3403–3409 (1985).

Cheng, H. L., et al., *Nature*296:410–415 (1982).

Kilpatrick, D.R. et al., *J. Biol. Chem.*262:16116–16121 (1987).

Mandl, C.W., *J. Virol.*63: 564–571 (1989).

Marchette, N.J., *Am.J. Trop. Med. Hyg.*43(2): 212–218 (1990).

Osatomi, K. et al., *Viral Genes*2:99–108 (1988).

Paterson, et al., *Cell*48:441–452 (1987).

Pletnev, et al., *Virology*174:250–263 (1990).

Puddington, L. et al., *J. Cell Biol.*102:2147–2157 (1986).

Rice, C.M., *Science*229: 726–733 (1985).

Roehrig, J.T. et al., *Virology*128: 118–126 (1983).

Roehring, J.T. et al., "Synthetic peptide vaccine strategy for inducing flavivirus immunity" In: *Vaccines 89: Modern Approaches to New Vaccines Including Prevention of AIDS.*Lerner, R.A. et al. (eds.) pp. 347–350. Cold Spring Harbor Laboratory (1989).

Stollar, V., *Virology*39: 426–438 (1969).

Sumiyoshi, H., *Virology*161: 497–510 (1987).

Sweet et al., *J. Immunol.*73: 363–373 (1954).

Wengler, et al., *Virology*147: 264–274 (1985).

Winkler, G. et al., *J. Gen. Virol.,*68:2239–2244 (1987).

Zhao et al., *J. Virol.*61: 4019–4022 (1987).

Clarke,D.H., *J. Exp. Med.*111:21–23 (1960).

Coia, G. et al., *Gen Virol.,*69:1–21 (1988).

Falgout, B. et al., *J. Virol.*63: 1852–1860 (1989).

Gruenberg, A. et al., *J. Gen Virol.*69: 1391–1398 (1988).

Kehry, M., et al., *Cell*21: 393–406 (1980).

Markoff, L.J. et al. "Antigenic analysis of the dengue virus envelope glycoprotein using synthetic peptides", pp. 161–165. In H. Ginsberg, et al. (ed.) *Vaccines 88: New chemical and genetic approaches to Vaccination.*Cold Spring Harbor Laboratory, Cold Spring Harbor, NY (1988).

McKee, K.T. et al., *Am.J.Trop.Med.Hyg.*36: 435–422 (1987).

Nowak, T. et al., *Virology*156: 127–137 (1987).

Sabin, *Am. J. Trop. Med. Hyg.*1:30–50 (1952).

Westaway, *Adv. Virus. Res.*33: 45–90 (1987).

Zhao, et al., *Virology*155:77–88 (1986).

Schlesinger, et al. *Fundamental Virology*2nd ed. Fields, et al. eds. pp. 453–476 (1991).

Togaviruses, Bunyaviruses, and Adenoviruses *Virology*Dulbeco, et al. eds. pp. 1178–1196 (1990).

Brown, et al. "Vaccines 90: Modern Approaches to new Vaccines Including Prevention of Aids." *Cold Spring Laboratory*, Cold Spring Harbor, NY.

Sabin, A.B. *Amer. J. Trop. Med. Hyg.*4:198–207 (1955).

Schlesinger, R.W. et al., *J. Immunol*77:352–264 (1956).

Langford, et al. *Mol. Cell. Biol.*6: 3191–3199 (1986).

Despres, et al. *Virus Research*16: 59–76 (1990).

Pincus, et al. *Virology*187: 290–297 (1990).

Men, et al. *J. of Virology*65(3): 1400–1407 (1991).

Yasuda, et al. *J. of Virology*64: 2788–2795 (1990).

Harrison, V. R. et al., *Infect. Immun.*18:151–156 (1977).

Falgout, B. et al., *J. Virol.*65:2467–2475 (1991).

Gentry, et al. *Am. J. Trop. Med. Hyg.*31(3): 548–555 (1982).

Chambers, et al. *Ann. Rev. Microbiol.*44: 649–688 (1990).

Monath, "Pathobiology of the Flaviviruses" (Schlesinger S., Schlesinger, M.J. (eds.) *The Togaviridae and the Flaviviridae*pp. 375–440.

Monath, T.P. "Flaviviruses" *Virology*B. Fields et al. (eds) pp. 955–1044. Raven Press (1985).

Rice, et al., *The New Biologist*1 (3): 285–296 (1989).

Bancroft, W. et al., *Pan Am. Hlth. Org. Sci. Publ.*375:173–178 (1979).

Bhamarapravati, N. et al., *Bull. WHO.*65:189–195 (1987).

* cited by examiner

Full-Length Combinatorials: 1A, 1B, 1C, 2A, 2B, and 2C

| Position - Amino Acid | Substitution | % Cleavage |
|---|---|---|
| P1 - Gly | Glu<br>Arg<br>Val<br>Trp | 28.3<br>6.4<br>4.3<br>56.0 |
| P-1 - Ala | Asp<br>Arg<br>Leu<br>Phe<br>Ser<br>Tyr | 3.0<br>1.0<br>1.4<br>0.0<br>6.0<br>0.6 |
| P-2 - Thr | Glu<br>Lys<br>Leu<br>Trp<br>Ser<br>Gln | 22.0<br>52.3<br>81.5<br>96.0<br>96.6<br>62.4 |
| P-3 - Val | Glu<br>Lys<br>Leu<br>Gly | 2.6<br>0.0<br>5.8<br>12.3 |

Cleavage ↓

P-8      P-7   P-6   P-5   P-4   P-3   P-2   P-1
Leu/Met - Val - Xaa - Ser - Xaa - Val - Xaa - Ala

*FIG. 16*

| Construct | Amino Acids / Nucleotide Sequences | Nucleotides of TBEV cDNA Insert |
|---|---|---|
| pTBE(CME)/Den4 | M A ... L N S R N<br>CAG ATC CTG GGG ATG GCC ... ... CTG AAC TCG AGG AAC<br>BglII/BamHI ... XhoI | 121-2376 |
| pTBE(ME)/Den4 | R K R S A V ... L N S R N<br>AGA AAA AGG TCT GCA GTA ... ... CTG AAC TCG AGG AAC<br>PstI ... XhoI | 415-2376 |
| pTBE(MENS1)/Den4 | R K R S A V ... M V H A G Q<br>AGA AAA AGG TCT GCA GTA ... ... ATG GTG CAT GCC GGA CAG<br>PstI ... SphI | 415-3504 |
| pTBE(E)/Den4 | S Y G S R C ... L N S R N<br>TCC TAC GGA TCT CGG TGC ... ... CTG AAC TCG AGG AAC<br>BamHI/BglII ... XhoI | 967-2376 |
| pTBE(ENS1)/Den4 | S Y G S R C ... M V H A G Q<br>TCC TAC GGA TCT CGG TGC ... ... ATG GTG CAT GCC GGA CAG<br>BamHI/BglII ... SphI | 967-3504 |
| pTBE(NS1)/Den4 | G T N S R N ... M V H A G Q<br>GGC ACG AAC TCG AGG AAT ... ... ATG GTG CAT GCC GGA CAG<br>XhoI ... SphI | 2380-3504 |
| pTBE(C)/Den4 | M A ... K R R S A V<br>CAG ATC CTG GGG ATG GCC ... ... AAA AGA AGG TCT GCA GTA<br>BglII/BamHI ... PstI | 121-417 |

| Virus | Age of Mice | Route of Inoc. | Mortality in Response to Initial Inoc. | Mortality in Response to IP Challenge with $10^3 LD_{50}$ TBE Virus on Day 21 |
|---|---|---|---|---|
| TBE(ME)/Den4 | 3 days | I.C. | 8/8 | — |
| | 6 wks. | I.C.<br>I.D.<br>I.P. | 5/5<br>0/5<br>0/5 | —<br>0/5<br>0/5 |
| Den4 | 3 days | I.C. | 1/8 | not tested |
| | 6 wks. | I.C.<br>I.D.<br>I.P. | 0/5<br>0/5<br>0/5 | 5/5<br>5/5<br>5/5 |

FIG. 21

| Virus | Plaque Size (mm) on | | Mouse Neurovirulence (IC $LD_{50}$) PFU |
|---|---|---|---|
| | $LLCMK_2$ | C6/36 Cells | |
| TBE(CME)/DEN4 | 1.3 | 7.0 | ~100 |
| TBE(ME)/DEN4 | 5.5 | 6.5 | ~10 |
| *PreM-Glc⁻ | 4.5 | 4.0 | <10 |
| *E-Glc⁻ | 0.4 | 2.5 | ~10 |
| *NS1(1)-Glc⁻ | 0.5 | 2.7 | >1000 |
| *NS1(2)-Glc⁻ | 0.3 | 2.2 | ~1 |
| *PreM/M⁻ | 1.8 | 5.5 | >1000 |
| *E | 4.0 | 6.2 | ~1 |
| DEN4 | 1.3 | 11.2 | not measurable |

*Denotes mutant derived from parental TBE(ME)/DEN4 chimera

FIG. 22

| TBE(ME) / DEN4 Mutant | Amino Acid Sequence | | Predicted Defective Phenotype |
|---|---|---|---|
| | Wildtype | Mutant | |
| PreM-Glcs⁻ | $Asn_{144}$-Gly-Thr | $Arg_{144}$-Gly-Thr | PreM glycosylation |
| E-Glc⁻ | $Asn_{434}$-Glu-Thr | $Leu_{434}$-Glu-Thr | E glycosylation |
| NS1(1)-Glc⁻ | $Asn_{903}$-Ser-Thr | $Ile_{903}$-Arg-Thr | NS1 site 1 glycosylation |
| NS1(2)-Glc⁻ | $Asn_{980}$-Gln-Thr | $Ile_{980}$-Gln-Thr | NS1 site 2 glycosylation |
| PreM/M⁻ | Arg-Arg-$Ser_{206}$ | Arg-Arg-$Val_{206}$ | PreM/M cleavage |
| E | $His_{384}$, $Leu_{387}$ | $Gly_{384}$, $Phe_{387}$ | to be evaluated |

1. The amino acid numbering system of Pletnev *et al.* (Ref. 18) was used to assign the amino acid positions in the PreM or E sequence.

2. The amino acid positions of DEN4 NS1 are the same as in Ref. 22.

SEQUENCE LISTING

<160> NUMBER OF SEQ ID NOS: 45

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
aaggctatgc cacgcaaa                                                      18

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
gccctggccg gccttcacct gtgatttgac cat                                     33

<210> SEQ ID NO 3
<211> LENGTH: 33
<212> TYPE: DNA
<213> ORGANISM: Artificial Sequence
<220> FEATURE:
<223> OTHER INFORMATION: Primer

<400> SEQUENCE: 3
gccctggccg gcctgcacct gtgatttgac cat                                     33

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
gccctggccg gccagcacct gtgatttgac cat                                     33

<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5
ttctgatgtg ccctgttcgg ccgtcacctg tga                                     33

<210> SEQ ID NO 6
<211> LENGTH: 33
<212> TYPE: DNA
<213> ORGANISM: Artifical Sequence
<220> FEATURE:
<223> OTHER INFORMATION: Primer

<400> SEQUENCE: 6
ttctgatgtg ccctgccagg ccgtcacctg tga                                     33

<210> SEQ ID NO 7
<211> LENGTH: 36

```
<212> TYPE: DNA
<213> ORGANISM: Artificial Sequence
<220> FEATURE:
<223> OTHER INFORMATION: Primer

<400> SEQUENCE: 7
caaaaggggg cccaagacta gaggttacag gagacc                              36

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
caaaaggggg cccaaaaaca gcatattgac gctggg                              36

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
caaaaggggg cccaacagag atcctgctgt ctctgc                              36

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
gagctggtac cagaacctgt tggatcaa                                       28

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
cctggcttgg gccccgcgt acagcttccg tggcgc                               36

<210> SEQ ID NO 12
<211> LENGTH: 36
<212> TYPE: DNA
<213> ORGANISM: Artificial Sequence
<220> FEATURE:
<223> OTHER INFORMATION: Primer

<400> SEQUENCE: 12
cctggcttgg gccccggagc tacaggcagc acggtt                              36

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
```

-continued

```
cctggcttgg gccccgtgg cacaagtggc ctgact                                36

<210> SEQ ID NO 14
<211> LENGTH: 38
<212> TYPE: DNA
<213> ORGANISM: Artificial Sequence
<220> FEATURE:
<223> OTHER INFORMATION: Primer

<400> SEQUENCE: 14
cctggctggg ccccttacag aactccttca ctctctga                             38

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
gcctccatgg ccatatgctc agc                                             23

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gctccggggt gtaagtccat t                                               21

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
gaccgacaag gacagttcca aatcgga                                         27

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18 cttttttggaa ccattggtga ct                                             22

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gtccggccgt cacctgtgat t                                               21

<210> SEQ ID NO 20
<211> LENGTH: 24
<212> TYPE: DNA
<213> ORGANISM: Artificial Sequence
```

```
<220> FEATURE:
<223> OTHER INFORMATION: Primer

<400> SEQUENCE: 20
tcacggtgca cacatttgga aaac                                          24

<210> SEQ ID NO 21
<211> LENGTH: 36
<212> TYPE: DNA
<213> ORGANISM: Artificial Sequence
<220> FEATURE:
<223> OTHER INFORMATION: Primer

<400> SEQUENCE: 21
ccggtttata gatctcggtg cacacatttg gaaaac                             36

<210> SEQ ID NO 22
<211> LENGTH: 37
<212> TYPE: DNA
<213> ORGANISM: Artificial Sequence
<220> FEATURE:
<223> OTHER INFORMATION: Primer

<400> SEQUENCE: 22
ctccattgtc tgcatgcacc attgagcgga caagccc                            37

<210> SEQ ID NO 23
<211> LENGTH: 43
<212> TYPE: DNA
<213> ORGANISM: Artificial Sequence
<220> FEATURE:
<223> OTHER INFORMATION: Primer

<400> SEQUENCE: 23
cttaggagaa cggatcctgg ggatggccgg gaaggccatt ctg                     43

<210> SEQ ID NO 24
<211> LENGTH: 36
<212> TYPE: DNA
<213> ORGANISM: Artificial Sequence
<220> FEATURE:
<223> OTHER INFORMATION: Primer

<400> SEQUENCE: 24
ggcaaaagaa ggtctgcagt agactggaca ggttgg                             36

<210> SEQ ID NO 25
<211> LENGTH: 52
<212> TYPE: DNA
<213> ORGANISM: Artificial Sequence
<220> FEATURE:
<223> OTHER INFORMATION: Primer

<400> SEQUENCE: 25
gaaggaagct catggacatg gtcggattcc tcgagttcag gcccaaccag gc           52

<210> SEQ ID NO 26
<211> LENGTH: 41
<212> TYPE: DNA
<213> ORGANISM: Artificial Sequence
<220> FEATURE:
<223> OTHER INFORMATION: Primer

<400> SEQUENCE: 26
cctggcctgg ttgggccgaa ctcgaggaat ccgaccatgt c                       41
```

<210> SEQ ID NO 27
<211> LENGTH: 38
<212> TYPE: DNA
<213> ORGANISM: Artificial Sequence
<220> FEATURE:
<223> OTHER INFORMATION: Primer

<400> SEQUENCE: 27
gtccagtcta ctgcagacct tcttttgcca cgtctttg                    38

<210> SEQ ID NO 28
<211> LENGTH: 36
<212> TYPE: DNA
<213> ORGANISM: Artificial Sequence
<220> FEATURE:
<223> OTHER INFORMATION: Primer

<400> SEQUENCE: 28
tacgcatcgg gatccgtagg atggggcgac cagcat                      36

<210> SEQ ID NO 29
<211> LENGTH: 36
<212> TYPE: DNA
<213> ORGANISM: Artificial Sequence
<220> FEATURE:
<223> OTHER INFORMATION: Primer

<400> SEQUENCE: 29
tcacaggtgc atgccggaca gggcacatca gaaact                      36

<210> SEQ ID NO 30
<211> LENGTH: 34
<212> TYPE: DNA
<213> ORGANISM: Artificial Sequence
<220> FEATURE:
<223> OTHER INFORMATION: Primer

<400> SEQUENCE: 30
cagcaatgtt actgcagacc ttttctccc gttc                         34

<210> SEQ ID NO 31
<211> LENGTH: 42
<212> TYPE: DNA
<213> ORGANISM: Artificial Sequence
<220> FEATURE:
<223> OTHER INFORMATION: Primer

<400> SEQUENCE: 31
gggagaaaaa ggtctgcagt aacattgctg tgcttgattc cc               42

<210> SEQ ID NO 32
<211> LENGTH: 46
<212> TYPE: DNA
<213> ORGANISM: Artificial Sequence
<220> FEATURE:
<223> OTHER INFORMATION: Primer

<400> SEQUENCE: 32
gcggcaaccc aggtgcgtgt cgatcgtggc acctgtgtga tcctgg           46

<210> SEQ ID NO 33
<211> LENGTH: 47
<212> TYPE: DNA
<213> ORGANISM: Artificial Sequence
<220> FEATURE:
<223> OTHER INFORMATION: Primer

<400> SEQUENCE: 33
gccaggatca cacaggtgcc acgatcgaca cgcacctggg ttgccgc       47

<210> SEQ ID NO 34
<211> LENGTH: 43
<212> TYPE: DNA
<213> ORGANISM: Artificial Sequence
<220> FEATURE:
<223> OTHER INFORMATION: Primer

<400> SEQUENCE: 34
gggggattac gtcgctgctc tagagactca cagtggaaga aaa       43

<210> SEQ ID NO 35
<211> LENGTH: 43
<212> TYPE: DNA
<213> ORGANISM: Artificial Sequence
<220> FEATURE:
<223> OTHER INFORMATION: Primer

<400> SEQUENCE: 35
ttttcttcca ctgtgagtct ctagagcagc gacgtaatcc ccc       43

<210> SEQ ID NO 36
<211> LENGTH: 43
<212> TYPE: DNA
<213> ORGANISM: Artificial Sequence
<220> FEATURE:
<223> OTHER INFORMATION: Primer

<400> SEQUENCE: 36
ttcaccccag aagcaaggat ccgcacattt taatagacg gac       43

<210> SEQ ID NO 37
<211> LENGTH: 43
<212> TYPE: DNA
<213> ORGANISM: Artificial Sequence
<220> FEATURE:
<223> OTHER INFORMATION: Primer

<400> SEQUENCE: 37
gtccgtctat taaaaatgtg cggatccttg cttctggggt gaa       43

<210> SEQ ID NO 38
<211> LENGTH: 40
<212> TYPE: DNA
<213> ORGANISM: Artificial Sequence
<220> FEATURE:
<223> OTHER INFORMATION: Primer

<400> SEQUENCE: 38
tggatagaga gctcaaggat ccagacttgg cagatagaga       40

<210> SEQ ID NO 39
<211> LENGTH: 40
<212> TYPE: DNA
<213> ORGANISM: Artificial Sequence
<220> FEATURE:
<223> OTHER INFORMATION: Primer

<400> SEQUENCE: 39
tctctatctg ccaagtctgg atccttgagc tctctatcca       40

<210> SEQ ID NO 40

-continued

```
<211> LENGTH: 41
<212> TYPE: DNA
<213> ORGANISM: Artificial Sequence
<220> FEATURE:
<223> OTHER INFORMATION: Primer

<400> SEQUENCE: 40
gatgggatca gcactacgcg tcttgttctt gatccttctt g        41

<210> SEQ ID NO 41
<211> LENGTH: 41
<212> TYPE: DNA
<213> ORGANISM: Artificial Sequence
<220> FEATURE:
<223> OTHER INFORMATION: Primer

<400> SEQUENCE: 41
gatgggatca gcactacgcg tcttgttctt gatccttctt g        41

<210> SEQ ID NO 42
<211> LENGTH: 51
<212> TYPE: DNA
<213> ORGANISM: Artificial Sequence
<220> FEATURE:
<223> OTHER INFORMATION: Primer

<400> SEQUENCE: 42
agagaccaga gcgatcgagg ctggggcaac gggtgtggat tttttggaaa a     51

<210> SEQ ID NO 43
<211> LENGTH: 45
<212> TYPE: DNA
<213> ORGANISM: Artificial Sequence
<220> FEATURE:
<223> OTHER INFORMATION: Primer

<400> SEQUENCE: 43
gccccagcct cgatcgctct ggtctctctt acacacttac gacgg       45

<210> SEQ ID NO 44
<211> LENGTH: 27
<212> TYPE: DNA
<213> ORGANISM: Artificial Sequence
<220> FEATURE:
<223> OTHER INFORMATION: Primer

<400> SEQUENCE: 44
gaccgacaag gacagttcca aatcgga        27

<210> SEQ ID NO 45
<211> LENGTH: 49
<212> TYPE: DNA
<213> ORGANISM: Artificial Sequence
<220> FEATURE:
<223> OTHER INFORMATION: Primer

<400> SEQUENCE: 45
cttgaactgt gaagcccaga aacagagtga ttcctccaac agctatgca      49
```

CHIMERIC AND/OR GROWTH-RESTRICTED FLAVIVIRUSES

RELATED APPLICATIONS

This application is a continuation of U.S. patent application No. 08/173,190 filed Dec. 23, 1993, now abandoned. U.S. patent application No. 08/173,190 is a continuation-in-part of U.S. patent application No. 07/957,075 filed Oct. 7, 1992, now abandoned, and also a continuation-in-part of International Application No. PCT/US92/07916 filed Sep. 18, 1992, which designated the United States of America. U.S. patent application No. 07/957,075 is a continuation of U.S. patent application No. 07/218,852 filed Jul. 14, 1988, now abandoned. International Application No. PCT/US92/07916 is a continuation-in-part of U.S. patent Application No. 07/761,222 filed Sep. 19, 1991, now abandoned, and also a continuation-in-part of U.S. patent Application No. 07/761,224 filed Sep. 19, 1991, now abandoned, which is a continuation-in-part of U.S. patent application No.07/610,206 filed Nov. 8, 1990, now abandoned. The complete disclosures of all of these related applications is incorporated herein by reference.

FIELD OF THE INVENTION

The present invention relates, in general, to recombinant viable chimeric flaviviruses, and to vaccines for dengue virus and other flaviviruses, including tick-borne encephalitis virus (TBEV). The invention further relates to cDNA sequences encoding the RNA transcripts to direct the production of recombinant dengue type 4 virus, recombinant mutant dengue type 4 virus chimeric dengue viruses, chimeric dengue viruses incorporating mutations to recombinant DNA fragments generated therefrom, and the cells transformed therewith.

This invention further relates to vaccines produced from recombinant DNA. Specifically, this invention relates to vaccines for dengue virus encephalitis from recombinant DNA. The strategy used in this invention is also applicable to the development of subunit vaccines against other important flaviviruses such as Japanese B encephalitis virus, and the tick-borne encephalitis viruses for which routine vaccines are generally not available.

BACKGROUND INFORMATION

The family Flaviviridae includes approximately 60 enveloped, positive strand RNA viruses, most of which are transmitted by an insect vector. Many members of this family cause significant public health problems in different regions of the world (Monath, T. P. (1986) In: The Togaviridae and Flaviviridae. S. Schlesinger et al., eds. pp. 375–440. Plenum Press, New York). The genome of all flaviviruses sequenced thus far has the same gene order: 5'-C-preM-E-NS1–NS2A–NS2B–NS3–NS4A–NS4B–NS5-3' in which the first three genes code for the structural proteins the capsid (C), the premembrane protein (pre M) and the envelope protein (E).

Dengue is a mosquito-borne viral disease which occurs in tropical and sub-tropical regions throughout the world. The dengue virus subgroup causes more human disease than any other member of the flavivirus family. Dengue is characterized by fever, rash, severe headache and joint pain. Its mortality rate is low. However, over the past few decades, a more severe form of dengue, characterized by hemorrhage and shock (dengue hemorrhagic fever/dengue shock syndrome; DHF/DSS) has been observed with increasing frequency in children and young adults. DHF/DSS occurs most often during dengue virus infection in individuals previously infected with another dengue virus serotype. This has led to the suggestion that immune enhancement of viral replication plays a role in the pathogenesis of the more severe form of disease (Halstead, S. B. (1988) Science 239, 476–481).

Dengue epidemics are a major public health problem in many tropical and subtropical areas where the vector mosquito species are abundant. Despite 40 years of intensive research, safe and effective vaccines for dengue virus disease are not available. The WHO has assigned dengue virus as a high priority target for accelerated research and vaccine development.

Soon after their isolation in 1944, dengue viruses were passaged repeatedly in mouse brain, resulting in the selection of mouse neurovirulent mutants (Sabin, A. B. (1952) Amer. J. Trop. Med. Hyg. 1:30–50). Interestingly, studies performed in volunteers showed that mouse brain-adapted neurovirulent mutants of three strains of type 1 or type 2 dengue virus were attenuated, but still immunogenic for humans (Sabin, A. B. (1952) Amer. J. Trop. Med. Hyg. 1:30–50; Sabin, A. B. (1955) Amer. J. Trop. Med. Hyg. 4:198–207; Sabin, A. B. (1955) Amer. J. Trop. Med. Hyg. 4:198–207; Schlesinger, R. W. et al. (1956) J. Immunol. 77:352–364; Wisseman, C. L. et al. (1963) Amer. J. Trop. Med. 12:620–623). However, the mutants were not developed further as candidate vaccine strains because of concern for mouse brain antigens in the vaccine preparations. Since that time, virus mutants that: (i) exhibited the small plaque size phenotype, and/or (ii) were temperature sensitive, and/or (iii) were adapted to cell cultures derived from an unnatural host (i.e., host range mutants), have been selected and evaluated as candidates for inclusion in a live attenuated virus vaccine (Harrison, V. R. et al. (1977) Infec. Immun. 18:151–156; Hoke, C. H. et al. (1990) Am. J. Trop. Med. Hyg. 43:219–226; Bhamarapravati, N. etal. (1987) Bull. WHO. 65:189–195). However, despite 25 years of such efforts, safe, effective dengue vaccines are still not available for general use. Inactivated whole dengue virus vaccines have been shown to be insufficiently immunogenic. Live virus vaccines attenuated by serial passage in cell culture have suffered from genetic instability under attenuation or poor immunogenicity. The present invention represents a technical breakthrough by providing chimeric dengue and flavivirus vaccines.

These four serotypes of dengue viruses (type 1 to type 4) are distinguishable by plaque reduction neutralization using serotype-specific monoclonal antibodies and by less specific tests using polyclonal sera (Bankcroft, W. M. et al. (1979) Pan Am. Hlth. Org. Sci. Publ. 375:175–178; Henchal, E. A. et al. (1982) Am. J. Trop. Med. Hyg. 31:548–555). The existence of serotypes was first discovered during early studies in human volunteers, which showed that infection with one dengue serotype induced durable homotypic immunity, whereas heterotypic immunity lasted only 3 to 5 months (Sabin, A. B. (1952) Amer. J. Trop. Med. Hyg. 1:30–50). An effective dengue vaccine that contains all four serotypes in order to induce broad immunity to dengue viruses in general would help to preclude the occurrence of DHF/DSS.

The complete nucleotide sequenece have been determined for dengue virus types 3 and 4 and several strains of type 2 virus including the mouse-neurovirulent New Guinea C, however, only the 5' portion of the type 1 virus genome has been sequenced (Mackow, E. et al. (1987) Virology 159:217–228; Zhao, B. et al. (1986) Virology 155:77–88; Osatomi, K. & Sumiyoshi, H. (1990) Virology 176:643–647;

Irie, A. et al. (1989) *Gene* 75:197–211; Mason, P. W. et al. (1987) *Virology* 161:262–267; Hahn, Y. S. et al. (1988) *Virology* 162:167–180). The results of these studies indicate that the four dengue virus serotypes share a common genome organization. The genome of the dengue type 4 Caribbean strain 814669 was found to contain 10646 nucleotides (Mackow, E. et al. (1987) *Virology* 159:217–228; Zhao, B. et al. (1986) *Virology* 155:77–88). The first 101 nucleotides at the 5' end and the last 384 at the 3' end are non-coding. The remaining sequence codes for a 3386 amino-acid polyprotein which includes the three structural proteins, namely, capsid (C), premembrane (pre-M), and envelope (E), at its N-terminus, followed by seven non-structural proteins in the order, provided above, that is consistent with all Flavivirus genomes identified thus far. The polyprotein is processed to generate 11 or more viral proteins by cell signal peptidase(s) and by viral proteases (Markoff, L. (1 989) *J. Virol,* 63:3345–3352; Falgout, B. et al. (1989) *J. Virol,* 63:1852–1860; Falgout, B. et al. (1991) *J. Virol.* 65:2467–2476; Hori, H. & Lai, C. J. (1990) *J. Virol.* 64:4573–4577).

Previously we constructed a full-length dengue virus cDNA that could serve as the template for transcription of infectious RNA. We have obtained stably cloned full-length dengue virus cDNA and in vitro RNA transcripts derived from the DNA template were shown to be infectious for cells in culture. However, this infectious construct and infectious RNA transcripts generated therefrom are pathogenic. Moreover, the attenuated dengue viruses generated thus far are genetically unstable and have the potential to revert back to a pathogenic form over time. Yet, attenuated viruses are desirable since they are generally known to provided long-lasting immunity. Therefore, modifications to this construct or to chimeric constructs that then direct the production of a less pathogenic virus would be a considerable advance to attenuated flavivirus vaccine technology. Accordingly, we have constructed a series of deletions in the 3' non-coding region of cDNA, as disclosed herein, and have recovered viable dengue virus mutants for analysis of growth characteristics.

Other members of the Flavivirus family are also pathogenic. Examples include tick-borne encephalitis virus and Japanese Encephalitis Virus. Like attenuated dengue virus vaccines, attenuated tick-borne encephalitis virus (TBEV) virus has tended to be genetically unstable and poorly immunogenic. Therefore, other attenuated flavivirus vaccines would also be a considerable advance in the art. Thus, this invention additionally employs modified full-length recombinant cDNA constructs of dengue virus or another flavivirus as a framework for gene manipulation and chimeric virus development for the production of vaccines to other Flaviviruses.

Tick-borne encephalitis virus (TBEV) is transmitted exclusively by ticks and can be divided into two serologically distinguishable subtypes: the Eastern subtype (prototype strain Sofjin), prevalent in Siberian and Far Eastern regions of Russia, and the Western subtype (prototype strain Neudorfl), common in eastern and central Europe. TBEV causes a serious encephalitic illness with a mortality rate ranging from 1 to 30%. For a review of TBEV see Calisher, et al. (*J. Gen. Virol* 70: 37–43). Currently, an experimental TBE vaccine produced by formalin inactivation of TBEV is available, but this vaccine has several limitations. For example, the vaccine is not sufficiently immunogenic, therefore repeated vaccinations are required to generate a protective immune response. Even when antibody responses to the vaccine are present, the vaccine fails to provide protective responses to the virus in 20% of the population. Therefore, there remains a need for an improved TBEV vaccine.

Dengue viruses continue to cause major epidemics throughout the tropical and subtropical regions of the world. Despite many years of research effort, an effective vaccine is not available. The predominant disease associated with dengue viral infection is a debilitating illness known as dengue fever. Less frequently, dengue virus causes a hemorrhagic shock syndrome in young children, which has a very high mortality rate. Thus, control of dengue fever and dengue hemorrhagic shock is a major global concern. Consequently, the WHO has designated the dengue viruses as one of five high priority targets for accelerated vaccine development. The industry is lacking a vaccine formed from a genetically engineered dengue protein.

SUMMARY OF THE INVENTION

In one aspect, the present invention provides a recombinant DNA construct containing nucleic acid derived from at least two flaviviruses. The construct includes a region of nucleic acid operably encoding no more than two structural proteins from tick-borne encephalitis virus (TBEV). This region is operably linked to a region of nucleic acid encoding structural proteins from a flavivirus other than TBEV. Preferably, the construct includes a region of nucleic acid operably encoding flavivirus capsid protein operably linked to the region of nucleic acid operably encoding no more than two structural proteins from tick-borne encephalitis virus. The regions of nucleic acid encoding capsid protein and non-structural proteins are preferably from dengue virus, such as dengue type 4 virus. In a preferred form, the construct contains at least one mutation in the nucleic acid derived from at least two flaviviruses. In one embodiment of this preferred form, the mutation ablates NS1 (1) protein glycosylation. In another embodiment of this form, the mutation prevents production of the mature flavivirus membrane protein. The mutation preferably affects viral growth rate. The invention also includes RNA transcripts corresponding to these recombinant DNA constructs within the present invention.

In another aspect of the present invention, there is provided a chimeric virus having a genome derived from a flavivirus. This chimeric virus include a region of nucleic acid encoding no more than two structural proteins from tick-borne encephalitis virus, and a region of nucleic acid encoding nonstructural proteins from another flavivirus. Preferably, the virus includes a region of nucleic acid encoding capsid protein from the other members of the flavivirus family. The nucleic acid from tick-borne encephalitis virus can encode any of a number of proteins, such as pre-membrane protein and/or the envelope protein. The nucleic acid encoding nonstructural proteins from another flavivirus is preferably from dengue virus, such as type 4 dengue virus. In one embodiment, the chimeric virus of this aspect of the invention contains at least one mutation in the nucleic acid. This mutation can take any of a number of forms, such as a mutation that ablates NS1(1) protein glycosylation, or one that prevents production of the mature flavivirus membrane protein. The mutation preferably affects viral growth rate.

Another aspect of the present invention provides a chimeric virus that includes a region of nucleic acid encoding the premembrane and envelope proteins of tick-borne encephalitis virus, and a region of nucleic acid encoding the capsid protein from another flavivirus, and a region of nucleic acid encoding non-structural proteins from the same flavivirus. The other flavivirus can be, for example, a dengue virus, such as dengue virus type 4. In this aspect of the invention, a preferred form of the chimeric virus includes at least one mutation in the region of nucleic acid encoding premembrane and envelope protein of tick-borne encephalitis virus. The mutation can be one that prevents production of the mature flavivirus membrane protein. In another preferred form, the chimeric virus includes at least one mutation in the regions of nucleic acid from the other flavivirus. This mutation can be one that ablates NS1(1) protein glycosylation.

In another aspect, the invention provides a vaccine for humans against tick-borne encephalitis comprising a chimeric virus of the present invention that is capable of generating a protective immune response in a vertebrate. Thus, the invention also includes a method for preparing a vaccine for humans against a flavivirus comprising preparing a DNA construct operably encoding the premembrane and envelope protein from the flavivirus and the capsid and nonstructural protein from dengue virus, generating infectious RNA transcripts from the DNA construct, introducing the RNA transcripts into a cell, expressing the RNA transcripts in the cell, harvesting the virus from the cells, testing the virus in a vertebrate, and inoculating the humans with the virus. The preparing step can include introducing mutations into the DNA construct.

A preferred aspect of the present invention provides a chimeric virus that includes region of nucleic acid encoding the premembrane and envelope proteins of Japanese encephalitis virus, and a region of nucleic acid encoding the capsid protein from another flavivirus, and a region of nucleic acid encoding non-structural proteins from the same flavivirus, such as dengue virus.

Another aspect of the present invention provides a chimeric virus having an RNA genome. This genome includes a region of nucleic acid operatively encoding non-structural protein of type 4 dengue virus and a region of nucleic acid operatively encoding structural protein of a type 1 dengue virus, type 2 dengue virus, type 3 dengue virus, yellow fever virus, Japanese encephalitis virus, tick-borne encephalitis virus, or another flavivirus. In one embodiment of the invention, the genome of the chimeric virus is substantially free from nucleic acid operatively encoding type 4 dengue virus structural protein. Preferred embodiments of the chimeric virus can include p2A(D1 WP) or p2A(D2 NGC) RNA. Preferably, the chimeric virus includes a region of nucleic acid operatively encoding non-structural protein of type 1 dengue virus, type 2 dengue virus, or type 3 dengue virus, and also includes a region of nucleic acid operatively encoding structural protein of type 1 dengue virus, type 2 dengue virus, type 3 dengue virus, type 4 dengue virus, yellow fever virus, Japanese encephalitis virus, tick-borne encephalitis virus, or another flavivirus. The nucleic acid operatively encoding non-structural protein is preferably from a different virus than the region of nucleic acid operatively encoding non-structural protein.

Another aspect of the invention provides a chimeric virus having an RNA genome. This genome includes a region of nucleic acid operatively encoding non-structural protein of yellow fever virus, Japanese encephalitis virus, tick-borne encephalitis virus or another flavivirus, and a region of nucleic acid operatively encoding structural protein of type 1 dengue virus, type 2 dengue virus, type 3 dengue virus, type 4 dengue virus, yellow fever virus, Japanese encephalitis virus, tick-borne encephalitis virus, or another flavivirus. The region of nucleic acid operatively encoding structural protein is preferably from a different virus than the region of nucleic acid operatively encoding non-structural protein.

Yet another aspect of the invention provides a vaccine, capable of generating a protective immune response to a virus in a vertebrate. This vaccine includes a safe and immunologically effective amount of any of the viruses of the present invention and a pharmaceutically and immunologically acceptable carrier.

Still another aspect of the invention provides another vaccine that is capable of generating a protective immune response to a virus in a vertebrate. In this aspect of the invention, the vaccine includes a safe and immunologically effective amount of the following viruses: a) a chimeric virus wherein the genome of the virus includes a region of nucleic acid encoding non-structural protein of type 4 dengue virus and a region of nucleic acid encoding structural protein of type 1 dengue virus, b) a chimeric virus, wherein the genome of the virus includes a region of nucleic acid encoding non-structural protein of type 4 dengue virus and a region of nucleic acid encoding structural protein of type 2 dengue virus, c) a chimeric virus, wherein the genome of the virus includes a region of nucleic acid encoding non-structural protein of type 4 dengue virus and a region of nucleic acid encoding structural protein of type 3 dengue virus, and d) an attenuated type 4 dengue virus.

A further aspect of the present invention provides a DNA segment that includes a non-structural region of type 4 dengue virus, and a structural region from one of the following viruses: type 1 dengue virus, type 2 dengue virus, type 3 dengue virus, yellow fever virus, Japanese encephalitis virus, tick-borne encephalitis virus, and another flavivirus. In a preferred embodiment of the invention, the DNA segment contains a promoter operably linked to the structural and nonstructural regions. In another preferred embodiment, the DNA segment contains a promoter which is a SP6 or T7 promoter. In yet another preferred embodiment, the DNA segment is p2A(D1 WP) or p2A(D2 NGC).

Other aspects of the invention provide other chimeric DNA segments. The DNA segments of these aspects of the invention include a non-structural region of type 1 dengue virus, type 2 dengue virus or type 3 dengue virus. These DNA segments further include a structural region from one of the following viruses: type 1 dengue virus, type 2 dengue virus, type 3 dengue virus type, 4 dengue virus, yellow fever virus, Japanese encephalitis virus, tick-borne encephalitis virus, and a flavivirus, with the proviso that the structural region and the non-structural region are not from the same virus.

A further aspect of the invention provides a DNA segment that includes a non-structural region from one of the following viruses: yellow fever virus, Japanese encephalitis virus, tick-borne encephalitis virus, and another flavivirus, and a structural region from one of the following viruses: type 1 dengue virus, type 2 dengue virus, type 4 dengue virus, yellow fever virus, Japanese encephalitis virus, tickborne encephalitis virus, and another flavivirus wherein the structural region is from a different virus than the non-structural region.

Another aspect of the invention provides a DNA segment comprising a non-structural region or a portion thereof of a flavivirus, and a structural region or a portion thereof from a different flavivirus.

Still another aspect of the invention provides a vaccine, capable of generating a protective immune response to a virus in a vertebrate. This vaccine includes a safe and immunologically effective amount of a chimeric virus. The genome of the virus includes nucleic acid operably encoding the structural proteins from a tick-borne encephalitis virus and nucleic acid operably encoding the non-structural protein from a dengue virus.

Yet another aspect of the invention provides another chimeric virus. In this aspect, the chimeric virus has a genome of the virus operably encoding tick-borne encephalitis structural protein and dengue type 4 virus non-structural protein. In a preferred embodiment, the structural proteins of the virus are derived from tick-borne encephalitis virus.

Still another aspect of the invention provides a segment of DNA operably encoding tick-borne encephalitis structural protein and dengue type 4 virus non-structural protein.

A further aspect of the invention provides an isolated DNA fragment that encodes infectious dengue type 4 viral RNA. Still another aspect of the invention provides a recombinant DNA construct comprising the DNA fragment of the present invention, and a vector. In a preferred embodiment, the vector is a plasmid. A further aspect of the invention includes a host cell stably transformed with a recombinant DNA construct according to the present invention in a manner allowing expression of the DNA fragment. In a preferred embodiment, the host cell is a prokaryotic cell.

Another aspect of the invention provides a method for producing mutants of dengue type 4 virus. This method includes the steps of (i) introducing mutations into the genome of dengue type 4 virus by site-directed mutagenesis, (ii) recovering infectious dengue type 4 viruses harboring the mutations, and (iii) evaluating recovered viruses. In one embodiment of this method, the recovered viruses are evaluated for attenuated or avirulent phenotype.

Still another aspect of the invention provides a vaccine for humans against dengue type 4 virus. This vaccine includes an avirulent dengue type 4 virus, in an amount sufficient to induce immunization against the disease, and a pharmaceutically acceptable carrier. In a preferred embodiment, the avirulent dengue type 4 virus is obtained by engineering mutations at strategic regions in the viral genome.

Yet another aspect of the present invention provides a DNA fragment that encodes chimeric flaviviral RNA. The chimeric RNA includes, for example, a member selected from the group consisting of dengue type 1, dengue type 2 and dengue type 3.

Still another aspect of the invention provides a method for construction of chimeric dengue viruses. This method includes replacing DNA fragments of the dengue type 4 virus DNA according to the method of the present invention with corresponding genes en bloc, or a fraction thereof, from a different flavivirus. In a preferred embodiment, the different flavivirus is one of the following viruses: dengue type 1, dengue type 2 and dengue type 3. In another preferred embodiment, the dengue type 4 virus contains at least one mutation.

The present invention includes another aspect which provides a vaccine for humans against dengue virus. In this aspect, the invention includes an infectious chimeric virus, in an amount sufficient to induce immunization against the disease, and a pharmaceutically acceptable carrier. The chimeric virus is derived from, for example, dengue type 1, dengue type 2, dengue type 3 or dengue type 4 virus.

Yet another aspect of the invention provides a recombinant DNA construct comprising the DNA fragment of the present invention, and a vector. In one preferred embodiment, the vector is a plasmid. Still another aspect of the present invention provides a host cell stably transformed with the recombinant DNA construct according to the method of the present invention, in a manner allowing expression of the DNA. In a preferred embodiment, the host cell is a prokaryotic cell.

Still another aspect of the invention provides a DNA fragment that encodes a dengue type 4 viral RNA, wherein the DNA fragment contains a substitution mutation in the sequence encoding one or more of eight amino acids at the C terminus of NS1 of the cleavage site of the non-structural protein NS1–NS2A.

A further aspect of the invention provides a DNA fragment that encodes a dengue type 4 viral RNA, wherein the DNA fragment contains a substitution at the site encoding glycine, which site is at position +1 following the cleavage site of the non-structural protein NS 1–NS2A.

A still further aspect of the invention provides a DNA fragment that encodes a dengue type 4 viral RNA, wherein the DNA fragment contains a deletion in the 3'-noncoding region. In a preferred embodiment, the deletion is between 30 and 202 nucleotides in length.

Another aspect of the invention provides a recombinant DNA construct including any of the DNA fragments of the present invention and a vector. Still another aspect of the invention provides an infectious RNA transcript of a DNA fragment of the present invention. A further aspect of the invention provides a host cell transfected with the DNA constructs of the present invention in a manner allowing expression of the DNA fragment. Such a host cell can be a mammalian or an insect cell.

Still another aspect of the invention provides a vaccine for humans against dengue type 4 virus. In this aspect of the invention, the vaccine includes a mutant dengue type 4 virus exhibiting reduced virulence, in an amount sufficient to induce immunization against the disease. In a preferred embodiment, the mutant dengue type 4 virus is obtained by engineering a deletion mutation in the 3'-noncoding region in the viral genome. In another preferred embodiment, the mutant dengue type 4 virus is obtained by engineering a substitution mutation in the viral DNA sequence encoding one or more of eight amino acids at the C terminus of NS1 of the cleavage site of the non-structural protein NS1–NS2A. In yet another preferred embodiment, the mutant dengue type 4 virus is obtained by engineering a substitution at the viral DNA site encoding glycine, which site is at position +1 following the cleavage site of the non-structural protein NS1–NS2A.

Still another aspect of the invention provides a method for construction of chimeric dengue viruses comprising replacing DNA fragments of the dengue type 4 virus DNA with corresponding genes en bloc, or a fraction thereof, from a different flavivirus. In a preferred embodiment, the different flavivirus is one of: dengue type 1, dengue type 2, dengue type 3, Japanese encephalitis and tick-borne encephalitis virus. In another preferred embodiment, the method for construction of chimeric dengue viruses includes replacing DNA fragments of the dengue type 4 virus DNA according to the present invention, with corresponding genes en bloc, or a fraction thereof, from a different flavivirus. Preferably, the flavivirus is selected from the group consisting of dengue type 1, dengue type 2, dengue type 3 and Japanese encephalitis. Also preferably, the method for construction of chimeric dengue viruses includes replacing DNA fragments of the dengue type 4 virus DNA according to the present invention, with corresponding genes en bloc, or a fraction thereof, from a different flavivirus. In the preferred method, the flavivirus is selected from the group consisting of dengue type 1, dengue type 2, dengue type 3, Japanese encephalitis and tick-borne encephalitis virus.

One additional aspect of the invention provides a vaccine against dengue virus that is administered in an amount sufficient to induce immunization against the disease. The vaccine includes a chimeric virus exhibiting reduced virulence, wherein the chimeric virus contains a DNA fragment that encodes a dengue type 4 viral RNA containing a deletion in the 3'-non-encoding region. In a preferred embodiment, the chimeric virus is selected from the group consisting of dengue type 2, dengue type 3 and dengue type 4 virus.

A further aspect of the invention is a baculovirus having a 4.0 kilo-base recombinant sequence dengue cDNA sequence. The sequence encodes dengue virus capsid protein, pre-matrix protein, envelope glycoprotein, and NS1 and NS2a nonstructural proteins. The invention includes a vaccine and a method to produce that vaccine.

Further aspects of the present invention will become apparent to those of ordinary skill in the art upon reference to the ensuing description of the invention.

The diagram depicts the full-length dengue cDNA clone containing the SP6 promoter sequence at the 5'-end and an Asp 718 cleavage site at the 3'-end. The Bst B1 cleavage site at nucleotide 5069 separates the dengue genome into the 5'- and 3'-fragments. Replacement of these fragments in the full-length clone 1A with the corresponding 5'-2, 3'-B, on 3'-C fragments gave rise to other full-length combinations as shown.

Figure 9:
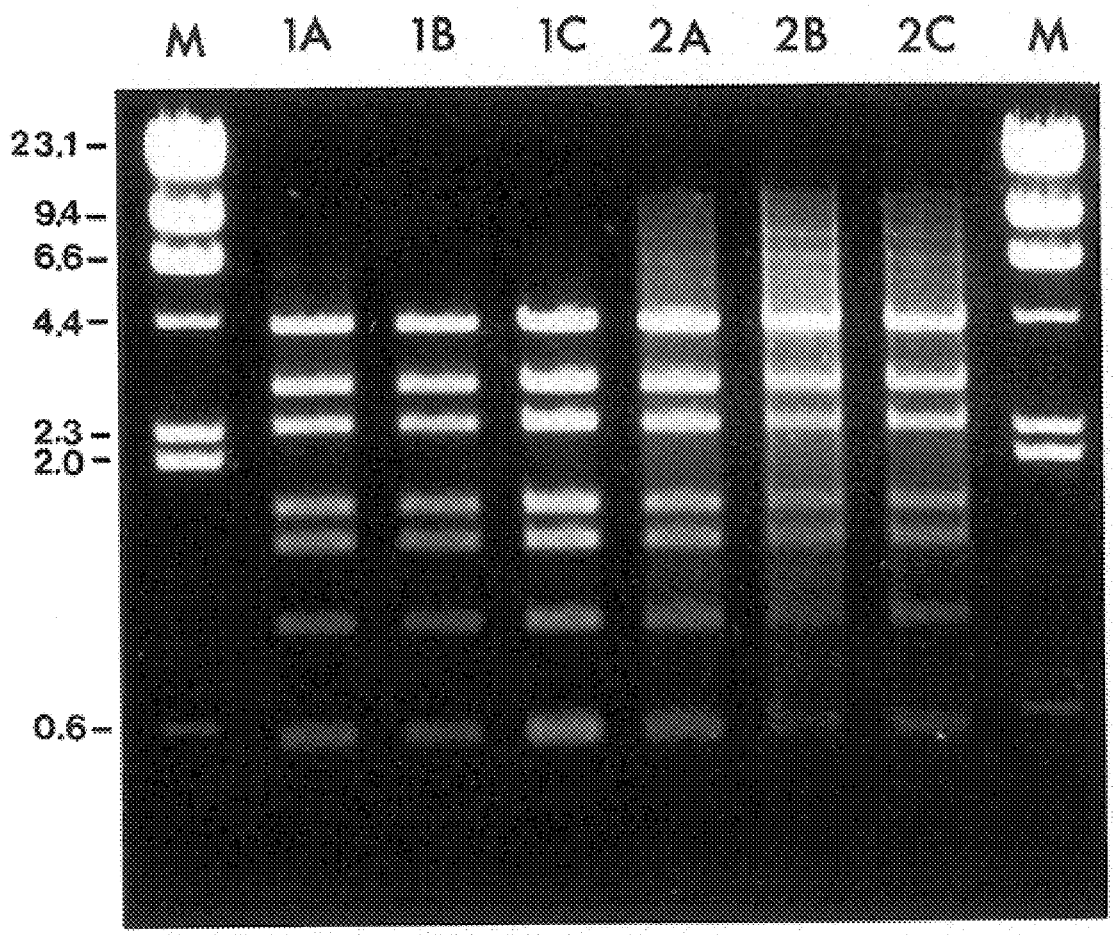

FIG. 9 provides the restriction endonuclease pattern of the full length dengue cDNA clone digested with BgI II, Nsi I, and Asp 718 and the digests were analyzed by separation on an agarose gel. M shows λ Hind III DNA fragments as molecular size markers in kilobase pairs.

Figure 10:
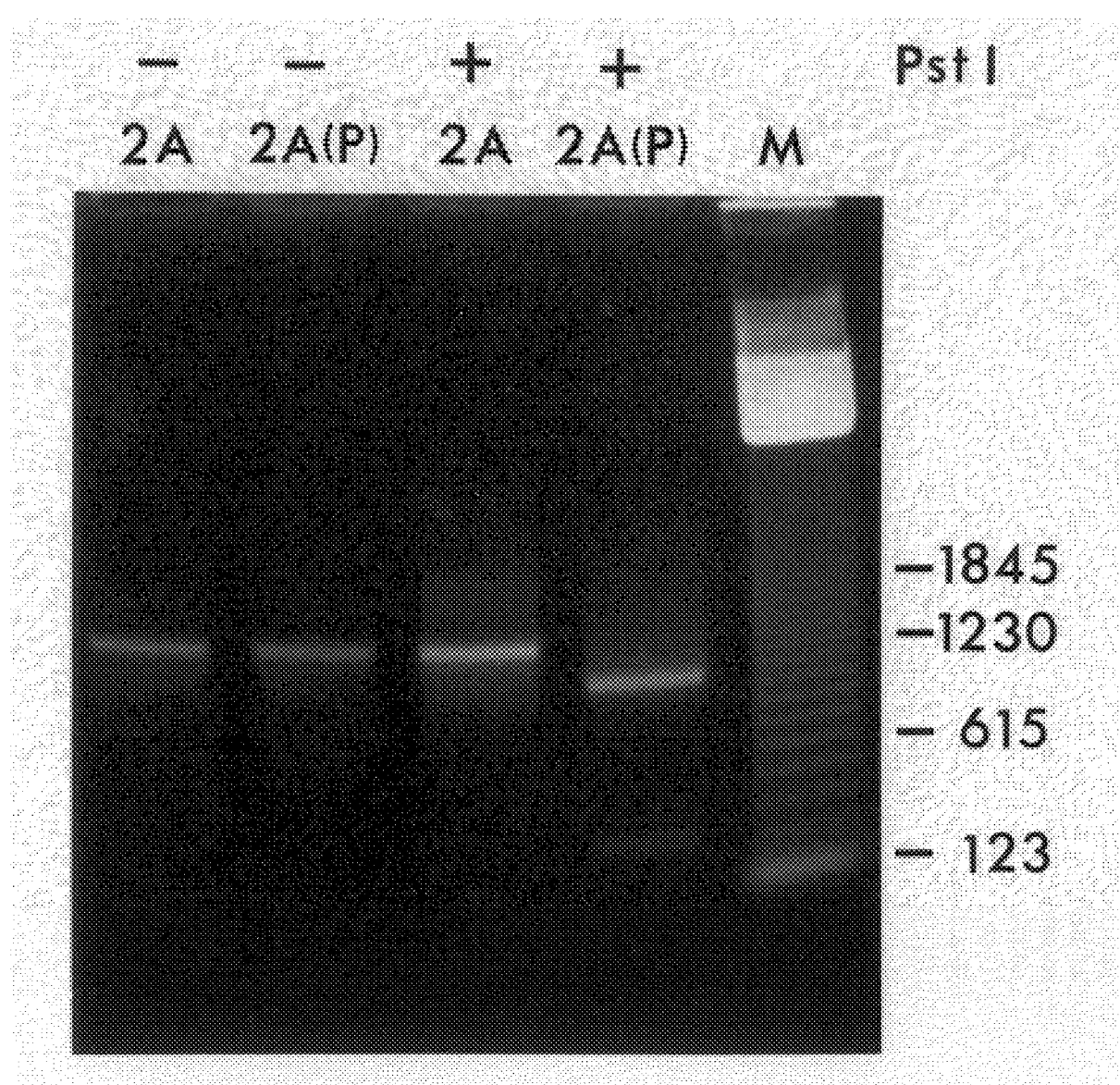

FIG. 10 provides a demonstration that dengue virus recovered from infectious RNA contains the genomic sequence of the template DNA.

Progeny dengue virus was recovered from LLC-MK$_2$, cells transfected with RNA transcribed from clone 2A DNA (wild type control), or from clone 2A (P) DNA containing a Pst I site at nucleotide 3473 of the dengue sequence. Genomic RNA extracted from the recovered virus was used for reverse transcription and the cDNA product was used as the template to produce the 1343 bp DNA fragment (nucleotides 3193–4536) by PCR using the appropriate primers. Pst I digestion of the PCR product is shown. Lane M shows the 123 DNA ladders as size markers.

Figure 11:
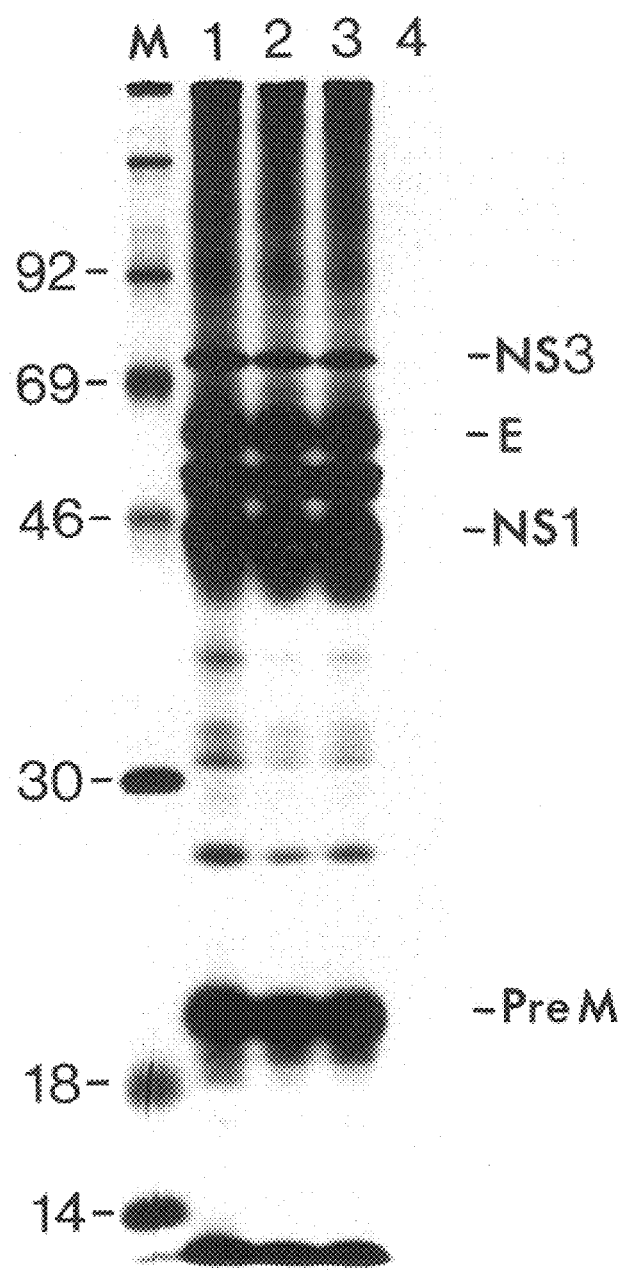

FIG. 11 provides a comparison of dengue virus proteins from recovered virus and parental virus infected cells.

$^{35}$S-methionine labelled lysates from LLC-MK$_2$, cells infected with recovered dengue virus or parental wild type were prepared for immunoprecipitation with dengue hyper-immune mouse ascetic fluid. The immunoprecipitates were separated by electrophoresis on SDS-12% polyacrylamide gel. Gel lanes shown contain lysates from cells infected with: (1) parental dengue virus; (2) dengue virus recovered from clone 2A DNA; (3) dengue virus recovered from clone 2A (P) DNA; lane 4 is from mock infected cell lysate; and lane M contains protein size markers in kilo daltons shown on the left. Labelled bands that correspond to dengue virus proteins including PreM, E, NS, and NS3 are indicated. The identities of other labelled bands have not been assigned.

Figure 12:
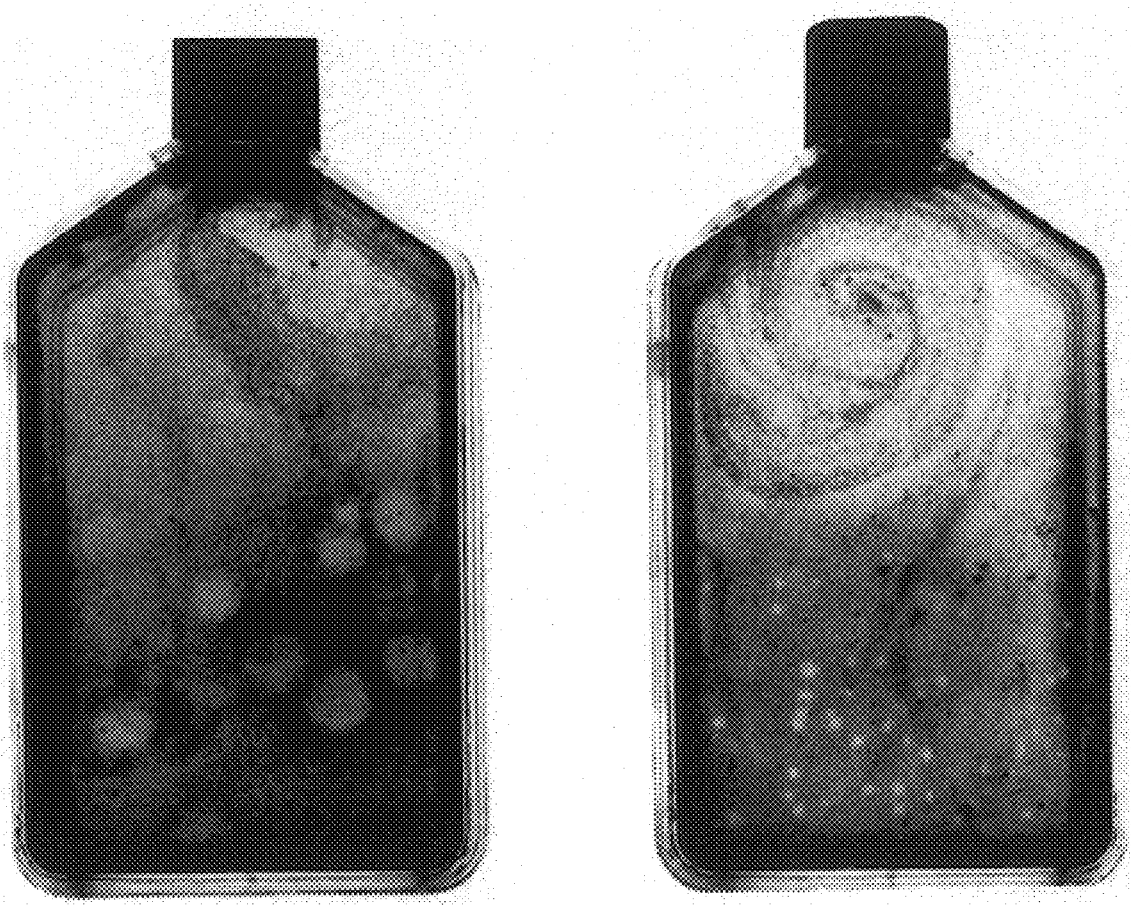

FIG. 12 provides the plaque morphology of wild-type dengue type 4 virus and its derived amino acid substitution mutant D4 ($G_{1126} \rightarrow E$)

Confluent mosquito C6/36 cells in a 76-cm$^2$ flask were infected with dengue virus and an agarose overlay was subsequently added. Six days after infection, cells were strained with neutral red. The plaque size was measured the next day. The average plaque size of wild-type dengue 4 virus and the substitution mutant was calculated from 10 individual plaques. The mutant virus shown contained Glu (E) substituting for Gly (G) at position 1126 of the dengue type 4 polypeptide sequence. This position corresponds to position +1 at the NS1–NS2A cleavage sequence.

Figure 13:
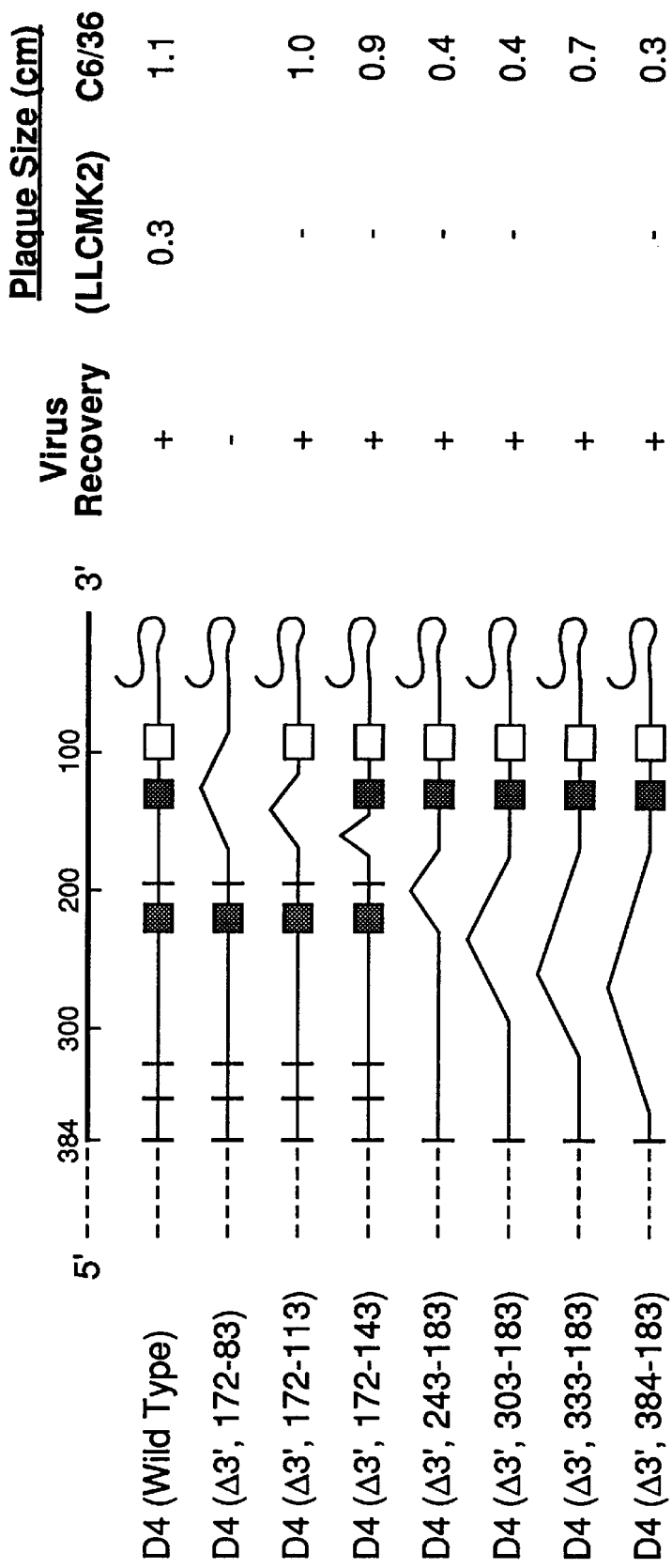

FIG. 13 provides the genome structure and properties of dengue type 4 virus mutants containing deletions in the 3' noncoding sequence.

The linear map shown depicts the 384-nucleotide 3' noncoding sequence of dengue type 4 virus. In this region at least three sequence elements are shown: the conserved sequence 2 (CS-2) at nt 234 to nt 211 and at nt 143 to nt 120 as indicated by the filled boxes. The conserved sequence 1 (CS-1) at nt 105 to nt 82 as indicated by the open box, and the stem-and-loop structure within the last 84 nucleotides. Seven cDNA clones, each containing a deletion mutation ranging from 30 to 202 nucleotides in length at positions specified, were constructed and the derived RNA transcripts used for transfection of permissive LLC-MK$_2$ cells. Mutant D4 (Δ3', 172-83) cDNA which lacks the entire CS-1 sequence was apparently lethal since a viable virus was not detected after repeated attempts. Viable deletion mutants were recovered from the remaining six RNA transcripts. The growth properties of wild type virus and its derived deletion mutants were compared by plaque assay on LLC-MK$_2$, cell monolayers stained six days after infection. Under the same conditions, wild type virus showed plaques of approximately 0.3 cm in size. The reverse numbering system was used to assign nucleotide positions of dengue type 4 virus. The last nucleotide at 10646 is assigned nt 1 using this numbering system.

Figure 14:
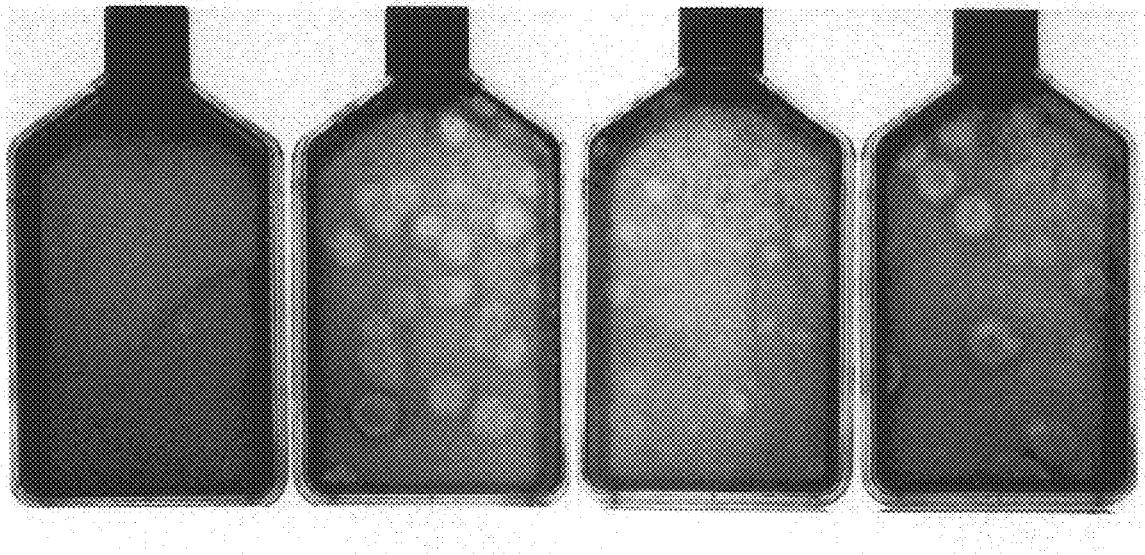

FIG. 14 illustrates the plaque morphology of wild type dengue 4 virus and the derived mutants containing deletions in the 3' noncoding region.

Plaque assay were performed on mosquito C6/36 cells. Confluent mosquito C6/36 cells in a 75-cm² flask were infected with wild type dengue type 4 virus, or viable deletion mutant viruses at an appropriate multiplicity. As described in the examples, infected cells were stained with neutral red six days after infection. The plaque size was measured the next day. The average plaque size of 10 individual plaques was calculated for each mutant. Panel A shows uninfected cell monolayer (Mock), dengue type 4 virus deletion mutants, (Δ3', 172-113), (Δ3', 172-143), and the parental wild type virus.

Figure 15:
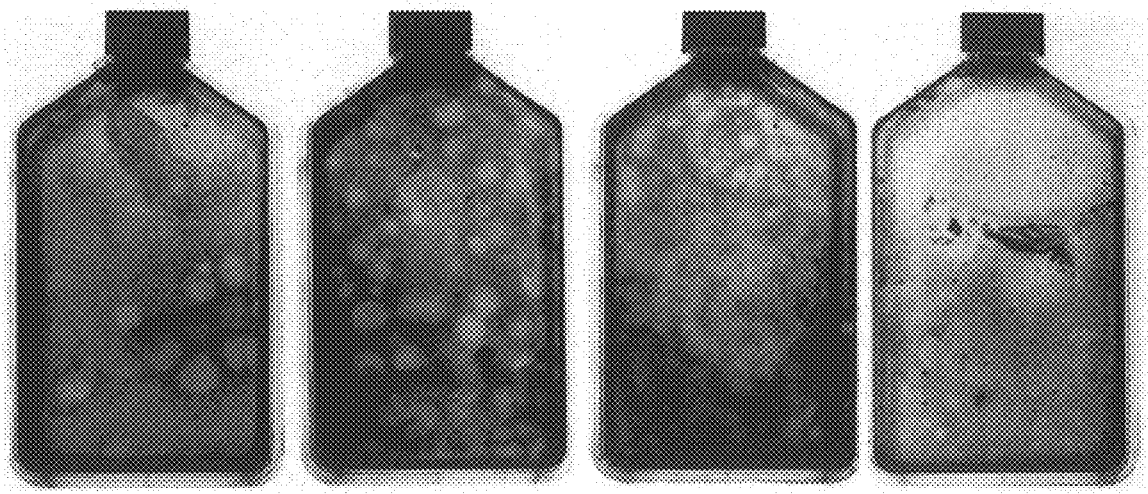

FIG. 15 shows wild type virus and several deletion mutants including (Δ3', 243-183), (Δ3'303-183), and (Δ3'384-183). The reverse numbering system was used to assign the deletion positions of the dengue type 4 sequence.

FIG. 16 provides a table of NS1–NS2A junctions.

FIG. 17 provides the intergenic junctions in chimeric TBEV/DEN4 constructs. Restriction enzyme cleaved TBEV cDNA fragments were inserted into DEN4 cDNA at appropriate sites as indicated by the underlined sequence. The amino acids and the encoding nucleotide sequences of TBEV are in bold letters. The nucleotide numbering system is that disclosed by Pletnev et al., *Virology* 174:250–263 (1990).

Figure 18:
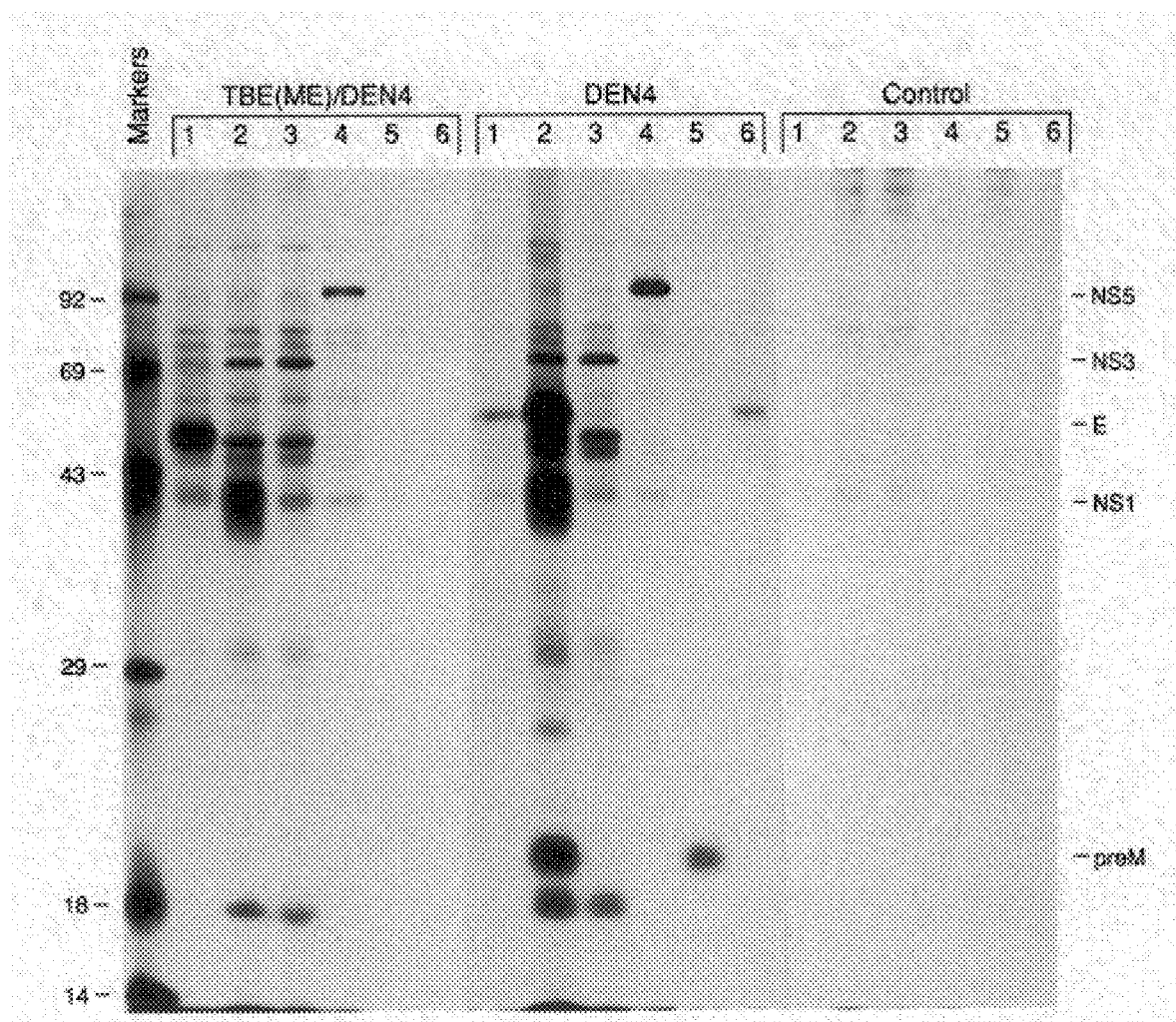

FIG. 18 is a photograph of polyacrylamide gel separation of viral proteins produced by parental DEN4 and chimeric TBE(ME)/DEN4 viruses. [$^{35}$S]Methionine-labeled lysates of vTBE(ME)/DEN4 or DEN4 virus-infected, or uninfected simian cells were immunoprecipitated using TBEV HMAF (1), or DEN4 HMAF (2), or rabbit serum specific to NS3 (3), or NS5 (4), or preM (5), or E (6) of DEN4 and analyzed on an SDS-12% polyacrylamide gel. The molecular weights of protein markers are in kilodaltons. The locations of DEN4 proteins are indicated along the right margin.

Figures 19A, 19B:
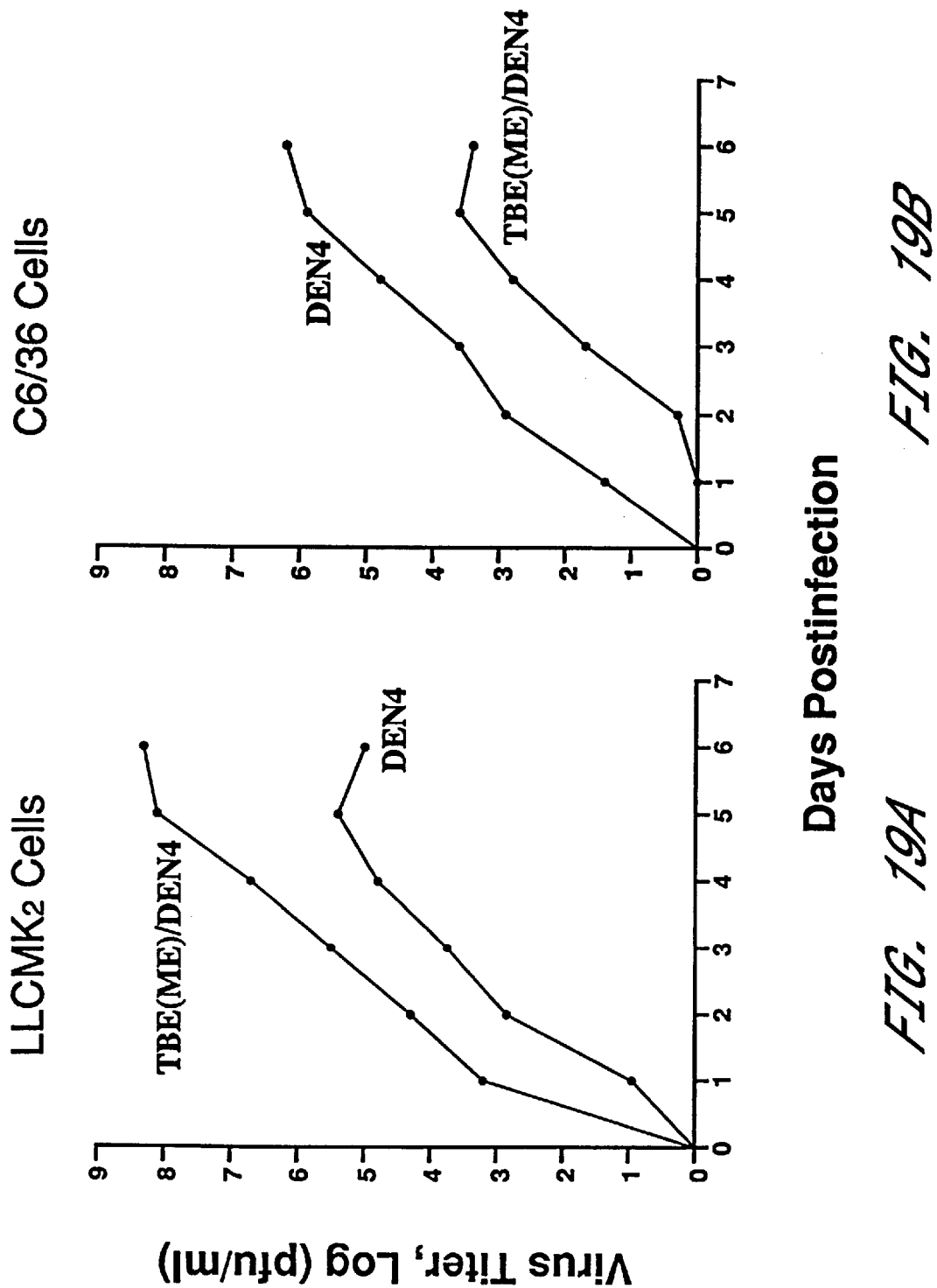

FIG. 19A, 19B provides the growth curves for vTBE (ME)/DEN4 and DEN4 on LLC-MK$_2$ and C6/36 cells. Cells were harvested at indicated times (days after infection) at an MOI of 0.01 pfu/cell, and the virus titer was determined by a plaque assay.

Figure 20:
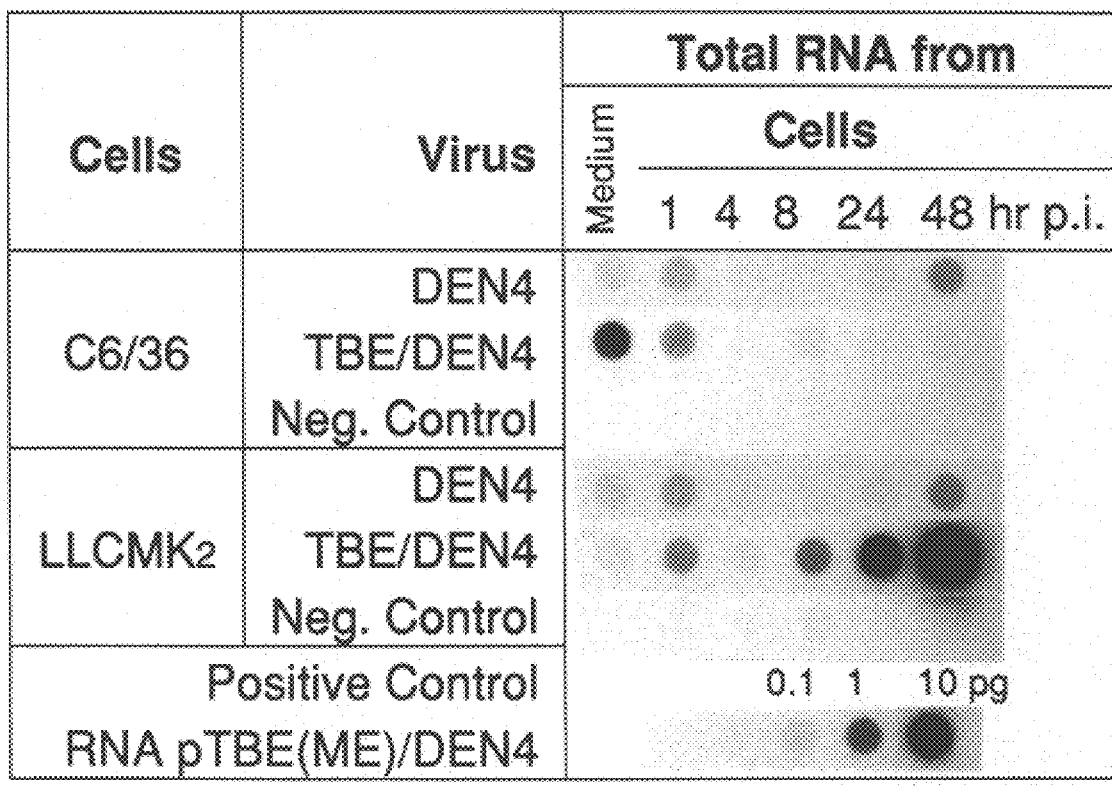

FIG. 20 is a copy of a photograph of a nitrocellulose filter blotted with samples of RNA isolated from infected tissue culture cells. The filters were probed with [$^{32}$P]-labeled pTBE(ME)/DEN4 nick-translated DNA.

FIG. 21 provides the results of a study to determine the protective efficacy and neurovirulence of vTBE(ME)/DEN4 in mice.

FIG. 22 provides a listing of several exemplary mutations incorporated into the TBE(ME)/DEN4 construct to assess the effect of the mutations on neurovirulence.

FIG. 23 summarizes the results of the neurovirulence studies using recovered TBE(ME)/DEN4 chimeras from constructs containing mutations provided in FIG. 22.

Figure 24:
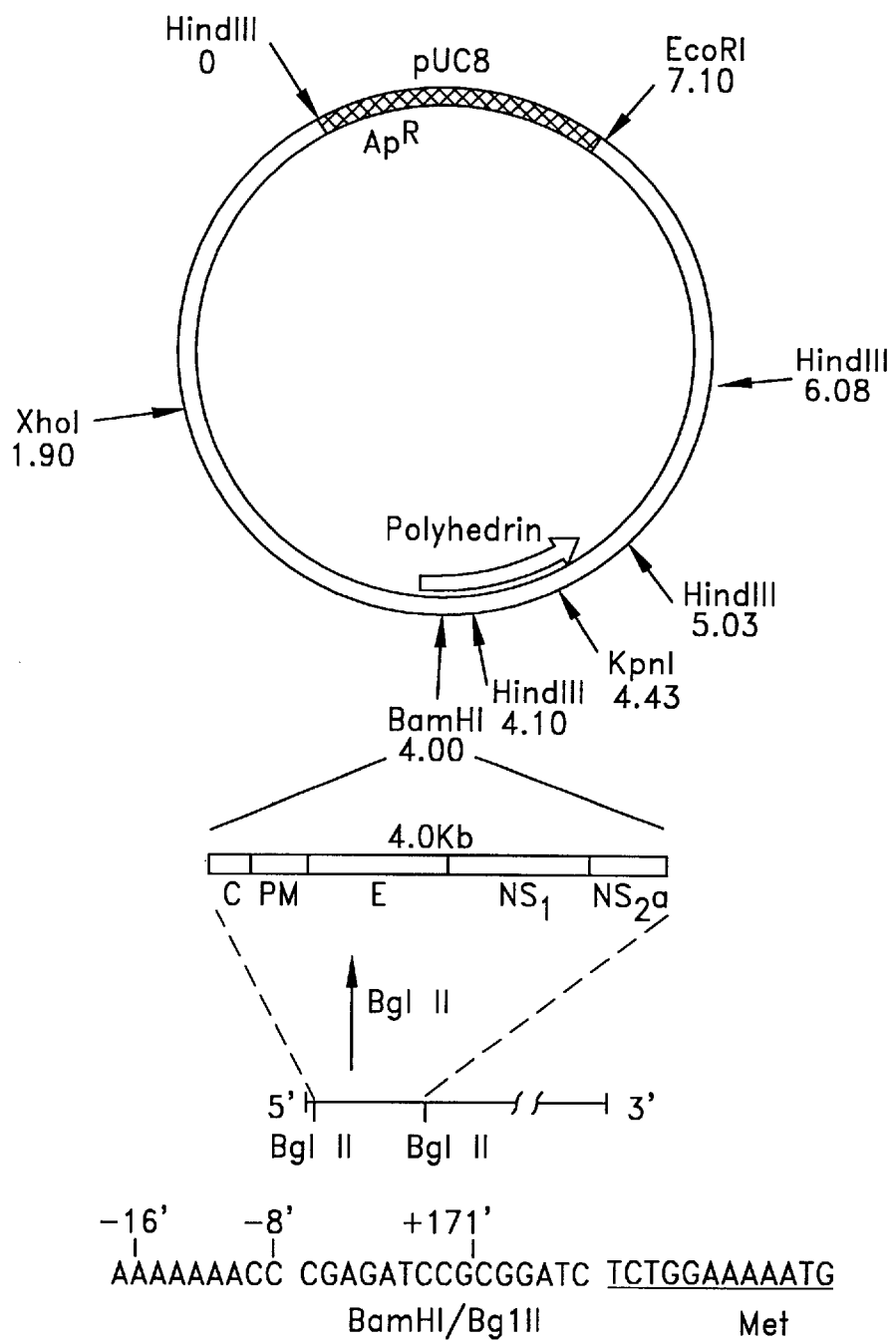

FIG. 24 is a construction of recombinant dengue DNA in baculovirus intermediate vector. Vector pAC373 DNA, provided by M. Summers, contains a 10-nucleotide polylinker including a unique Bam HI site at −8 and +171 of the polyhedrin structural gene. Plasmid components (pUC 8 and Ap$^R$;) and several other landmark restriction enzyme cleavage sites are shown. The BglII cleaved dengue DNA fragment (nucleotides 88–4128) that codes for the viral structural proteins, nonstructural proteins NS1 and NS2a in one open reading frame was inserted into the Bam HI site of pAC373. Recombinant DNA containing the insert in the sense orientation was isolated for construction of recombinant baculovirus. The 5'-noncoding sequence depicting the juncture between the polyhedrin gene and the dengue gene (underlined) is shown.

Figure 25:
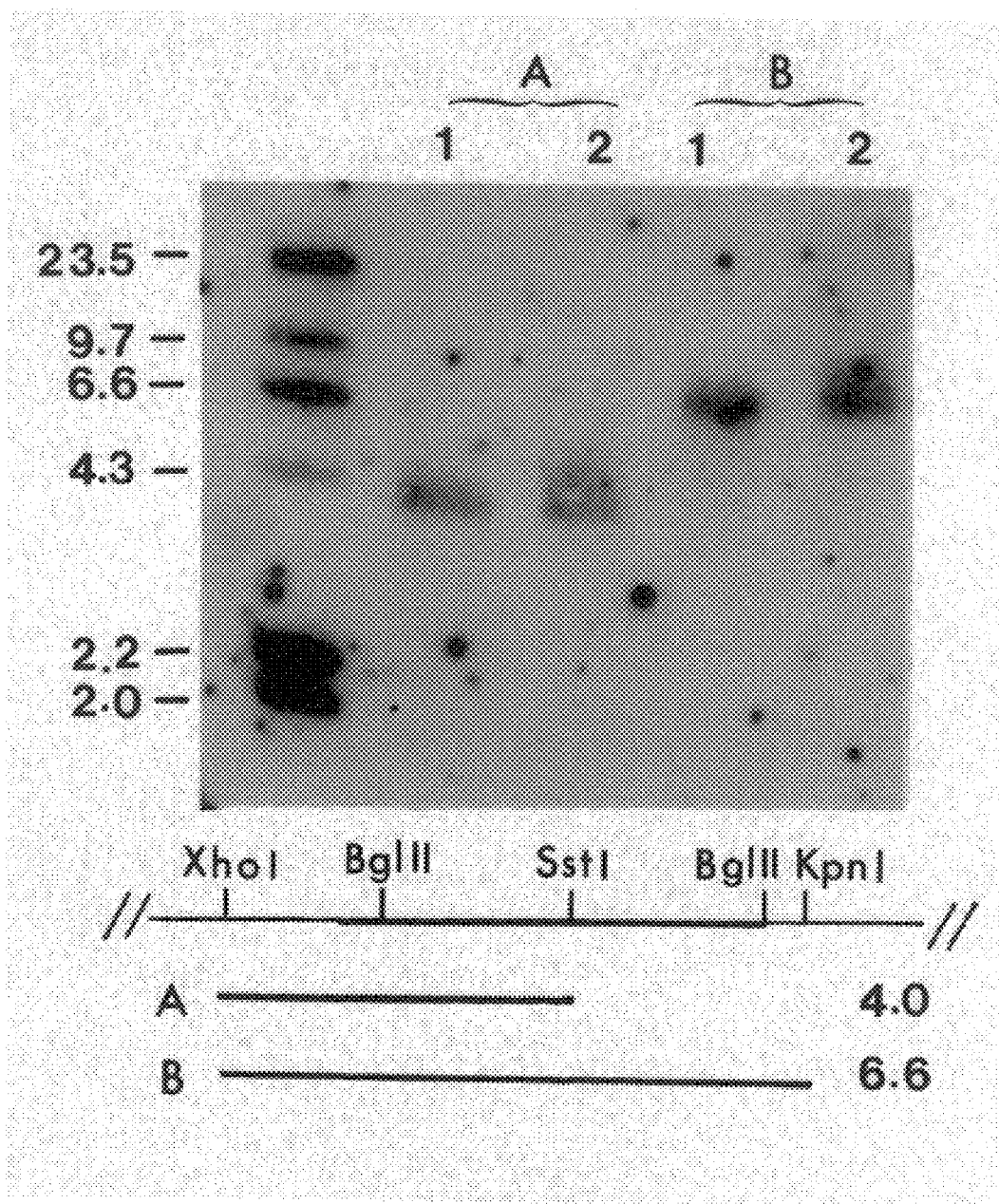

FIG. 25 is a Southern blot analysis of dengue genomic DNA present in recombinant baculovirus. Recombinant plasmid pAC373 containing the 4.0 Kb dengue sequence (lane 1) and genomic DNA prepared from recombinant baculovirus (lane 2) were separately digested with restriction enzymes XhoI plus SstI (A) or XhoI plus KpnI (B). The digests analyzed by Southern blot with a $^{32}$P-labeled oligonucleotide probe (nucleotides 1303–1326 of the dengue sequence) detected the 4.0 Kb and the 6.6 Kb DNA fragments. Size markers at the left were derived from lamda DNA digested with HindIII.

Figure 26:
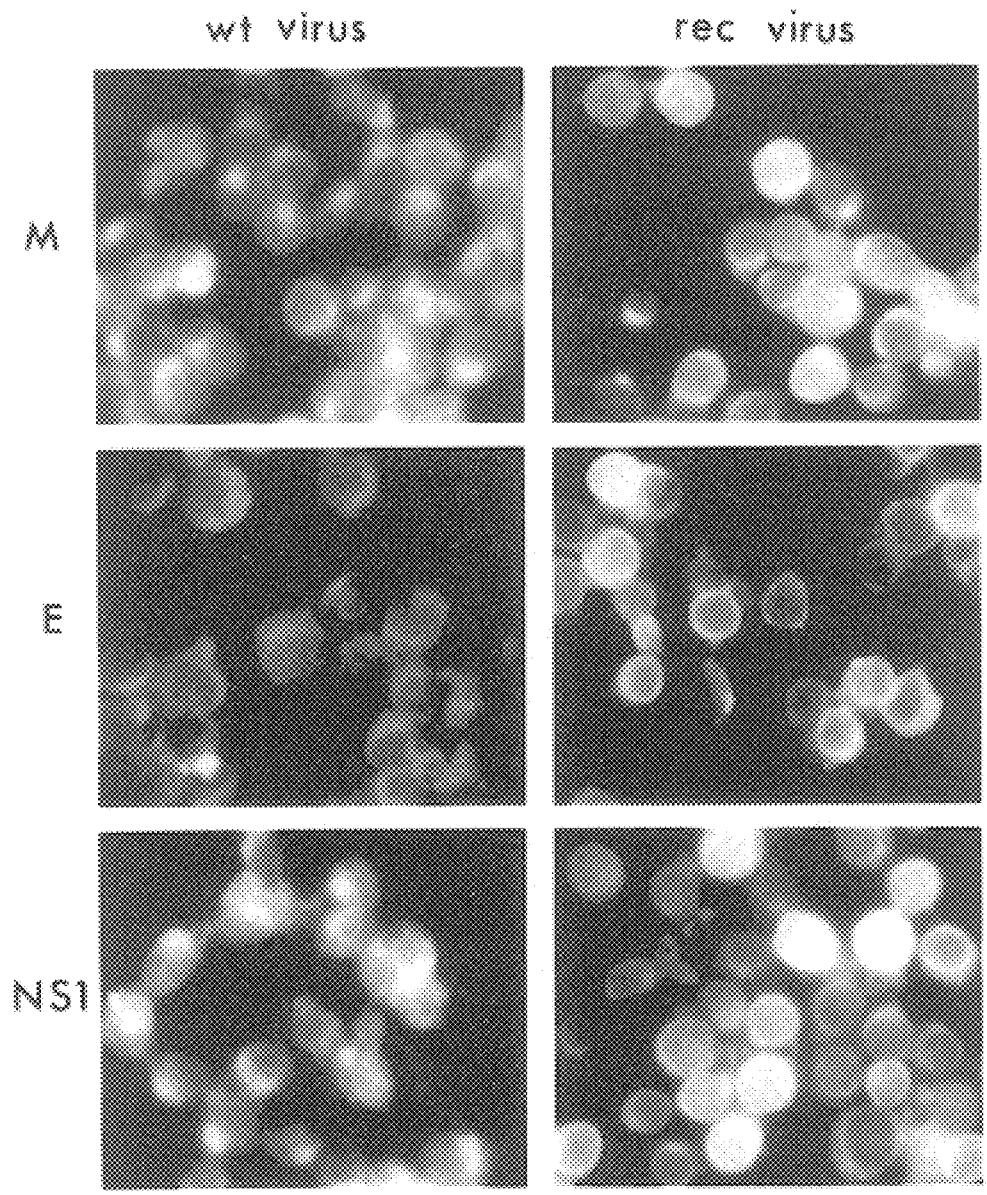

FIG. 26 is a detection of dengue virus proteins by indirect immunofluorescence assay. Monolayers of Sf9 cells were infected with wild type baculovirus (wt) or recombinant baculovirus (rec). Two days after infection cells were fixed with cold acetone and prepared for detection of dengue viral specific proteins by indirect immunofluorescence. Monoclonal antibody (mAb) 4H9 was used to detect M (or PreM); mAb 1H10 was used to detect E; and mMb 1G6 was used to detect NS1. Recombinant virus infected cells shown intense specific fluorescein staining.

Figure 27A:
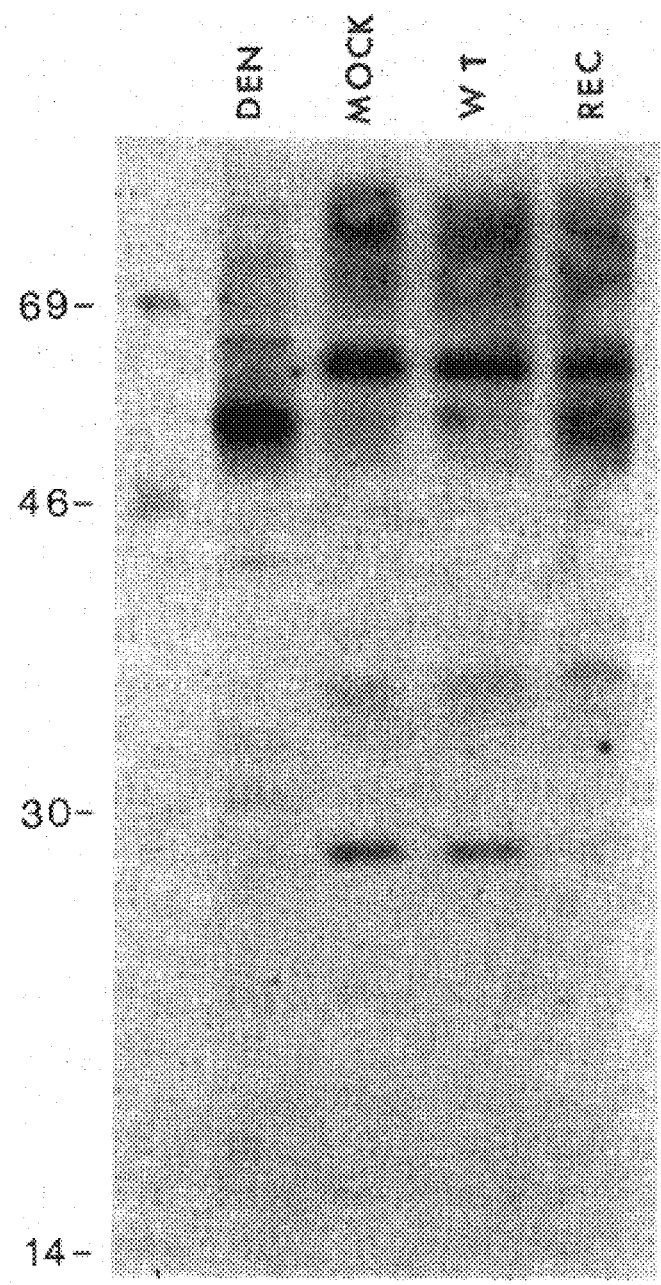
Figure 27B:
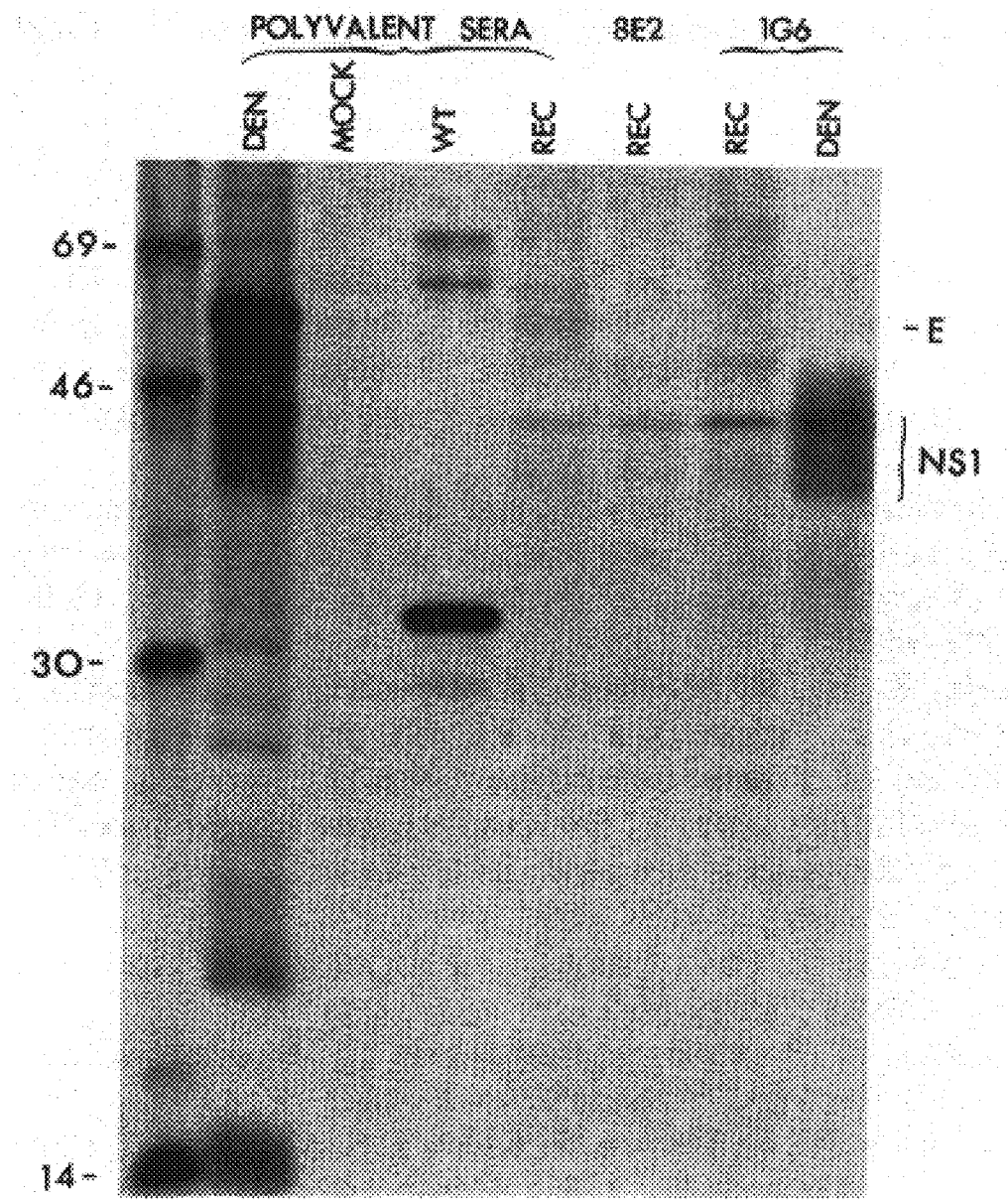

FIGS. 27A, 27B is an analysis of dengue envelope glycoprotein (E) and nonstructural protein NS1 produced by baculovirus recombinant.

(a) Lysates analyzed on 12 percent SDS-polyacrylamide gels were prepared from dengue type 4 virus-infected LLCMK$_2$ cells (DEN), uninfected moth Sf9 cells (MOCK), wild type baculovirus-infected cells (WT), and recombinant virus-infected cells (REG). Rabbit antiserum raised against a dengue E peptide (amino acids 260–273) and $^{125}$I-protein A were used for detection of the E glycoprotein by "western" blot.

(b) Radio-labeled lysates similar to those described in (a) were prepared for immunoprecipitation followed by separation on SDS-polyacrylamide gel. Mouse polyvalent antisera and two NS1-specific monoclonal antibodies, 8E2 and 1G6 were used. Protein size markers in kilodaltons are shown on the left. Note: Monoclonal antibodies do not immunoprecipitate a 40–42 Kb protein from uninfected Sf9 cells or wild type baculovirus infected cells (data not shown).

Figure 28:
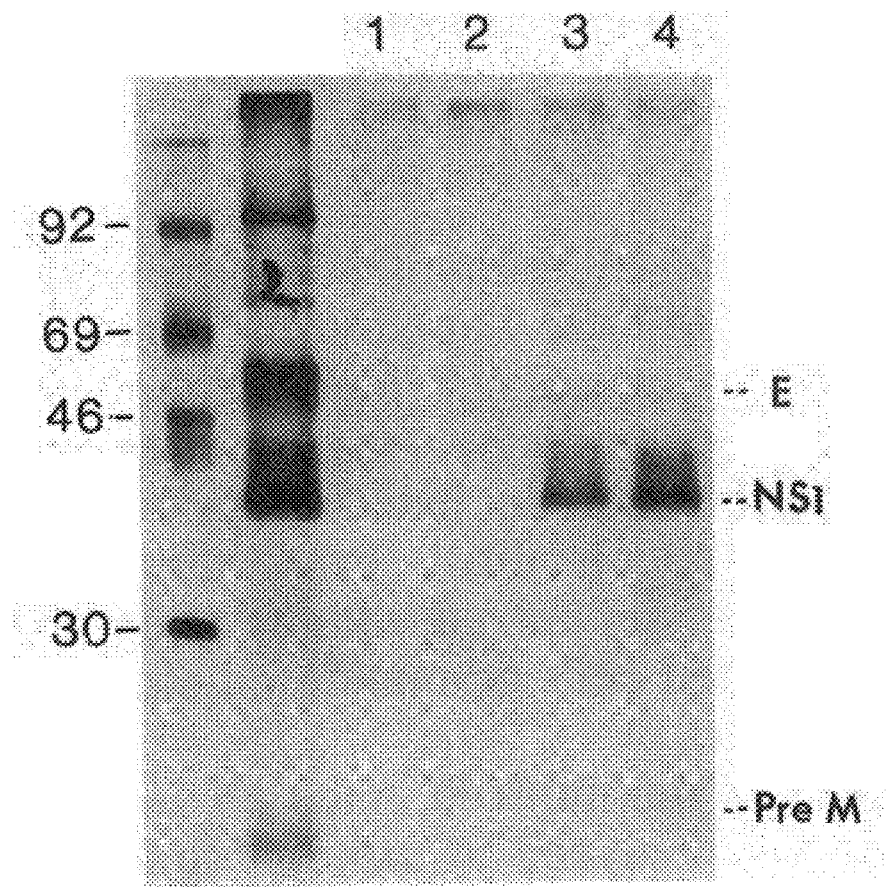

FIG. 28 is an immune response of rabbits to recombinant baculovirus infected cell lysate analyzed by radio-immunoprecipitation. Two rabbits were immunized with a lysate of wild type baculovirus-infected Sf9 cells (lanes 1 and 2), or a lysate of recombinant baculovirus-infected Sf9 cells (lanes 3 and 4). Serum obtained 4 weeks after primary immunization was tested for dengue-specific antibodies by immunoprecipitation of $^{35}$S-methionine labeled dengue viral proteins by mouse hyperimmmune antiserum shown on the left, while protein size markers are shown on the far left.

Figure 29:
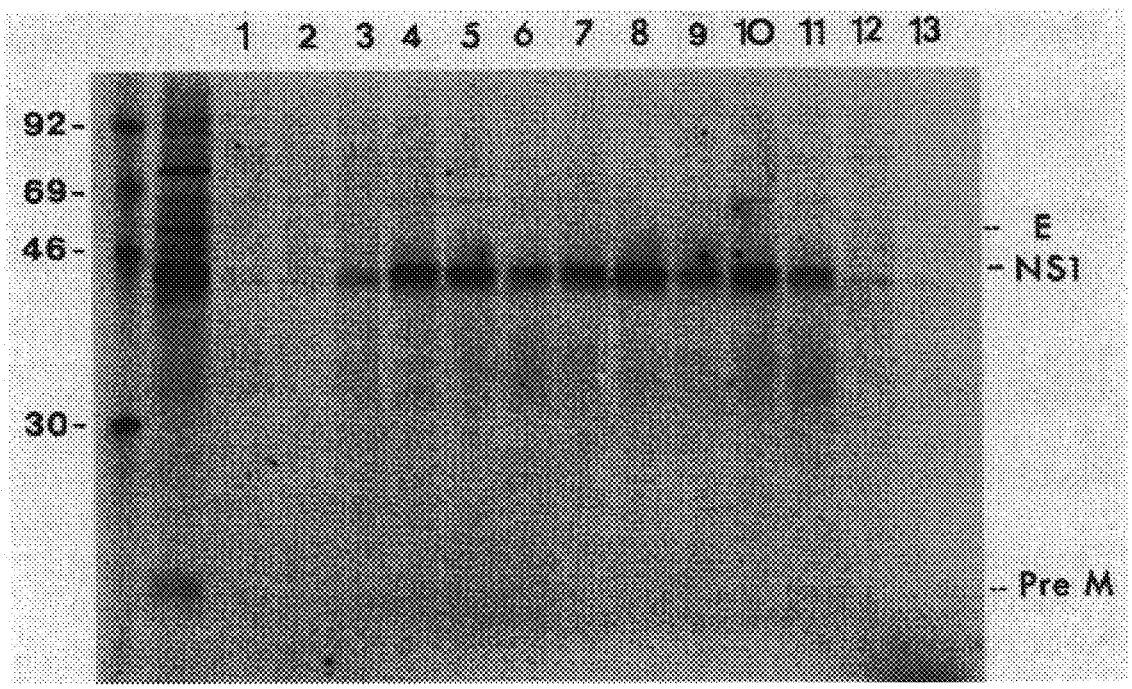

FIG. 29 is an immune response of mice to recombinant baculovirus-infected cell lysate analyzed by radio-immunoprecipitation.

Mice were inoculated with a lysate of recombinant baculovirus-infected Sf9 cells (lanes 3 to 11). Control mice received a lysate of wild type baculovirus-infected cells (lanes 12 and 13) or a lysate of uninfected cells (lanes 1 and 2). Serum was collected 3 weeks after initial immunization and tested by immunoprecipitation of $^{35}$S-methionine labeled dengue viral proteins. Dengue protein markers and standard protein size markers shown on the left are the same as described in FIG. 28.

DETAILED DESCRIPTION OF THE INVENTION

Generation of Chimeric Flaviviruses

Dengue virus contains an approximately 11-kilobase positive strand RNA genome, which codes in one open reading frame for three structural proteins (capsid (C), premembrane (preM) and envelope (E)), followed by seven non-structural proteins (NS1, NS2A, NS2B, NS3, NS4A, NS4B, NS5).

The present invention relates to a chimeric dengue virus containing non-structural proteins from one "type" of dengue viruses or a flavivirus and structural proteins from a different "type" of dengue viruses or another flavivirus.

In one embodiment, the present invention relates to a chimeric virus comprising:

1) a non-structural region of type 1, 2, 3 or 4 dengue virus, yellow fever virus, Japanese encephalitis virus, tick-borne encephalitis virus, or a flavivirus and
2) a structural region selected from type 1 dengue virus, type 2 dengue virus, type 3 dengue virus, type 4 dengue virus, yellow fever virus, Japanese encephalitis virus, tick-borne encephalitis virus or a flavivirus wherein the structural region is from a different "type" dengue virus or flavivirus than the non-structural region.

In another embodiment, the present invention relates to a chimeric virus comprising:

1) a non-structural region of type 4 dengue virus (DEN4), and
2) a structural region selected from type 1 dengue virus, type 2 dengue virus, type 3 dengue virus, yellow fever virus, Japanese encephalitis virus, tick-borne encephalitis virus and a flavivirus. In one preferred embodiment, the virus is substantially free of type 4 dengue virus structural region. In a preferred embodiment, the virus comprises p2A(D1 WP) or p2A(D2 NGC) RNA.

In a further embodiment, the present invention relates to a chimeric virus comprising:

1) a non-structural region of type 1 dengue virus, and
2) a structural region selected from type 2 dengue virus, type 3 dengue virus, type 4 dengue virus, yellow fever virus, Japanese encephalitis virus, tick-borne encephalitis virus and a flavivirus.

In a further embodiment, the present invention relates to a chimeric virus comprising:

1) a non-structural region of type 2 dengue virus, and
2) a structural region selected from type 1 dengue virus, type 3 dengue virus, type 4 dengue virus, yellow fever virus, Japanese encephalitis virus, tick-borne encephalitis virus and a flavivirus.

In another embodiment, the present invention relates to a chimeric virus comprising:

1) a non-structural region of type 3 dengue virus, and
2) a structural region selected from type 1 dengue virus, type 2 dengue virus, type 4 dengue virus, yellow fever virus, Japanese encephalitis virus, tick-borne encephalitis virus and a flavivirus.

In another embodiment, the present invention relates to a chimeric virus comprising:

1) a non-structural region selected from yellow fever virus, Japanese encephalitis virus, tick-borne encephalitis virus, and a flavivirus and
2) a structural region selected from type 1 dengue virus, type 2 dengue virus, type 4 dengue virus, yellow fever virus, Japanese encephalitis virus, tick-borne encephalitis virus, and a flavivirus wherein said structural region is from a different virus than the non-structural region.

In a further embodiment, the present invention relates to a vaccine comprising at least one of the above-described chimeric viruses and a pharmaceutically and immunologically acceptable carrier.

The vaccine includes virus in a quantity selected depending on the route of administration. Although subcutaneous routes of administration are preferred, the above-described vaccine could also be administered by an intradermal route. One skilled in the art will appreciate that the amounts to be administered for any particular treatment protocol can be readily determined.

In yet another embodiment, the present invention relates to a vaccine comprising:

1) a chimeric virus comprising a non-structural region of type 4 dengue virus and a structural region of type 1 dengue;
2) a chimeric virus comprising a non-structural region of type 4 dengue virus and a structural region of type 2 dengue;
3) a chimeric virus comprising a non-structural region of type 4 dengue virus and a structural region of type 3 dengue; and
4) an attenuated type 4 dengue virus.

In one preferred embodiment, the attenuated virus contains a mutation (point mutation, deletion, addition, or a combination of the above) in a non-structural protein region (for example, an altered NS1–NS2 cleavage site sequence). In another preferred embodiment, the attenuated virus contains a mutation (point mutation, deletion, addition, or a combination of above) in the 3' non-coding region. In a further preferred embodiment, the attenuated virus contains a mutation (point mutation, deletion, addition, or a combination of above) in the 5' non-coding region. In another preferred embodiment, the attenuated virus is naturally derived or laboratory engineered.

In another embodiment, the present invention relates to a DNA segment which encodes at least one of the above-described viruses. In one preferred embodiment, the DNA segment contains a promoter (preferably, a eukaryotic, procaryotic, or viral promoter; more preferably, an SP6 or T7 promoter) operably linked to the structural and nonstructural regions. In another preferred embodiment the DNA segment comprises p2A(D1 WP) or p2A(D2 NGC).

Thus, using the methods provided in the examples below, it is contemplated that one with skill in the art can generate chimeric dengue virus vaccines comprising intertypic recombinants that combine structural regions of one member of the flavivirus family with nonstructural regions from another flavivirus family. In a preferred embodiment, chimeric dengue viruses are produced that incorporate the nonstructural proteins of dengue type 4 (DEN4) with the structural proteins of dengue type 1. For a further review of these methods see Bray, et al.(*Proc. Natl. Acad. Sci.* 88: 1042–1046, 1991.

Example 17, below, discloses the production of a chimeric virus that incorporates the nonstructural regions of dengue type 4 virus with the structural regions of tick-borne encephalitis virus (TBEV(CME)/DEN4) following the methods provided for dengue chimeric virus production in Example 1. Virus produced from these methods replicated in culture and was used to infect tissue culture cells or laboratory animals.

Mutations in the Dengue Genome Affecting Neurovirulence

We have also engineered a series of viable dengue virus mutants containing deletions in the 3' noncoding region which exhibit altered growth properties and plaque morphology in cell culture. Similarly, we have engineered another series of growth-restricted dengue virus mutants that contain amino acid substitutions in a novel cleavage site sequence in the non-structural protein region of the viral polyprotein. Dengue virus mutants with reduced replicative capacity are evaluated for reduced virulence in experimental animals to determine their suitability for use in a live virus vaccine.

In the present invention, the construction of growth-restricted dengue type 4 virus mutants containing deletions in the 3'-noncoding region was effected by using a full-length dengue type 4 virus cDNA clone for engineering deletions into the strategic regions. Deletion mutants can offer the benefit of being less subject to reversion of phenotype than nucleic acid substitution mutants.

Like other mosquito-borne flaviviruses, dengue type 4 virus has a 3'-noncoding sequence that contains conserved regions, designated conserved sequence 1 (CS-1) and conserved sequence 2 (CS-2), and a potential terminal stem-and-loop structure. Deletions ranging from 3–202 nucleotides can be introduced into various locations in the 384 nucleotide 3'-noncoding sequence of dengue type 4 cDNA. RNA transcripts prepared from a cDNA clone lacking sequence of the CS-1 region, but retaining the stem-and-loop structure do not produce progeny virus indicating that the deletion is lethal. On the other hand, infectious viruses can be recovered from most other 3' non-coding region deletion constructs.

Plaque assay of these mutants and the wild-type virus can be performed on mosquito cells (C6/36). The results of these analyses show that most of the deletion mutants form plaques that are reduced in size, ranging from 1.0 to 0.3 cm, dependent on the location and the extent of deletion. This form of altered plaque morphology indicates that these deletion mutants exhibit a growth-restriction phenotype. This panel of dengue virus mutants containing deletions in the 3' non-coding region can be evaluated for their infectivity and immunogenicity in experimental animals. Mutants which exhibit reduced virulence for experimental primates can be selected as candidate vaccine viruses for evaluation in humans.

The present invention also relates to a recombinant DNA construct comprising the DNA fragment containing a deletion in the 3' noncoding region, and a vector. The invention also relates to host cells transfected with the DNA construct. The invention also relates to a method of producing mutants of dengue type 4 virus, comprising the steps of introducing deletions mutations into the 3' noncoding region of the viral genome, and recovering infectious viruses harboring the deletion mutations.

In another embodiment, the present invention relates to a DNA fragment that encodes a dengue type 4 viral RNA, where the fragment contains a substitution in the sequence encoding one or more of eight amino acids at the C terminus of NS1 of the cleavage site of the non-structural protein NS1–NS2A. A summary of the substitutions is provided in FIG. 16. The present invention also relates to a DNA fragment that encodes a dengue type 4 viral RNA, where the fragment contains a substitution at the position coding for glycine, that is, the +1 position following the cleavage site of the non-structural protein NS1–NS2A. The invention further relates to an infectious RNA transcript of the DNA fragments described herein.

The construction of growth-restricted dengue type 4 virus mutants containing mutations in the nonstructural proteins can be effected by using the full-length dengue type 4 virus cDNA clone to engineer such strategic mutations. Mutations affecting the functional activity of dengue virus nonstructural proteins can cause growth restriction. For example, modification of a cleavage sequence or a viral protease moiety can result in suboptimal cleavage of the viral polyprotein, thus restricting viral growth.

We have selected the polyprotein NS1–NS2A cleavage site as a target for constructing dengue virus mutants that are growth restricted because of inefficient cleavage. We have shown that dengue type 4 virus NS1–NS2A cleavage requires an 8 amino acid domain at the C terminus of NS1. We have further demonstrated the effect of substitutions at each of these positions and Gly at position +1 following the cleavage site.

A panel of mutations of amino acid substitution in this domain have been evaluated for their effect on cleavage (see FIG. 16). Mutations that produced a wide range of effects on cleavage were identified and a number of such mutations were selected for incorporation into the full-length dengue type 4 virus cDNA clone. RNA transcripts derived from mutant cDNA have been used to transfect cells which produced viable dengue virus mutants bearing a defined mutation in the NS1–NS2A cleavage region. These mutants were first characterized by plaque assay on mosquito C6/36 cells. Several mutants produce plaques of reduced size indicating that these mutant viruses exhibits growth restriction in cell culture.

The present invention also relates to a recombinant DNA construct comprising the DNA fragment containing a substitution mutation in the sequence encoding for one or more of eight amino acids at the C terminus of NS1 of the cleavage site of the non-structural protein NS1–NS2A, and a vector. The invention also relates to host cells transfected with the DNA construct.

In addition, the present invention relates to a recombinant DNA construct comprising the DNA fragment containing a substitution at the position coding for glycine, that is, the +1 position following the cleavage site of the non-structural protein NS1–NS2A, and a vector. The invention also relates to host cells transfected with the DNA construct.

In another embodiment, the present invention relates to a vaccine for humans against dengue type 4, comprising a mutant dengue type 4 virus, as described above, exhibiting reduced virulence, in an amount sufficient to induce immunization against the disease.

The mutants of the invention can be evaluated in primates for: (1) virulence as measured by the duration of viremia and (2) immunogenicity as indicated by the type and magnitude of antibody response following viral infection. Dengue virus mutants that show reduced virulence but retain sufficient immunogenicity in monkeys can be evaluated during clinical trials in humans.

In a further embodiment, the present invention relates to the construction of dengue type 4 viruses containing mutations in the dengue type 4 3' noncoding region and/or nonstructural protein genes that confer satisfactory attenuation, and the use of each dengue type 4 virus mutants to construct intertypic chimeric viruses with the antigenic specificity of other dengue virus serotypes thereby creating attenuated viruses that might be used for prevention of disease caused by dengue type 1, type 2 or type 3 virus. Chimeric viruses can also be constructed with antigenic specificity for other flaviviruses, such as Japanese encephalitis and tick-borne encephalitis.

The current strategy for immunization against dengue favors the use of a vaccine preparation containing all four dengue serotypes. This would protect individuals in endemic areas from the risk of severe dengue Hemorrhagic Shock Syndrome resulting from subsequent infection with a different dengue serotype. Currently, candidate attenuated dengue vaccines are being prepared by a standardized technique that involves serial passage in cells of an unnatural host. Only a limited success has been achieved with these host range mutants. For example, while a dengue 2 vaccine was found to be satisfactorily attenuated, a dengue 3 vaccine prepared by this approach caused dengue fever in human volunteers.

The present invention provides a method for constructing viable chimeric dengue viruses. The present invention also provides methods of producing a vaccine effective against all four dengue serotypes using chimeric viruses that share a common dengue type 4 virus genetic background, that includes the type 4 virus 5' and 3' noncoding sequences as well as the sequence coding for all of its 7 nonstructural proteins.

For this purpose, we have constructed a type 4 dengue virus that contains deletions in the 3' noncoding system, or in one of the nonstructural protein genes and have shown that these dengue virus mutants exhibit a significant restriction of replicative capacity. Accordingly, mutations conferring satisfactory attenuation can be engineered within these common regions, resulting in a set of four cloned, attenuated dengue viruses that would separately express the four dengue serotype specificities. These viruses can include the parental type 4 virus, a type 1 (structural protein gene region) -type 4 chimera, a similar type 2-type 4 chimers and a similar type 3-type 4 chimera, as well as chimeras of Japanese encephalitis and tick-borne encephalitis.

Inactivated whole dengue virus vaccines have been shown to lack sufficient immunogenicity. Live virus vaccines attenuated by serial passage in cell culture have suffered from insufficient attenuation, genetic instability or over attenuation. A dengue type 2 vaccine is still in an early developmental stage. Live vaccines of the remaining three serotypes are not available. The present invention represents a technical breakthrough in the ability to construct dengue viruses with defined mutations in the viral genome.

Chimeric Tick-borne Encephalitis Virus Vaccine

Tick-borne encephalitis chimeric virus was prepared by incorporating the three structural protein sequences: capsid, membrane and envelope into a dengue virus construct containing sequences encoding nonstructural dengue virus protein.

It is likely that dengue/tick-borne encephalitis virus (TBEV) combination requires the cooperation of dengue virus and TBEV viral protein and nucleic acid sequences. The construct generated viruses that were less infectious than either native counterpart. DEN4 and TBEV have the same genome organization and share the same strategy of gene expression, but a comparison of sequences between the two viruses indicates that the sequence homology is relatively low (Pletnev, et al. *Virology* 174: 250–263 (1990) hereby incorporated by reference). For example, the amino acid identity between the two viruses is 15.4% for capsid protein (C), 15.9% for membrane protein (M), 36.5% for envelope glycoprotein (E) and 39.1% for nonstructural protein (NS1). The following embodiment discloses an improved chimeric TBEV vaccine.

We have previously described cloned full-length dengue virus cDNA that can be used as a template for in vitro transcription of infectious RNA. This was done by cloning stable full-length dengue cDNA copies in a strain of *E. coli* using the pBR322 vector. Dengue virus was recovered from permissive cells transfected with the in vitro RNA transcripts of the cDNA. The properties of the virus produced by cells transfected with infectious RNA transcripts of dengue cDNA were identical to the properties of the virus from which the cDNA clone was derived.

In addition, we have disclosed in this invention the production of a chimeric dengue virus having a genome containing nonstructural protein genes of one serotype of dengue virus and structural protein genes from another serotype of dengue virus. As one example of a chimeric dengue virus, the capsid, preM (membrane), and envelope gene sequences from one dengue virus were used to replace the corresponding genes of dengue type 4 virus in a recombinant cDNA construct. Viruses produced in cells transfected with this construct are useful in the preparation of vaccines against homotypic dengue viruses. As disclosed supra, this application additionally discloses the construction of chimeric virus containing gene sequences corresponding to a nonstructural region of a dengue virus and a structural region of another flavivirus. In particular, a chimeric tick-borne encephalitis virus is disclosed. The methods of this invention as outlined in the section entitled "Generation of Chimeric Flaviviruses", disclose the production of a recombinant dengue virus construct incorporating three structural proteins from TBEV. Virus produced from cells transfected with this construct are candidate virus for live virus vaccines.

The invention associated with this application provides a significant and unexpected improvement to the art of chimeric flavivirus production as well as compelling evidence for the utility of this novel vaccine strategy. One with skill in the art could expect that a chimeric flavivirus combination incorporating all of the structural proteins of one virus with the nonstructural elements of a second virus would be readily recoverable and efficiently replicate in cultured cells because of the possible requirement of functional cooperation of structural proteins derived from distantly related flaviviruses. However, unexpectedly, the present invention identifies a chimeric TBEV virus (TBEV/DEN4) containing two structural proteins (i.e. M and E) from the TBEV genome that assemble with a third structural protein (i.e. C) from dengue virus.

Production of Chimeric TBEV/DEN4 Constructs

Since the amino acid sequence homology between DEN4 and TBEV is low, a variety of TBEV and DEN4 chimeric cDNA constructs were made by replacing the corresponding DEN4 sequences with TBEV sequences. These constructs were prepared using techniques well known in the art of molecular biology. The constructs were tested to determine if any of the different gene combinations would yield a viable chimeric virus following in vitro transcription of the cDNA construct and transfection of the RNA product into susceptible cells. Previously, subgenomic cDNA fragments of TBEV (strain Sofjin) were cloned and the nucleotide sequences were determined using techniques well known in the art (see Pletnev, et al., *Virology, supra.* and Pletnev et al. *FEBS Lett.* 200: 317–321, 1986). These plasmids provide overlapping gene sequences that together include the entire TBEV genome sequence. Using plasmids pGEM2-CME or pGEM2-ENS1 as the template and appropriate oligonucleotide primers (see Example 17), a series of TBEV cDNA fragments were prepared by polymerase chain reaction (PCR), each fragment defining one or more specific genes flanked by restriction enzyme cleavage sites. The fragments are provided in FIG. 17 and the sequence of the fragments denoted by the nucleotide positions provided in the right margin are available in the publication by Pletnev, et al. *Virology* 174:250–263, 1990). FIG. 17 shows seven such TBEV cDNA fragments and the modified termini suitable for joining to the appropriate sites similarly introduced into full-length DEN4 cDNA RNA transcripts by site-directed mutagenesis. Plasmids pGEM2-CME containing nucleotides (nt) 76–1977 and pGEM2-ENS1 containing nucleotides 966–3672 of the TBEV sequence were constructed from plasmids p10, p4, p18, p2, p11 (see Pletnev, et al. *Virology,* 1990 *supra.*) by ligation of the TBEV fragments at shared restriction enzyme sites. Plasmids DEN4 p5'-2 and p5'-2(ΔPstI,XhoI) (Bray, et al., *Proc. Natl. Acad. Sci,* 1991 *supra*), and a derivative, p5'-2 (ΔPstI,XhoI,AHindIII) were used for substitution of one or more TBEV genes in place of the corresponding DEN4 genes. Those with skill in the art of molecular biology will be able to use the primer sequences SEQ ID NOS:21–31 as identified in Example 17 to generate the chimeric TBEV constructs. The sequences at the junctions of the chimeric constructs were verified by nucleic acid sequencing. All of the resulting chimeric plasmids contained the SP6 promoter positioned upstream of a transcription initiating G followed by an A residue representing the first DEN4 nucleotide. Prior to in vitro transcription, the plasmids were linearized at the unique Asp718 cleavage site immediately following the 3' end of the DEN4 sequence. The constructs were transcribed by in vitro transcription using techniques disclosed by Lai, et al. (*Proc. Natl. Acad. Sci.* 88:5139–5143, 1991). The transcription products from the chimeric constructs of FIG. 17 were tested for infectivity by transfecting the RNA into simian LLC-MK$_2$ cells.

Transfection procedures used either Lipofectin™ (Bethesda Research Laboratories, Inc., Gaithersberg, Md.) or DOTAP (N-[1-(2, 3-dioleoyloxy)propyl]-N, N, N-trimethylammoniummethylsulfate, Boehringer Mannheim, Indianapolis, Ind.) to introduce the chimeric RNA transcripts into permissive cells. While cultures of simian LLC-MK$_2$ cells were used in these procedures, it is contemplated that any permissive cell type for TBEV replication could alternatively be used. The transfected cultures were assessed for the presence of virus over time by immunofluorescence using TBEV-specific rabbit serum or hyperimmune mouse ascitic fluid. Cells transfected with RNA transcripts of pTBE(ME)/DEN4 (including sequences from the premembrane and envelope proteins of TBEV linked to capsid protein and nonstructural sequences of DEN4) stained positively with TBEV-specific rabbit serum, TBEV-specific hyperimmune mouse ascitic fluid (HMAF) and DEN4-specific HMAF. Control cultures infected with DEN4 alone were negative for immunofluorescently labelled TBEV-specific serum. This indicated that chimeric vTBE (ME)/DEN4 expressed both TBEV and DEN4 specific antigens.

Chimeric virus isolated from the transfections vTBEV and is designated TBE(CME)/DEN4 (genomic construct includes the capsid, membrane and envelope genes of TBEV and nonstructural sequences of DEN4)and vTBE(ME)/DEN4. As disclosed in Example 17, sixteen days after transfection with TBE(CME)/DEN4 RNA, approximately 1% of cells stained positively for TBEV and DEN4 specific antigens. The percentage of positive cells increased over time to provide a peak titer of 6×10$^5$ pfu/ml at day 26 post transfection, with 80% of the cells transfected. In contrast, cells transfected with TBE(ME)/DEN4 RNA produced virus more quickly and at day 16 100% of the culture was infected. In contrast, the titer of TBE(ME)/DEN4 virus (denoted v TBE(ME)/(DEN4)) present in transfected cells was 4×10$^6$ pfu/ml at day 26 post infection. In addition, the progeny virus produced from cells infected with the chimeric constructs was sequenced to confirm that the DEN4 and TBEV junctions of the genomic fragments from the chimeric virions still matched the junctions of the chimeric constructs as illustrated in FIG. 17.

Characterization of TBEV/DEN4 Viruses

Chimeric virus was characterized using the methods provided in Example 17 and all work with the chimeric TBEV/DEN4 viruses was conducted in a BL-3 containment facility.

Figure 4:
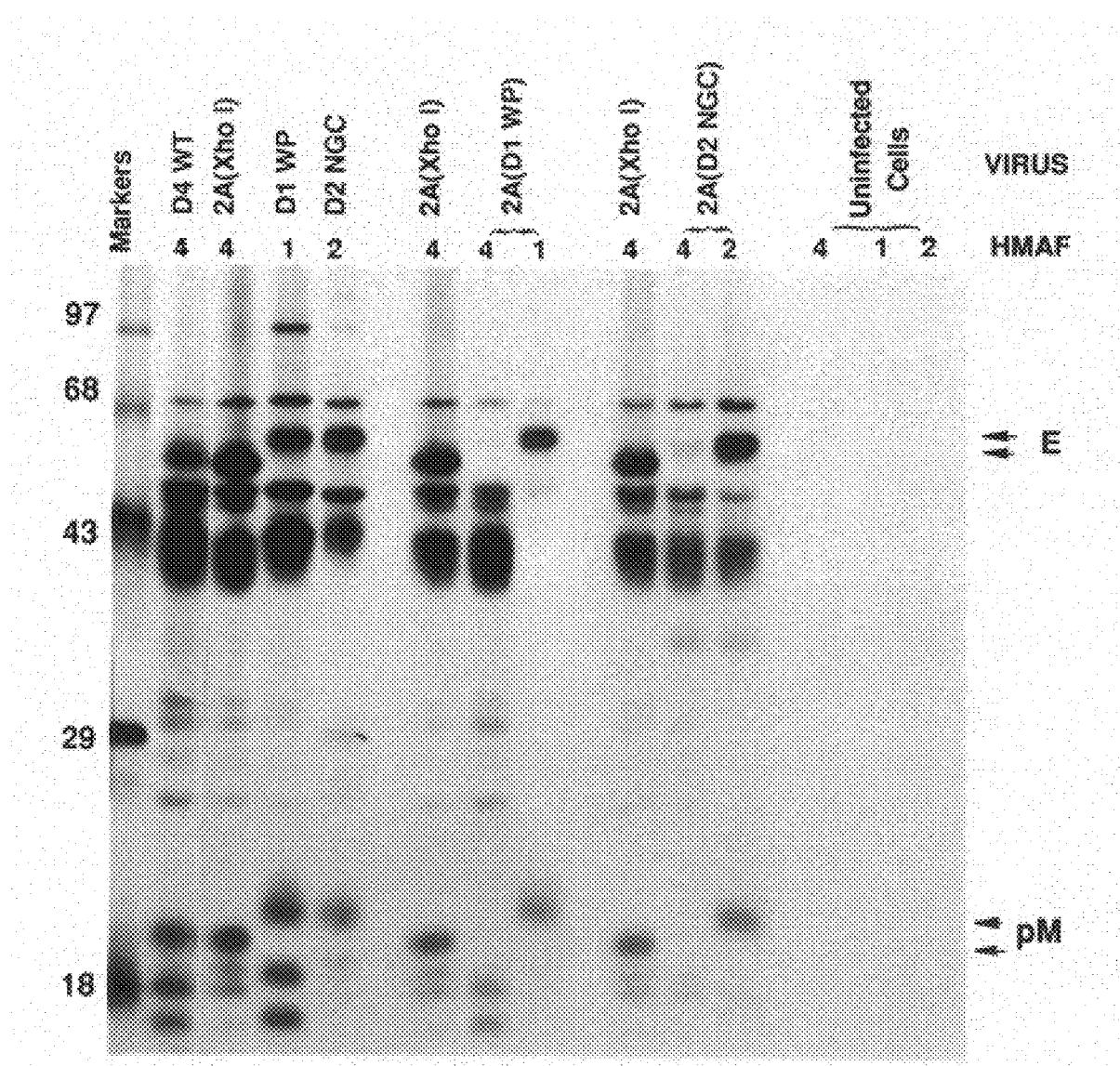
FIG. 4. Polyacrylamide gel analysis of dengue type 1, type 2, or type 4 viral proteins produced by parental or chimeric dengue viruses.
Figure 5:
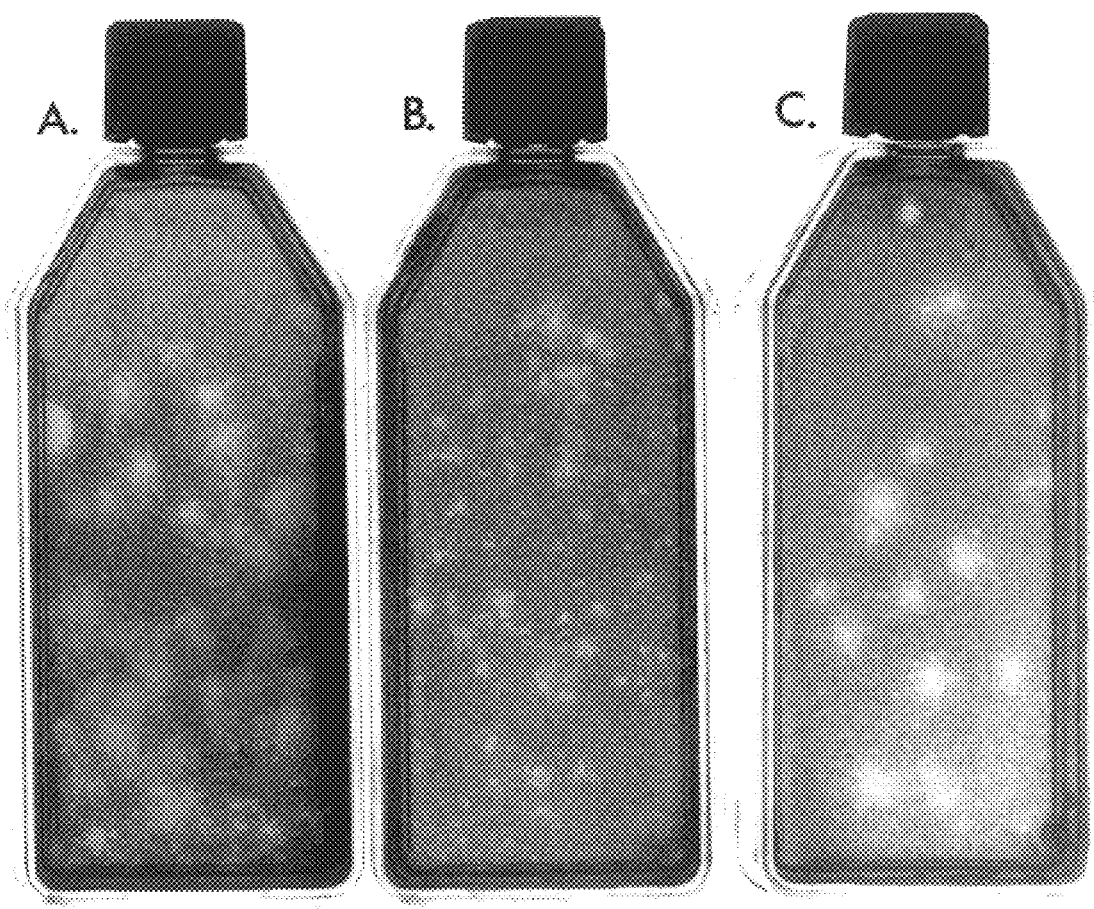
FIGS. 5A, 5B, 5C. Morphology of viral plaques on LLC-MK$_2$ cells.
Figure 6:
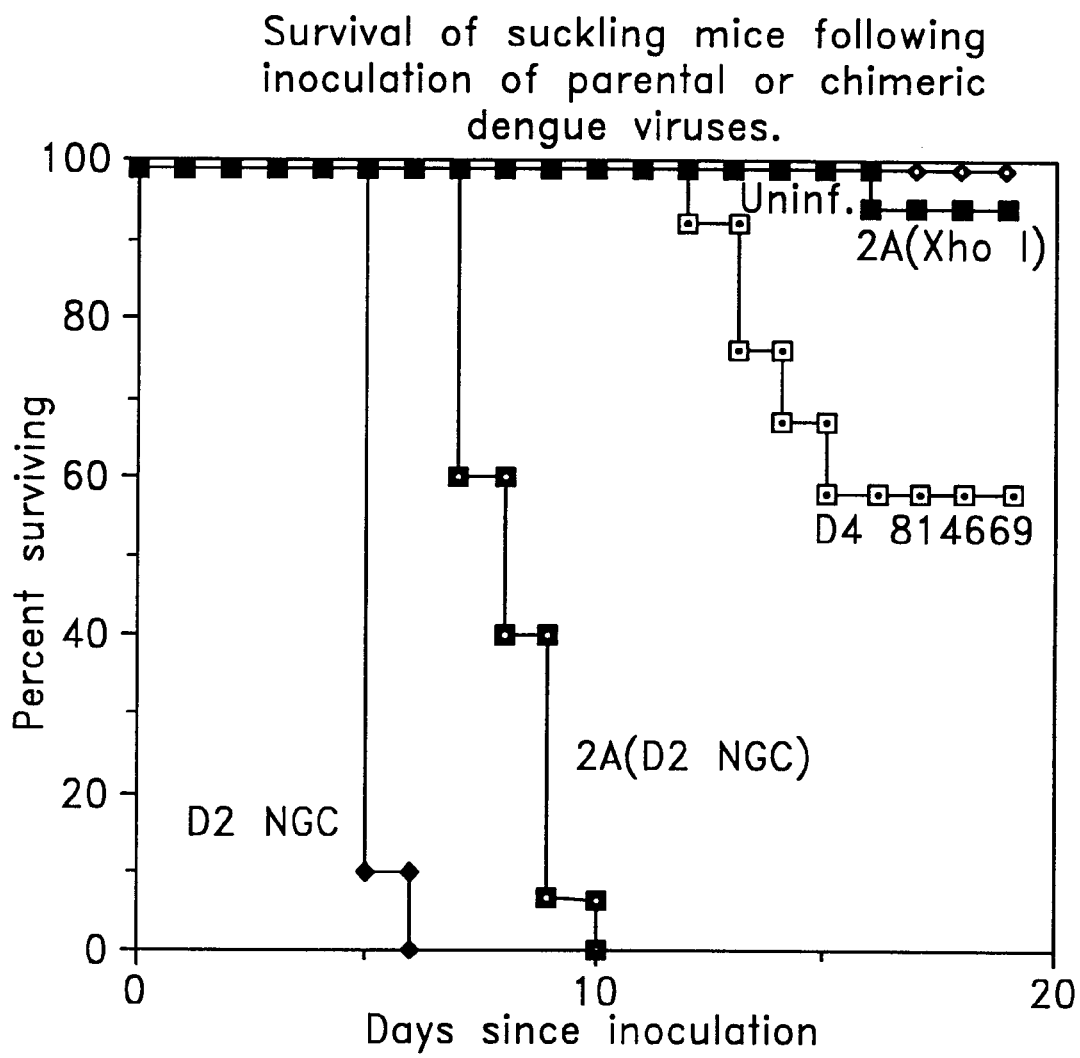
FIG. 6. Mouse neurovirulence of parental dengue type 2 NGC or dengue type 4 virus or type 2/type 4 chimeric virus.

The proteins produced from the chimeric viruses were compared to proteins produced from dengue 4 virus. Proteins of dengue 4 virus recovered from the full-length DEN4 cDNA clone were identified in the above section entitled "Generation of Chimeric Flaviviruses", illustrated in FIG. 4 and disclosed by Bray et al. (*Proc. Natl. Acad. Sci. USA* (1991), supra.). The pattern of protein separation of dengue virus protein was compared to chimeric viral proteins produced from vTBE(ME)DEN4 infected cells. In this assay (see FIG. 18 and Example 18) confluent LLC-MK$_2$ cells were infected at a multiplicity of infection (MOI) of 0.01. Infected cultures were incubated with $^{35}$S-methionine using techniques disclosed by Lai et al., *Proc Natl. Acad. Sci. USA* (1991), supra. Infected cell lysates were immunoprecipitated with Lane:1) TBEV-specific HMAF; 2) DEN4-specific HMAF; 3) rabbit serum raised against DEN NS3, 4) rabbit antiserum specific to DEN4 NS5, 5) rabbit antiserum specific to DEN4 preM, or 6) rabbit antiserum specific to DEN4 E protein. Immunoprecipitates were analyzed by polyacrylamide gel electrophoresis (PAGE) under denaturation conditions, as illustrated in FIG. 18, using techniques disclosed by Laemmli (*Nature* 227: 680–685, 1970). Both chimeric and parental DEN4 viruses produced protein bands identified as DEN4 NS3 and NS5 (lanes 3 and 4). DEN4 preM or E proteins were not identified in cells infected with the chimeric virus but were identified in DEN4-infected cells (see lanes 5 and 6). DEN4 specific HMAF precipitated only protein bands from vTBE(ME)/DEN4-infected cell lysate that comigrated with DEN4 NS1 and NS3 nonstructural proteins (lane 2). TBEV HMAF immunoprecipitated a protein having the correct size for TBEV E protein (55kDa) from the lysate of cells infected with chimeric vTBE(ME)/DEN4. The chimeric virus-infected cell protein migrated faster than DEN4 E (lanes 1 and 6). In previous experiments TBEV HMAF failed to precipitate native TBEV preM and C proteins from TBEV infected cells. Therefore, identification of TBEV preM and C proteins was not expected. The profile of protein bands produced in LLC-MK$_2$ cells by vTBE(CME)/DEN4 was identical to that produced by vTBE (ME)/DEN4. Thus, the chimeric viruses produced the expected proteins in LLC-MK$_2$ cells.

The plaque morphology of the viruses was assessed by comparing the viral plaques produced by DEN4 with those of plaques produced from the chimeric constructs. DEN4 viral plaques had an average size of 12.1 mm on mosquito C6/36 cells, whereas vTBE(ME)/DEN4 produced plaques averaging 6.5 mm. In contrast, vTBE(ME)/DEN4 produced plaques that were 5-fold larger than those produced by DEN4 on simian LLC-MK$_2$ cells. This suggested that the chimeric virus replicated more efficiently in LLC-MK$_2$ cells than did DEN4. These unexpected results were confirmed by analysis of the growth rate and the viral yield of vTBE(ME)/DEN4 in infected LLC-MK$_2$ cells (see FIG. 19).

The chimeric virus reached a titer of $10^8$ pfu/ml which is approximately 1000-fold higher than that attained by parental DEN4, under the same conditions. Chimeric vTBE(ME)/DEN4 virus grew slowly on mosquito C6/36 cells and reached a titer 100-times lower than that produced by parental DEN4. The plaque size of chimeric vTBE(CME)/DEN4 did not differ appreciably from that of DEN4 on LLC-MK$_2$ cells. In these studies, virus was quantitated by plaque assay using techniques disclosed by Bancroft, et al. (Pan Am. Health Organ. Sci. Publ. 375: 175–178, 1979). The difference in plaque size may reflect an incompatibility of TBEV C protein with DEN4 viral RNA which prevents efficient interaction of the proteins during viral RNA packaging and viral maturation. It is also possible that the difference in plaque size is the result of a substitution of the six nucleotides upstream of the AUG codon in the DEN4 5' noncoding region. This sequence change could influence the efficiency of viral protein translation.

Analysis of viral RNA production (FIG. 20) from the chimeric constructs provides an explantion for the small-plaque phenotype. Cultures of LLC-MK$_2$ or C6/36 cells (approximately $10^6$ cells) were collected at various times following virus adsorption, and lysed in buffer containing sodium dodecyl sulphate (SDS). Total RNA was isolated from the cell lysate and the medium by phenol extraction using techniques provided by Maniatis, et al. (Molecular Cloning, A Laboratory Manual. 1982 Cold Spring Harbor Laboratory, New York). RNA samples were denatured in formaldehyde and applied to a nitrocellulose filter (BA85, Schleicher and Schuell. The filters were hybridized with a nick-translated, [$^{32}$P]-labeled PTBE(ME)/DEN4 DNA probe. RNA transcripts made in vitro from pTBE(ME)/DEN4 were used as a positive control.

Viral proteins from DEN4-infected LLC-MK$_2$ or C6/36 cells were compared to viral proteins from vTBE(ME)/DEN4-infected LLC-MK$_2$ or C6/36 cells. DEN4 viral proteins including E, NS1 and NS3 accumulated to a high level in DEN4-infected LLC-MK$_2$ or C6/36 cells by 48 hr after infection. However, the kinetics of viral protein synthesis differed between vTBE(ME)/DEN4-infected LLC-MK$_2$ and C6/36 cells. Viral proteins were detected as early as 8 hr postinfection in LLC-MK$_2$ cells, whereas viral proteins were not detected in C6/36 cells until 48 hr after infection. Approximately 70% of the vTBE(ME)/DEN4 virions remained in the medium following inoculation onto C6/36 cells, whereas only a small fraction of the inoculated virus was found in medium of LLC-MK$_2$ cell cultures. This finding suggests that entry of chimeric vTBE(ME)/DEN4 into LLC-MK$_2$ cells was more efficient than was entry into C6/36 cells and possibly as a consequence, the virus grew more slowly and to a lower titer in these cells as compared with DEN4 virus. Following entry into the LLC-MK$_2$ cells, replication of chimeric viral RNA was more rapid than that of DEN4 viral RNA. On the other hand, RNA synthesis of chimeric virus was slower than that of DEN4 in infected C6/36 cells. Thus, vTBE(ME)/DEN4 exhibited reduced efficiency of entry into mosquito cells and this was associated with a reduced production of viral RNA and proteins.

These observations are consistent with the low efficiency of transfection of TBEV viral RNA into C6/36 cells. (Mandl, et al. J. Virol 65: 4070–4077, 1991).

It will be understood by those of skill in the art, that there are a variety of methods that could be used to incorporate the nucleic acid sequences from one virus with the nucleic acid sequences of another virus. Such ligation schemes and cloning strategies are known in the art. Therefore it is contemplated that other techniques could be used and the employment of these techniques would not detract from the claimed invention.

Efficacy of the Chimeric Vaccine and Determination of Neurovirulence vTBE(ME)/DEN4 was assessed for protective efficacy as a vaccine by introducing the virus preparation into test animals through various routes of administration. The neurovirulence of vTBE(ME)/DEN4 as compared to parental dengue virus was analyzed by inoculating mice intracerebrally (IC). Other administration routes included intradermal (ID) or intraperitoneal (IP) injections. In one experiment, three-day-old suckling BALB/c mice were injected IC with a dose of $10^2$ pfu of virus in 0.02 ml of MEM/0.25% human serum albumin and in another set of experiments, six-week-old BALB/c female mice were inoculated IC, ID or IP. Mice were observed for 21 days for symptoms of encephalitis or death, and surviving adult mice were bled 20 days after infection to evaluate the antibody response to TBEV. Surviving mice were challenged IP at 21 days postinfection with $10^3$ LD$_{50}$ TBEV (strain Sofjin) in a BL-4 containment facility to determine the protective efficacy of the vaccine.

vTBE(ME)/DEN4 retained the neurovirulence of its TBEV parent when inoculated directly into the brain (IC) of suckling or adult mice (FIG. 21 and Example 21). As a positive control, comparisons were made to a representative strain of TBEV (strain Sofjin). TBEV is highly neurovirulent and 0.1 pfu readily caused fatal encephalitis in 50% of suckling mice inoculated IC. Similarly, TBEV was also highly neurovirulent for adult mice inoculated by IP. In this case, the ID$_{50}$ was 14.2 pfu. In contrast, vTBE(ME)/DEN4 did not cause encephalitis when inoculated by a peripheral route, either ID or IP (See FIG. 21) indicating that were safe potentially safe routes for vaccination.

The immunogenicity of vTBE(ME)/DEN4 was analyzed by immunoprecipitation of antibody to the virus using [$^{35}$S]-labeled antigens using serum antibody of surviving mice. Analysis of the immunoprecipitates by polyacrylamide gel electrophoresis revealed that antibodies specific to DEN4 NS1 (a protein encoded by the chimeric virus) were readily detected, but antibodies to TBEV E were either of low titer or were not detectable. Presumably since mice are not a natural host for TBEV, peripheral inoculation of mice permitted only low level viral replication.

Mice that survived IP or ID inoculation of vTBE(ME)/DEN4 were studied for evidence of resistance to subsequent lethal TBEV challenge. Twenty-one days after inoculation with vTBE(ME)/DEN4 or DEN4 virus, mice were challenged IP with $10^3$ LD$_{50}$ of the highly neurovirulent Sofjin strain of TBEV. The mice that survived IP or ID inoculation with chimeric vTBE(ME)/DEN4 were protected against subsequent challenge, whereas all three groups of mice previously immunized with DEN4 died between day 11 and day 20 (see FIG. 21). These results indicated that the virus as a vaccine is protective and specific for TBEV infection. Nonimmunized control mice died of encephalitis between day 10 and day 16 following TBEV infection. TBE(ME)/

DEN4 virus uniformly caused encephalitis in both suckling and adult mice following intracerebral inoculation, whereas mice inoculated with DEN4 developed dengue virus-associated disease with low frequency. Thus, the chimeric virus retains the mouse neurovirulence of TBEV from which its preM and E genes were derived. This indicates that most, if not all, of the genetic determinants of TBEV mouse neurovirulence map within these two structural protein genes. However, unlike parental TBEV, vTBE(ME)/DEN4 was not pathogenic when adult mice were inoculated peripherally, indicating a loss of neuroinvasiveness by peripheral inoculation. These findings suggest that a region of the TBEV genome other than the preM and E genes is required for TBEV to invade the CNS and produce encephalitis. Mice inoculated peripherally with vTBE(ME)/DEN4 were protected against subsequent intraperitoneal challenge with a lethal dose of TBEV, whereas mice similarly inoculated with DEN4 were not. These findings indicate that the preM (precursor of M), M and/or E proteins of vTBE(ME)/DEN4 contain major antigenic determinants for protective immunity against TBEV encephalitis in mice.

Modifying Neurovirulence of Chimeric TBEV (ME)/DEN4

As described in the section above entitled "Mutations in the Dengue Genome Affecting Neurovirulence", the recombinant dengue virus construct was modified by site-directed mutagenesis or mutagenesis by PCR or the like to produce a modified virus suitable for vaccination because of its reduced neurovirulence characteristics. The vTBEV/DEN4 genome can be modified using similar techniques, as disclosed herein, to obtain reduced neurovirulence and thereby improving the safety of an attenuated virus vaccine for TBEV.

Success in constructing a viable TBEV/DEN4 chimera that retains the protective antigens of TBEV, but lacks the peripheral invasiveness of TBEV, provides the basis for pursuing a novel strategy for immunoprophylaxis of this important pathogen, namely the development of an attenuated TBEV vaccine. However, before this goal can be realized, an additional modification of the chimera must be achieved, namely ablation of neurovirulence for the CNS as measured by direct inoculation of virus into the brain. Since the TBEV/DEN4 chimera retains the neurovirulence of its TBEV parent, it was necessary to abolish this property by engineering strategic mutations in the DEN4 or TBEV portion of the chimeric genome and evaluating their effect on mouse neurovirulence. These mutants can potentially include mutations introduced at any number of locations in the viral genome. Initial studies have assessed chimeric viruses with the following mutations: (1) deletions in the 5' noncoding region, (2) mutations that ablate the preM-to-M cleavage site or the glycosylation sites of preM, or E, or NS1 protein, or (3) point mutations in the E gene. Mutations tested to date are included in FIG. 23.

As part of a study to systematically modify the TBE(ME)/DEN4 construct and test for the effect of the genetic alterations on neurovirulence, six different constructs containing one or more changes in the protein sequence were prepared see Example 22. It will be understood that using the techniques provided in this invention, one with skill in the art can create any number of substitutions, additions or deletions to the TBE(ME)/DEN4 construct and test for changes in neurovirulence. Similarly, one with skill in the art can readily combine the mutations provided in FIG. 23 with these or other mutations to test the chimeric construct having preferably at least one alteration in the genetic composition as compared with the chimeric construct combining native sequences.

In studies to assess the ability of the mutant constructs to direct the production of mutant chimeric virus, six mutant chimeras were recovered from the transfected LLC-MK$_2$ cells and the viruses were analyzed for changes in plaque morphology. The progeny of mutant TBE(ME)/DEN4 viruses were amplified by passage in LLC-MK$_2$ cells and analyzed by plaque assay on LLC-MK$_2$ cells or on mosquito C6/36 cells. Chimera TBE(CME)/DEN4, which included all three structural protein genes of TBEV, was similarly analyzed. Wild type DEN4 was also used as a control. As shown in FIG. 23, the plaque size of most mutants on either cell line was reduced as compared to the viral plaques of parental TBE(ME)/DEN4 suggesting that these mutants were restricted for viral replication. Mutants which contained a defective glycosylation site in E or NS1 produced plaques smallest in size among the series of mutants tested.

The mutant chimeric constructs were additionally tested for neurovirulence in mice. Mice were inoculated with the virus as described in Example 21 and described in Example 23. Infected mice were observed for signs of encephalitis and death over 31 days. Constructs containing the *NS1(1)-Glc$^-$ and *PreM/M$^-$ mutations exhibited an LD50 greater than 1000 pfu indicating that these mutants exhibited a greater than 1000-fold reduction in mouse neurovirulence. This finding indicates that the NS1 (1)-Glc$^-$, PreM/M$^-$ or both mutations could be used to confer attenuation of mouse neurovirulence. This findings suggest that similar mutations may also be employed to confer attenuation of other encephalitic flaviviruses including Japanese Encephalitis Virus.

It is further contemplated that those chimeric constructs showing reducing neurovirulence in mice as, evidenced by increased LD$_{50}$ values, are next tested in primates. Example 24 provides a testing scheme for vaccine efficacy in primates. Following successful primate studies the vaccines of this invention are tested in clinical trials in humans. Those with skill in the art can modify the primate studies to make them suitable for human study.

Therefore, the inventions of this application provide a number of vaccines and teach one with skill in the art to prepare chimeric dengue virus vaccines to generate protective immune responses to the serotypes of dengue virus or to other flaviviruses. Such a vaccine preparation can preferably contain a pool of chimeric viruses each expressing structural protein for at least one dengue virus. Using the techniques disclosed herein, one with skill in the art of virology and molecular biology can generate chimeric viruses that incorporate structural regions of one flavivirus with nonstructural regions of a second flavivirus. Preferably, this second flavivirus in a dengue virus and still more preferably, this second virus is dengue type 4 virus. In addition, this invention teaches one with skill in the art to modify the dengue virus construct using site-directed mutagenesis or the like to produce an improved dengue virus vaccine and it is contemplated that these modifications can similarly be incorporated into the chimeric virus construct. The invention also teaches the preparation and testing of chimeric viruses that include non-structural regions and at least one structural region of a dengue virus in combination with structural gene regions from another flavivirus. In particular a vaccine for TBEV is disclosed that is a chimeric virus containing one structural region together with nonstructural regions from dengue 4 and sequences encoding two structural proteins from TBEV.

The encouraging results observed thus far with the TBEV (ME)/DEN4 chimera suggest that these techniques are also useful to produce a vaccine for viruses more closely related to dengue virus than TBEV. One such example is Japanese encephalitis virus which continues to be a major public health problem in the Far East. Thus, in a further embodiment, the techniques of this invention are used to combine the DEN4 cDNA nonstructural regions with at least one structural gene from Japanese encephalitis virus and the remaining structural gene regions of DEN4.

It is further contemplated that other combinations of nonstructural regions and structural regions of different flaviviruses could similarly be prepared and tested using the techniques of this invention. For example, a recombinant construct of Japanese encephalitis virus could be modified to replace one or more structural regions with corresponding gene sequences from tick-borne encephalitis virus while continuing to supply the viral nonstructural regions. Similarly one could generate a recombinant cDNA encoding tick-borne encephalitis virus and replace the structural regions with at least one gene encoding dengue virus structural protein.

All of the publications cited here and in the Examples below are incorporated by reference. Particular embodiments of the invention will be discussed in detail and reference will be made to possible variations within the scope of the invention. There are a variety of alternative techniques and procedures available to those of skill in the art which would similarly permit one to successfully perform the intended invention.

Preparation of Dengue Virus Vaccine

The inventors have constructed a recombinant baculovirus containing a 4.0 kilo-base dengue cDNA sequence that codes for the three virus structural proteins, i.e., capsid (C) protein, pre-matrix (PreM) protein, envelope glycoprotein (E), and nonstructural proteins NS1 and NS2a. Infection of cultured Spodoptera frugiperda cells with this recombinant virus resulted in the production of E and NS1 that were similar in size to the corresponding viral proteins expressed in dengue virus infected simian cells. Other encoded dengue virus proteins such as PreM or C were presumably synthesized. Rabbits immunized with the dengue protein products of the recombinant virus developed antibodies to PreM, E and NS1 although the titers were low, especially to PreM and E. Nevertheless, the dengue antigens produced by the recombinant virus induced resistance in mice to fatal dengue viral encephalitis.

The inventors constructed a full-length DNA copy of the dengue type 4 viral RNA genome. Analysis of the complete sequence revealed that the entire genome is 10,644 nucleotides in length and 96 percent of the genetic information is used to code for a single polyprotein of 3386 amino acids which is translated from a single long open reading frame. This polyprotein is apparently cleaved by proteolytic processing to generate individual viral proteins. The three structural proteins, C-M-E, are located at the amino terminus of the polyprotein, while nonstructural proteins NS1–NS2a–N2b–NS3–NS4a–NS4b–NS5 are at the carboxy-terminus. Intracellular virions lack the M protein, but instead contain a precursor glycoprotein, designated PreM, that is not found in mature virions. Because proteolytic processing is involved in the expression of dengue viral genes, we initially attempted to express the three structural proteins, i.e., capsid (C), membrane (M) (or its precursor (Pre M)) and envelope glycoprotein (E), as well as the nonstructural protein NS1 from a single 5-terminal fragment of cloned dengue DNA using vaccinia virus as a vector. During this study it was observed that: (a) the three dengue glycoproteins, i.e., Pre M, E and NS1, were produced in recombinant vaccinia virus-infected cells and (b) their glycosylation patterns was similar to that observed during dengue virus infection. Infection of cotton rats with the vaccinia recombinant induced a poor immune response to the NS1 glycoprotein (only 1 of 11 animals developed detectable antibodies), while antibodies for the other two glycoproteins were not detected at all. In this instance it appeared that poor immunogenicity of the recombinant vaccinia virus was due wholly or in part to the low level at which dengue viral proteins were expressed. In order to achieve expression of the dengue structural proteins, as well as NS1, at a higher level than occurred with the vaccinia virus-dengue recombinant the inventors turned to the high yielding baculovirus-insect cell system recently developed by M. Summers and his colleagues.

Cells and Viruses

Simian derived $LLC-Mk_2$ cells were grown in Eagle's minimum essential medium supplemented with 10 percent fetal calf serum were used to grow suspensions of dengue type 4 virus (strain 814669). Infection was initiated with 1 pfu/cell and cultures were incubated at 37° C. for 72 hours prior to labeling with $^{35}S$-methionine for preparation of dengue protein markers.

Moth (Spodopertera frugiperda) Sf9 cells obtained from ATCC were grown in Grace's insect cell medium supplemented with 0.3 percent lactalbumin hydrolysate. Wild type baculovirus (ACNPV) was kindly provided by M. Summers (College Station, Tex.). Baculovirus suspensions were prepared in monolayers of moth Sf9 cells that were infected with wild type baculovirus or recombinant baculovirus at low multiplicity (less than 1 pfu/cell).

Construction of Baculorvirus-dengue Recombinant

Genomic DNA of the wild type or recombinant baculovirus was prepared from extracellular virus according to the procedure described by Summers and Smith. The construction of plasmid DNA containing a full length dengue sequence was described earlier. The intermediate baculovirus cloning vector, pAC373, was kindly provided by M. Summers. The 4.0 Kb BgIII fragment of dengue C-preM-E-NS1–NS2a sequence was inserted into the unique Bam HI site of the intermediate baculovirus vector which positioned the first AUG of the dengue sequences 25 nucleotides downstream of a polyhedrin non-coding sequence (FIG. 24). Sf9 cells were then transfected with a mixture of baculovirus DNA (2 ug) and intermediate vector recombinant DNA (10 ug) in a calcium phosphate precipitate. The transfected cells were then incubated at 29° C. for 6 to 7 days at which time greater than 90 percent cells showed accumulation of the polyhedrin protein. Recombinant baculovirus was enriched from the progeny virus population using dot hybridization with a labeled dengue cDNA probe in conjunction with limit dilution purification and passage in Sf9 cells. This procedure was repeated three times. The recombinant virus was further purified by serial plaque passage on Sf9 cells.

Indirect Immunofluorescence Assay

Confluent Sf9 cells grown on a chamber slide were infected with wild type baculovirus or recombinant virus at approximately 1 pfu/cell and incubated at 29° C. for 3 days. Medium was removed and cells were rinsed with phosphate buffered saline (PBS) and then fixed with cold acetone. Three dengue type 4 virus monoclonal antibodies, kindly provided by M.D. Gentry (WRAIR, Washington, D.C.), were used to detect expression of dengue viral protein; 4H9(PreM-specific), 1 H10(E-specific), and 1G6 (NS1-specific). Monoclonal antibody at a dilution of 1:50 was incubated with the infected monolayer and excess antibody was then rinsed off with PBS. Fluorescein labeled rabbit anti-mouse serum at a 1:50 dilution was then incubated with the cell monolayer. The slides were then washed and examined using a fluorescence microscope.

Southern Blot Analysis of Baculovirus Recombinant DNA

Genomic DNA (1 ug) of recombinant baculovirus or intermediate plasmid DNA (0.1 ug) were each digested with restriction endonucleases as specified by the commercial suppliers. The digests were separated on a 1 percent agarose gel, blotted on nitrocellulose paper, and probed with a $^{32}$P-labeled oligonucleotide representing nucleotides 1303–1326 of the dengue sequence.

Analysis of Dengue Proteins

Three days after infection with 10 pfu/cell of recombinant or wild type baculovirus, $10^6$ Sf9 cells were lysed in a 0.5 ml RIPA buffer (0.01M Tris, pH 7.5, 1 percent deoxycholate, 1 percent triton, 0.1 percent SDS and 1 mM PMSF). Cell lysates (60 ul) were separated on 12 percent SDS polyacrylamide gel (acrylamide :bis=60:1.6) for 16 hours at 80 volts in buffer containing 25 mM Tris, pH 8.0, 0.2M glycine, and 0.1 percent SDS. Protein bands in the polyacrylamide gel were transferred electrophoretically onto nitrocellulose paper. The nitrocellulose blot was then reacted with 1:200 dilution of dengue E-specific antiserum raised in rabbits against a synthetic E oligopeptide (amino acid numbers 260–273). Radioactive $^{125}$I-labeled protein A was then used for detection of the dengue E glycoprotein. Metabolic labeling of virus-infected, or uninfected Sf9 cells with $^{35}$S-methionine (100 uCi/ml, specific activity 1100 Ci/mM) was carried out in methionine-free medium for 2 hours. The labeled lysates were then prepared in RIPA buffer for use in immunoprecipitation with dengue-specific mouse hyperimmune polyvalent antiserum or NS1 specific monoclonal antibodies (1G6 and 8E2) kindly provided by M. K. Gentry.

Immunization and Viral Challenge

Rabbits were bled and then inoculated subcutaneously on the upper back with a lysate of $5\times10^6$ recombinant baculovirus-infected Sf9 cells emulsified in Freund's complete adjuvant followed by a second inoculation of the lysate in Freund's incomplete adjuvant two weeks later. One month after the primary inoculation a post-immunization serum specimen was obtained.

Protective efficacy of baculovirus recombinant expressed dengue proteins was evaluated by immunizing 3 week old mice with lysate equivalent to $1.5\times10^6$ recombinant baculovirus-infected cells with or without Freund's complete adjuvant. This material was inoculated again 3 days later and again 14 days later. Control animals received an equivalent lysate of uninfected cells or cells infected with wild type baculovirus (10 pfu/cell) with or without adjuvant. Immunized animals were bled on day 21 and the following day were challenged intracerebrally with 100 $LD_{50}$ ($5\times10^3$ pfu) of dengue type 4 virus (H241). Mice were observed for signs of neurological disease and death during a 3 week period after challenge.

Construction of a Recombinant Baculovirus Expressing Dengue Viral Proteins

Dengue gene expression involves proteolytic cleavage of a polyprotein and hence the inventors sought to express the structural genes at the 5'-terminus of the RNA genome as well as the immediate downstream NS1 gene en bloc. This approach was taken because it had been shown in a previous study of a vaccinia recombinant which contained this region of the dengue genome that post translational processing of these genes occurs in the absence of downstream non-structural genes. The 4.0-Kilobase BglII dengue DNA fragment (nucleotides 88–4128), which encodes the three virus structural proteins (i.e., the capsid (C), pre-matrix (PreM) and envelope (E) proteins), as well as the NS1 nonstructural protein and a portion of NS2a was inserted into the unique BamHI site of the baculovirus cloning vector, pAC373, kindly provided by M. Summers. The dengue sequences in this construct was placed under the transcriptional control of the strong baculovirus polyhedrin promoter. Also, dengue RNA transcripts should contain the authentic dengue virus initiation codon and produce a polyprotein that included the C-PreM (M), E, NS1, NS2a sequence. Recombinant DNA and wild type baculovirus genomic DNA were co-transfected into *Sodoptera frugiperda* (Sf9) cells to generate recombinant baculovirus through homologous recombination. Viral plaques that lacked discernible polyhedrin protein were isolated and purified by further plaque isolation on Sf9 cells.

Analysis of Recombinant Baculovirus DNA

Putative baculovirus recombinants were analyzed to determine whether the 4.0 Kb dengue DNA sequence was stably integrated in the baculovirus genome. Recombinant virus was harvested from the medium of infected cells and viral DNA was then extracted according to the procedure described by Summers and Smith. This DNA was then digested with XhoI and SstI or with XhoI and KpnI. Recombinant plasmid DNA which served as a control, was also digested in the same manner. The digests were separated on an agarose gel and blotted on nitrocellulose paper for probing with a $^{32}$P-labeled dengue cDNA sequence (dengue nucleotides 1303 to 1326). This analysis, shown in FIG. 25 revealed that the predicted 4.0 kilobase (Kb) DNA fragment of XhoI/SstI digest and the 6.6 Kb DNA fragment of XhoI/KpnI digest were present in the recombinant baculovirus DNA. These fragments were similar in size to the corresponding fragments present in the intermediate recombinant vector, indicating that the entire 4.0 Kb dengue DNA fragment was integrated into the desired location of the baculovirus DNA genome. The dengue DNA sequence was thus under the transcriptional control of the polyhedrin promoter that normally directs high level synthesis of polyhedrin protein during baculovirus infection.

Detection of Dengue Proteins Produced by Recombinant Baculovirus.

Dengue-specific antibodies were used in an indirect immunofluorescence assay to detect the synthesis of dengue viral proteins in recombinant baculovirus-infected Sf9 cells. the antibodies used included monoclonal antibody 2H2, specific for Pre M; monoclonal antibody 1H10 specific for dengue type 4 envelope (E) glycoprotein; and monoclonal antibody, 1G6, specific for the NS1 non-structural protein. Recombinant virus infected cells contained antigens which were stained with each of these antibodies, whereas uninfected cells or cells infected with wild type baculovirus were negative (FIG. 26). This indicates that the dengue DNA sequence was transcribed and the resulting mRNA was translated properly to produce dengue proteins. The Pre M, E and NS1 dengue proteins appeared to accumulate within infected cells but were not expressed on their surface as indicated by failure to detect staining of the outer membrane of live infected cells (data not shown).

Analysis of Dengue Protein Products by Radio-immunoassay.

Western blot analysis was employed to identify individual dengue viral proteins in order to determine if the polyprotein was proteolytically cleaved and properly glycosylated in Sf9 cells (FIG. 27A). When lysates from recombinant virus-infected, wild type baculovirus-infected, or uninfected Sf( cells were analyzed with dengue E specific antibodies and $^{125}$I-labeled protein A, a labeled band was observed which had a mobility similar to E produced during dengue virus infection. This suggested that proteolytic cleavage and glycoslation of the dengue envelope glycoprotein expressed by the baculovirus recombinant was normal in moth cells. The recombinant baculovirus also appeared to produce authentic NS1 as indicated by radio-immunoprecipitation of an infected cell lysate using hyperimmune antiserum or NS1 specific monoclonal antibodies (FIG. 27B). Pre M was not detected in recombinant infected cells analyzed with dengue hyperimmune antiserum.

Immunization of Rabbits with a Lysate of Recombinant Baculovirus-infected Cells.

Two rabbits were inoculated with a lysate of baculovirus recombinant-infected cells (5×10$^6$) emulsified in a completed Freund's adjuvant followed by a booster inoculation or the same antigen in complete adjuvant two weeks later. Control animals received a lysate prepared from wild type baculovirus-infected cells. Four weeks after the initial immunization, serum samples were tested for the presence of dengue virus-specific antibodies. Initially, immunoprecipitation of radio-labeled dengue antigens were performed and the precipitates were analyzed on SDS-polyacrylamide gels. Sera from recombinant virus-immunized rabbits specifically precipitated dengue E, NS1 and PreM glycoproteins; the largest concentrations of antibodies appeared to be directed against NS1 (FIG. 28). The developed of dengue antibodies was confirmed by an ELISA utilizing purified dengue 4 virus; the rabbits had a titer of 1:80 to 160. Other serological assays, such as virus neutralization by plaque reduction, hemagglutination-inhibition or complement fixation, were negative and this is consistent with the low titer of serum antibodies measured by ELISA. These observations indicate that rabbits immunized with the protein products of the recombinant virus responded to each of the three dengue glycoproteins; however, the antibody titers were low, especially to Pre M and E.

Resistance of Mice Immunized with Dengue Proteins Expressed by Recombinant Virus The experimental mouse model of dengue disease was employed to determine if dengue viral proteins produced by the baculovirus recombinant induced resistance to development of central nervous system symptoms and death. Mice were immunized subcutaneously with a cell lysate (1.5×10$^6$ cells) with or without Freund's adjuvant. The same material was inoculated again after 3 days and again at 2 weeks. The immunized animals were bled at 3 weeks and then challenged intracerebally with 10$^2$LD$_{50}$ of a homotypic dengue type 4 virus (strain H241). Following challenge, animals were observed for a period of 3 weeks for signs of central nervous system disease and death. Most mice immunized with the lysate of recombinant baculovirus-infected cells were protected against illness and death (Table 1).

TABLE 1

Dengue Type 4 virus Structural Proteins and Non-structural Protein NS$_1$ Expressed by Recombinant Baculovirus Protect Mice Against Dengue Encephalitis

| Mice immunized with | | Response to i.c. challenge with 100 LD$_{50}$ Dengue Type 4 Virus | |
| --- | --- | --- | --- |
| Lysate of SF9 Cells | Adjuvant | Mortality Rate | Morbidity Rate |
| Uninfected | + | 10/10 | 10/10 |
|  | − | 10/10 | 10/10 |
| Baculovirus infected | + | 8/10 | 10/10 |
|  | − | 7/10 | 10/10 |
| Recombinant virus infected† | + | 1/10 | 2/10 |
|  | − | 0/10 | 1/10 |
| Not immunized | − | 5/5 | 5/5 |

*Animals showed symptoms of CNS disease.
†Recombinant dengue-baculovirus produced dengue type 4 virus structural proteins and nonstructural protein NS1.

On the other hand, all animals immunized with a lysate of uninfected cells or baculovirus virus-infected cells developed signs of neurologic illness following challenge and most died. This indicates that dengue antigens produced by the recombinant baculovirus induced resistance to dengue viral encephalitis. Protection was observed whether mice were immunized with a cell lysate of baculovirus recombinant-infected cells administered alone or emulsified in Freund's adjuvant.

Seroresponse of Mice Immunized with Dengue Proteins from Recombinant Baculovirus-infected Cells.

Seroresponse of immunized mice to individual dengue proteins was analyzed by radio-immunoprecipitation of $^{35}$S-methionine labeled dengue antigens (FIG. 29). Sera from mice immunized with recombinant virus-infected cell lysate precipitated dengue NS1 with high efficiency; in contrast to serum antibodies specific for E or PreM were not detected. The lack of a significant antibody response to E was confirmed by the inventors' failure to detect neutralizing antibodies in the serum of immunized mice.

The 4.0 Kb dengue DNA sequence that codes for the three structural proteins and nonstructural proteins NS1 and NS2a in one open reading frame was inserted into the baculovirus genome under the control of the polyhedrin promoter for expression of the dengue proteins in insect cells. The resulting recombinants baculovirus appeared to be stable. Insect cells infected with this recombinant virus produced dengue E and NS1 glycoproteins similar in size to the corresponding glycoproteins produced in dengue virus-infected cells, suggesting that proteolytic processing of the dengue polyprotein to generate these dengue proteins was normal. Their similarity of molecular size to authentic viral glycoproteins further suggests that these expressed products were glycosylated in insect cells. Thus, the expression and processing of dengue E and NS1 glycoproteins in insect cells appears to be similar to that observed during dengue virus infection of simian cells.

In recent studies it was shown that the level of expression of foreign genes by a baculovirus vector is affected by the 5'-noncoding region of the polyhedrin gene sequence upstream of the foreign gene insert. For example, vector pAC373 (cloning site at –9) expresses foreign DNA at a higher level than vector pAC380 (cloning site at –59). Expression of dengue genes by the baculovirus vector pAC373 appeared to be comparable to that obtained by other workers with this vector. Recently, several in-phase vectors that contain the entire noncoding sequence of the polyhedrin N-terminal sequence have been developed. These vectors express foreign genes as fusion proteins with unusually high efficiency (K. L. Coelingh, personal comm.). The use of these new vectors may allow us to achieve higher levels of dengue gene expression.

Previously, it was observed that the dengue proteins expressed by an infectious recombinant vaccinia virus induced a very poor immune response to the NS1 glycoprotein and failed to elicit antibodies to the E or PreM glycoprotein. In contrast, the dengue antigens expressed in the baculovirus-insect cell system were able to induce a definite antibody response to all three glycoproteins following immunization of rabbits although the titer of antibodies to these antigens was low compared to hyperimmune mouse antiserum. Nonetheless, immunization of mice with a crude lysate of recombinant baculovirus infected-cells induced significant resistance to experimental dengue virus encephalitis. Although all the dengue virus structural proteins and NS1 were present in the lysate, only the dengue E glycoprotein and the nonstructural glycoprotein NS1 would be expected to play a role in prevention of disease. Serological analysis of post immunization sera by viral neutralization or radio-immunoprecipitation indicated that mice developed little or no response to the E glycoprotein. On the other hand, antibodies specific to the NS1 were detectable in relatively high concentration. The observation that little or no virus neutralizing activity was detectable in mouse sera prior to virus challenge raises the possibility that mechanisms other than viral neutralization were responsible for the observed protection. This suggests that the active protective antigen present in the baculovirus recombinant lysate was NS1. In this regard, the results are similar to those obtained in recent studies in which immunization of mice with purified NS1 of yellow fever virus or dengue virus induced resistance to challenge by the respective virus.

There is some concern above the use of dengue envelope glycoprotein for immunization against dengue disease because antibodies to E can produce antibody-dependent enhancement of replication of heterotypic dengue virus replication in macrophages in culture. This is thought to occur by attachment of the E-immunoglobulin complex to Fc receptors on macrophages thereby facilitating virus uptake. A similar concern does not apply to NS1 because this viral glycoprotein is expressed on the surface of infected cells but is not present in or on dengue virions. In this circumstance, antibody dependent enhancement of dengue virus replication in macrophages would not be expected to occur following immunization with NS1.

Recently an increase in expression of the B1gII dengue sequence (i.e., C-PreM-E-NS1–NS2a) was achieved using the new more efficient baculovirus fusion vectors. In addition, efforts have been initiated to purify dengue viral proteins from the lysate of recombinant virus-infected cells.

Recently, expression of a single dengue protective antigen, either dengue E glycoprotein or nonstructural protein NS1, was achieved using the baculovirus-insect cell system. In these studies an N-terminal sequence (amino acids 1–70) of the respiratory syncytial virus (RSV) G glycoprotein was fused with the complete dengue protein sequences. In addition, a dimer form of the SV-NS1 fusion protein, similar to the dimer of NS1 produced during dengue virus infection, was expressed. Most important of all, immunization of mice with either RSVG-E, or RSVG-NS1 induced complete resistance to dengue virus challenge. These results established in an unambiguous manner that the dengue E and dengue NS1 are each a protective antigen. Either antigen produced by a baculovirus recombinant is able to induce complete resistance to lethal intracerebral challenge with dengue virus. Furthermore, these results establish the feasibility of using either antigen or both antigens expressed by baculovirus recombinant(s) for the prevent of dengue disease. Incorporation of E and/or NS1 of each of the 4 dengue virus serotypes will be required for complete protection against the range of antigenic variants of dengue virus known to cause disease in man. The strategy used to achieve successful resistance to dengue virus disease as incorporated in this invention is also applicable to the other flaviviruses of major public health importance such as Japanese B encephalitis virus and the tick-borne encephalitis viruses because all flaviviruses have the same genome organization and express their proteins by the same mechanism. Recently, in collaboration with Dr. Dennis Trent, CDC, Fort Collins, CO., Japanese B encephalitis virus cDNA sequences coding for the 3 structural proteins and non-structural proteins NS1 and NS2a have been successfully expressed in a baculovirus recombinant similar to that described above for dengue virus. In addition, the 3 structural proteins (C-M-E) were expressed in a baculovirus recombinant. Also, the NS1–NS2a of Japanese B encephalitis virus were similarly expressed in a baculovirus recombinant.

EXAMPLES AND GENERAL INFORMATION RELATING THERETO

Viruses: Dengue type 4 virus strain 814669 was used for construction of full-length cDNA that served as the source of full-length infectious RNA transcripts (Mackow, E. et al. (1 987) *Virology* 159, 217–228; Zhao, B. et al. (1 986) *Virology* 155, 77–88). A preparation of dengue type 1 virus Western Pacific strain (D1 WP), a fetal rhesus lung cell passage level 9, was kindly provided by Dr. K. Eckels (WRAIR, Washington, DC) (McKee, K. T. et al. (1987) *Am. J. Trop. Med. Hyg.* 36, 435–442). A mouse brain preparation of mouse neurovirulent dengue type 2 virus New Guinea C strain (D2 NGC), mouse brain passage level 38, was kindly provided by Dr. D. Dubois (WRAIR, Washington, D.C) (Sabin, A. B. (1952) *Amer. J. Trop. Med. Hyg.* 1, 30–50). Dengue 1 and dengue 2 viruses were amplified by one passage in C6/36 mosquito cells. Each of these three viruses was then passaged once in LLC-MK$_2$ simian kidney cells, and the resulting virus suspension was used to study plaque morphology and mouse neurovirulence.

Cloning Vectors: Plasmid p5'-2, which contains the 5'-half of the dengue 4 genome cDNA, was modified to facilitate replacement of the three structural protein genes (Lai, C. J. et al. (1991) *Proc. Natl. Acad. Sci. USA* 88, 5139–5143). First, a unique Xho I site was introduced through site-directed mutagenesis at nucleotide 2342 (A-G) of the dengue 4 sequence, near the 3' end of E, creating p5' -2 (Xho I). This nucleotide change did not alter the amino acid sequence. This vector was then digested at the unique Bst BI site within the dengue sequence and at the unique Asp 718 site which immediately follows the dengue sequence in p5'-2, and the fragment was ligated to the 3' half of the dengue 4 genome, creating full-length p2A (Xho I). Second, the Bgl II site at nucleotide 88, which is conserved among flaviviruses, was made unique by removing three other Bgl II sites in p5'-2. The Bal II site at the junction between pBR322 and the SP6 promoter was removed by inserting a Not I linker. Two other sites at 4128 and 4277 were removed by shortening the vector to the recently introduced Pst I site at 3473 (McKee, K. T. et al. (1987) *Am. J. Trop. Med. Hyg.* 36, 435–442). Plasmid p5'-2 (Xho I, Pst I) was subsequently used for fragment exchange to create chimeric cDNA.

Figure 1:
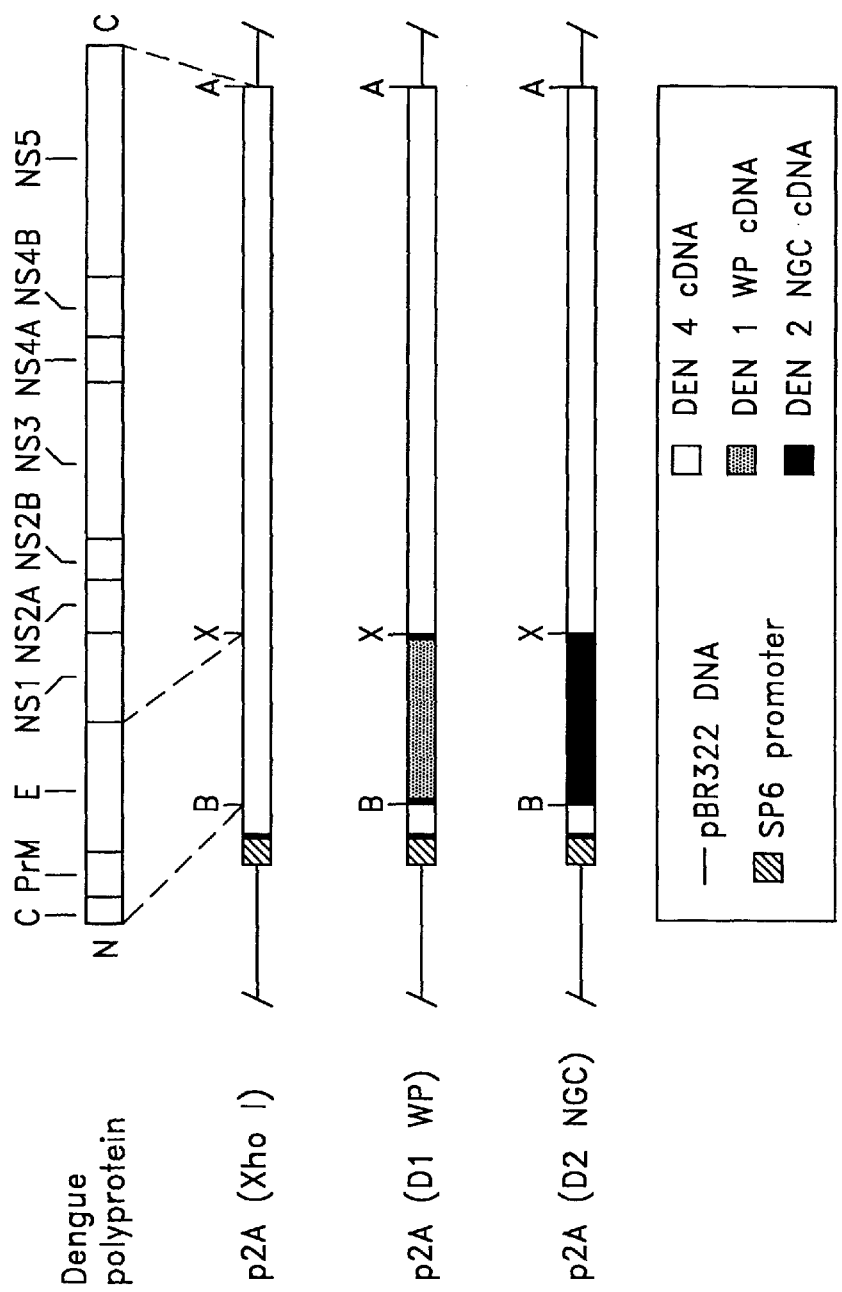
FIG. 1. Structure of full-length dengue virus cDNAs used for preparation of chimeric dengue viruses.

FIG. 1 presents the following plasmids containing full-length dengue cDNA which were constructed: p2A (Xho I), a complete cDNA copy of the dengue 4 genome, in which a unique Xho I site was created near the 3' end of the E gene; p2A (D1 WP), derived from p2A (Xho I) by replacing the sequence between the Bgl II site in the 5' non-coding region and the unique Xho I site with the corresponding cDNA of dengue 1 Western Pacific strain; p2A (D2 NGC), prepared in the same manner by replacing the BgI II-Xho I fragment with the corresponding cDNA from dengue 2 New Guinea C strain. B: BgI II; X: Xho I; A: Asp 718 restriction enzyme sites.

Chimeric cDNA: Dengue type 1 or type 2 virus grown in C6/36 mosquito cells was purified and virion RNA extracted according to the procedure described by (Zhao, B. et al. (1986) (*Virology* 155, 77–88). Dengue I first-strand cDNA was synthesized by reverse transcription using a negative-sense oligonucleotide which hybridized to nucleotides 2306–2338 of the dengue 1 sequence. This primer sequence contained a silent third base change (A-G) at nucleotide 2316 to create an Xho I site at the position corresponding to the site in the dengue 4 E gene in p5' -2 (Xho I, Pst I) described above. The dengue 1 cDNA was then used as the template to synthesize double-stranded DNA by PCR, using the negative-sense oligonucleotide and a positive-sense primer which hybridized to dengue 1 nucleotides 51–70, and contained the conserved BgI II site. The PCR product was digested with BgI II and Xho I, and then cloned into p5'-2 (Xho I, Pst I), replacing the corresponding dengue 4 sequence. The CIa I-Xho I fragment containing the dengue 1 sequence was then joined with the remaining dengue 4 cDNA from p2A (Xho I) to create full-length chimera p2A (D1 WP). Similarly, dengue 2 first-strand cDNA was synthesized using a negative sense primer that hybridized to dengue 2 nucleotides 2310–2364. This primer contains three base changes: T-C at 2333, A-G at 2336, and C-A at 2337. These changes create an Xho I site at the position corresponding to the Xho I site in the dengue 4 E gene described above. These changes did not alter the amino acid sequence. For double strand DNA synthesis by PCR, the negative-sense primer was used, and the positive-sense primer was the same used for dengue 1. The PCR product was digested with BgI II and Xho I, cloned into p5'-2 (Xho I), and the CIa I-Xho I fragment was used to replace the corresponding fragment of p2A (Xho I) to create p2A (D2 NGC).

RNA Transcridtion, Transfection and Recovery of Virus: Transfection of cells with full-length RNA transcripts was performed as described (Lai, C. J. et al. (1991) *Proc. Natl. Acad. Sci. USA* 88, 5139–5143). Ten days after transfection, cells were trypsinized and transferred to a 6-well plate and to a chamber slide. Two days later, cells on the slide were tested by immunofluorescence (IFA) for evidence of dengue viral antigens. If IFA showed that most cells was infected, the cells in the 6-well plate were trypsinized, mixed with a 6-fold excess of uninfected cells, and incubated until cytopathic effects (appearance of numerous dead cells in the medium) became evidence, usually after 6–7 days. The infected cells were then harvested by removing the medium, scraping the cells, resuspending them in a standard volume of 50% Eagle's minimal essential medium/50% serum, and then freezing. On the other hand, if a small percentage of cells was positive, the cells were trypsinized, diluted 1:3 in fresh medium, and allowed to grow without addition of uninfected cells. The percentage of infected cells was then estimated on a weekly basis, and cell lysates were harvested and titered for virus at intervals.

Detection of Dengue Virus Antigens: Infected cells were analyzed by IFA using serotype-specific monoclonal antibodies (mab) 1F1 (dengue 1), 3M5 (dengue 2), 5D4 (dengue 3) and 1H10 (dengue 4) and NS1-specific mab 1G6 (dengue 4), originally produced by Dr. M. K. Gentry and Dr. E. Henchal (WRAIR, Washington D.C) (Henchal, E. A. et al. (1982) *Am. J. Trop. Med. Hyg.* 31, 548–555). Monoclonal antibodies were used at a dilution of 1:50–1:300, while fluorescein-conjugated anti-mouse antiserum (Kierkegaard-Perry Laboratories, Gaithersburg, Md.) was used at 1:100. Results were recorded photographically; for each mab, infected cells yielding a negative result were photographed for the same exposure time as positive cells. To analyze proteins of parental (wild-type) dengue viruses and of progeny virus v2A (Xho I), confluent LLC-$MK_2$ cells in a 6-well plate were infected with virus at an MOI of 0.2. Six days after infection, cells were labeled with 50$\mu$Ci/well of S-methionine-free medium for 6 hours and cells were then lysed with RIPA buffer. For chimeric virus v2A (D1 WP), labeling was performed when approximately 100% of the cells were infected, while v2A (D2 NGC), labeling was performed when about 30% were infected. Lysates were precipitated with the appropriate homotypic or heterotypic hyperimmune mouse ascitic fluid (HMAF) and analyzed by electrophoresis on SDS-12% polyacrylamide gels.

Plague Morpholoay: Viruses were characterized for plaque morphology on LLC-$MK_2$ cells (Bancroft, W. H. et al. (1979) *Pan Am. Hlth. Org. Sci. Publ.* 375, 175–178). Each parental virus was passaged once in LLC-$MK_2$ cells prior to analysis of plaque morphology. Neutral red overlay was added to cultures after 6–9 days of incubation.

Evaluation of Chimeric Viruses in Suckling Mice: Three-day old Swiss mice were inoculated intracerebrally with 2000 pfu of parental or chimeric dengue virus, in the form of a diluted lysate of virus-infected LLC-$MK_2$ cells. Negative control mice were injected with a lysate of uninfected cells. One liter was inoculated with parental dengue type 4 virus (814669), dengue type 1 virus WP, or dengue type 2 virus NGC. Two liters were inoculated with v2A (Xho I), v2A (D1 WP), or v2A (D2 NGC). Inoculated mice were monitored for 21 days for signs of encephalitis and for death.

Example 1

Chimeric cDNA & Viruses

The full-length dengue type 4 virus cDNA (p2A) was used to construct chimeric viruses in which its structural gene sequences were replaced by the corresponding sequences of a dengue type 1 or type 2 virus. The type 1 virus (WP) chosen for this purpose was a low tissue culture passage strain that had not been adapted to growth in mouse brain. The type 2 strain (NGC) was a highly neurovirulent mutant that had been selected during serial intracerebral passage in mice. The type 2 mutant was chosen for this study because it offered the possibility of mapping the genetic determinants of mouse neurovirulence.

Transformation of *E. coli* strain HD1528 bacteria with plasmid constructs p2A (Xho I), p2A (D1 WP) or p2A (D2 NGC) produced a stable plasmid population. The predicted structure of these plasmids is shown in FIG. 1. Their structure was verified by restriction enzyme mapping.

Approximately one-half of the LLC-$MK_2$ cells transfected with RNA transcripts from p2A (Xho I) were positive by immunofluorescence staining for dengue virus antigens on day 12 (FIG. 2A).

FIG. 2 presents (A) LLC-$MK_2$ cells transfected with the same concentration of RNA transcripts from p2A (Xho I), p2A (D1W), or p2A (D2 NGC). Percentage of virus-infected cells following transfection was estimated by IFA after replating in fresh medium. (B) Infected cells were harvested when a majority of cells was positive by IFA. Titration of virus was performed by plaque assay (Bancroft, W. H. et al. (1979) *Pan Am. Hlth. Org. Sci. Publ.* 375, 175–178).

Figure 2A:
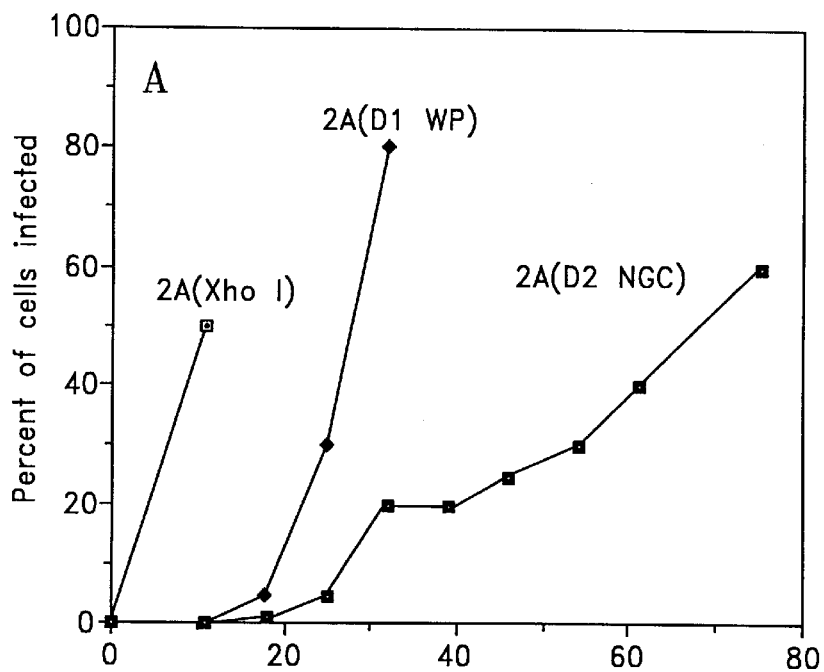
FIGS. 2A, 2B. Percentage of virus infected cells and titer of virus following transfection with RNA transcripts.
Figure 2B:
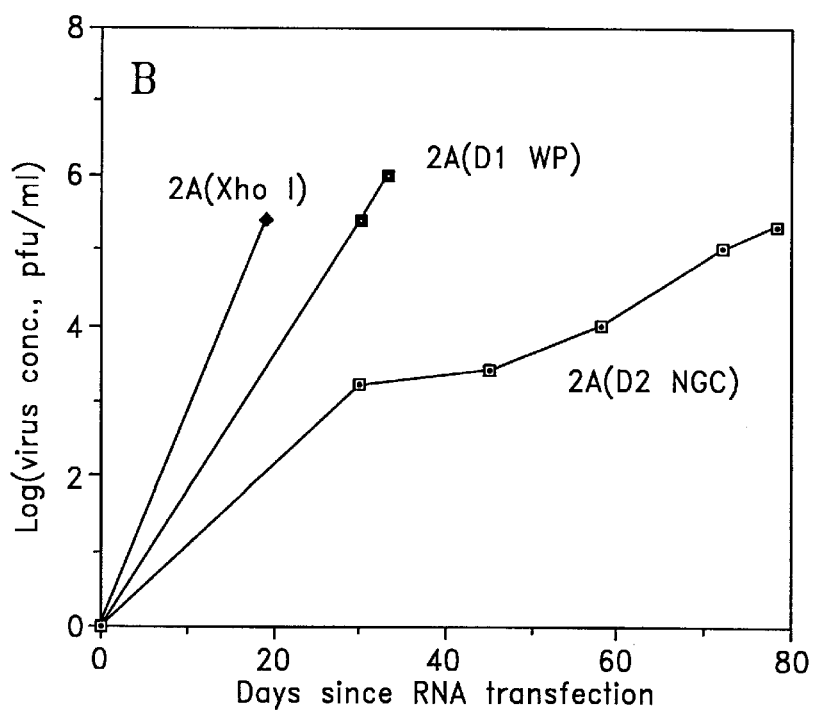
Figure 3:
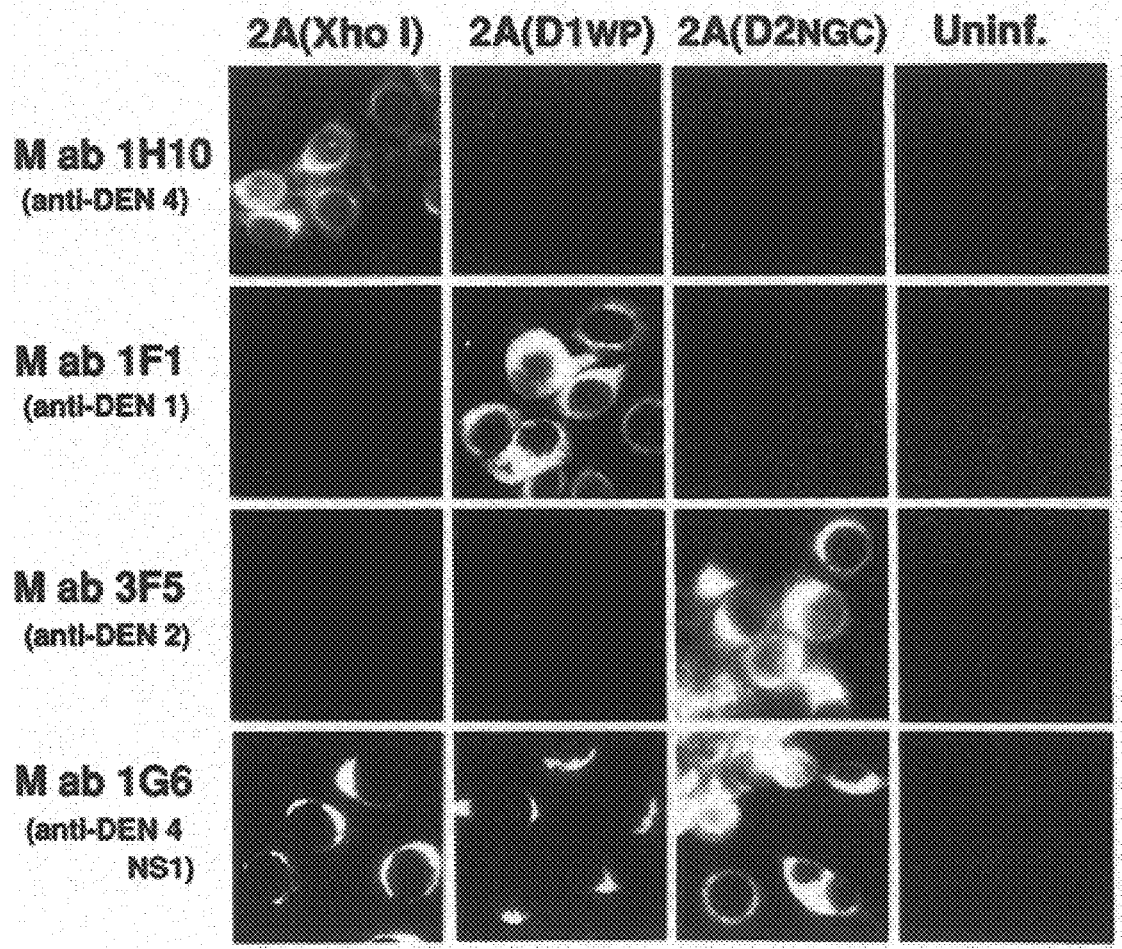
FIG. 3. Serotype analysis of chimeric dengue viruses.

In a previous study, a similar proportion of antigen positive cells, in the range of 20–50%, was observed 12 days after transfection with transcripts from p2A and p2A (Pst I), which in both instances yielded virus with wild-type phenotype (Lai, C. J. et al. (1991) *Proc. Natl. Acad. Sci. USA* 88, 5139–5143). In contrast, on day 12 less than 1% of cells transfected with transcripts from p2A (D1 WP) or p2A (D2 NGC) were positive. The percentage of cells infected with v2A (D1 WP) increased to approximately 5% by day 19, 30% by day 26, and 80% by day 33, at which time the titer of virus present in transfected cells was $5 \times 10^6$ pfu/ml. (FIGS. 2A and 2B). In contrast, v2A (D2 NGC) grew more slowly: we estimated that 1% of cells were positive on day 19, but less than a third of the cells had become infected by day 54. The virus titer was only $1.5 \times 10^2$ pfu/ml at 30 days, $2.5 \times 10^2$ at 44 days, and it did not reach $10^4$ pfu/ml until day 58. At 72 days after transfection, a majority of cells were infected, and the titer of the cell suspension was found to be $10^2$ pfu/ml.

The titer of virus produced by cells transfected with p2A (Xho I) RNA transcripts ($10^6$ pfu/ml) was the same as that observed when cell cultures were infected with type 4 virus at an MOI of 0.1. In addition, the highest titer of virus produced by cultures transfected with the type 1/type 4 chimera ($5 \times 10^6$ pfu/ml) was similar to that observed following infection of cell cultures with type 1 virus at an MOI of 0.1 ($1.5 \times 10^7$ pfu/ml). The highest titer of the type 2/type 4 chimera produced following transfection ($10^2$ pfu/ml) was similar to that produced by cell cultures infected with its type 2 parent at an MOI of 0.5.

Example 2

Characterization of Chimeric Structural Proteins

Indirect immunofluorescence was performed to characterize progeny viruses, as shown in FIG. 3.

FIG. 3 presents immunofluorescence assay performed on LLC-$MK_2$ cells infected with v2A (Xho I), v2A (D1 WP), or v2A (D2 NGC), or on uninfected cells. Monoclonal antibodies were used at dilutions of 1:50–1:300, while fluorescein-conjugated anti-mouse antibody was used at 1:100. The serotype specificity of the monoclonal antibodies is shown at left.

Cells infected with v2A (Xho I) were stained with dengue 4 specific mab 1H10 by IFA, but did not bind dengue 1 specific mab 1 Fl or dengue 2 specific mab 3M5. As predicted, cells infected with v2A (D1 WP) reacted only with 1F1, and those infected with v2A (D2 NGC) were stained only with 3H5. Mab 5D4, specific for dengue 3 virus, did not react with any of the infected cells. These results indicated that both chimeric viruses exhibited the antigenicity specified by their structural protein genes. As expected, Mab 1G5, specific for dengue 4 non-structural protein NS1, stained cells infected by progeny of the dengue type 4 cDNA, i.e., 2A (Xho I), as well as either of the chimeric viruses, 2A (D1 WP) or 2A (D2 NGC) derived from the type 4 virus.

The proteins of parental dengue type 4 virus and of its cDNA-derived progeny v2A (Xho I) appeared to be identical when analyzed by immunoprecipitation with homotypic HMAF followed by polyacrylamide gel electrophoresis (FIG. 4). FIG. 4 presents $^{35}$S-methionine-labeled lysates of virus-infected LLC-$MK_2$ cells or uninfected control cells were immunoprecipitated with hyperimmune mouse ascitic fluid (HMAF) raised against dengue 1, 2 or 4, and analyzed by electrophoresis on an SDS-12% polyacrylamide gel (acrylamide:bis=60:1.6). At the top of each lane, virus is indicated vertically, while the HMAF with which the lysate was immunoprecipitated is indicated horizontally. Markers: protein molecular size markers are in kilodaltons. The locations of the E and pre-M glycoproteins of dengue 1, 2 and 4 are indicated (FIG. 4).

The proteins of parental dengue type 1 virus (WP) and of dengue type 2 virus (NGC) were also analyzed. The E glycoproteins of dengue 1 and dengue 2 co-migrated, but they migrated more slowly than the E protein of dengue 4. Similarly, the pre-M glycoproteins of dengue 1 and 2 comigrated, but they also migrated more slowly than the pre-M of dengue 4. The difference in relative molecular size of the E proteins was approximately 4 kd, while that of the pre-M proteins was about 1 kd. These differences in molecular size of E and pre-M were probably due to variation in the extent of glycosylation or conformational differences. The immunoprecipitated proteins of viruses v2A (D1 WP) and v2A (D2 NGC) showed a hybrid pattern. Pre-M and E of v2A (D1 WP), immunoprecipitated with dengue 1 HMAF, co-migrated with pre-M and E of parental dengue 1, but dengue 4 HMAF precipitated only bands which co-migrated with dengue 4 non-structural proteins. Similarly, pre-M and E of parental dengue 2, while dengue 4 HMAF precipitated non-structural proteins resembling those of type 4 virus.

Parental dengue type 4 virus and its cDNA-derived progeny v2A (Xho I) produced similar plaques on LLC-$MK_2$ cells (not shown). The plaques of parental viruses were clearly visible when stained with neutral red six days after infection, but chimera v2A (D2 NGC) failed to produce detectable plaques at that time. If staining was delayed until day 9, however, very small v2A (D2 NGC) plaques were detected, much smaller than those of v2A (Xho I) or wild-type dengue 2 NGC (FIG. 5). Plaques of dengue 4 814669 did not differ from those of progeny virus v2A (Xho I). Plaques of v2A (D1 WP) were basically similar to those of v2A (Xho I).

FIG. 5 presents monolayers of LLC-$MK_2$ cells infected differ from those of progeny virus v2A (Xho I). Plaques of v2A (D1 WP) were basically similar to those of v22A (Xho I).

FIG. 5 presents monolayers of LLC-$MK_2$ cells infected with dengue virus, followed by an agarose overlay (Bancroft, W. H. et al. (1979) *Pan Am. Hlth. Org. Sci. Publ.* 375, 175–178). Neutral red overlay was applied 9 days after infection of the cell monolayer, and plaques were photographed the next day. A: 2A (Xho I); B: 2A (D1 NGC); C: wild-type NGC dengue 3.

Example 3

Virulence of Viruses for Suckling Mice

Chimera v2A (D2 NGC) was compared with its parental viruses, mouse-brain adapted dengue 2 NGC and v2A (Xho I), for mouse neurovirulence. Dengue 2 NGC proved to be the most rapidly lethal: each of 10 mice died of encephalitis on day 5 or day 6 post-inoculation, with a mean survival time of 5.1 days, while each of the 15 mice inoculated with chimera v2A (D2 NGC) survived 8–11 days before dying, with a mean survival time of 9.1 days (FIG. 6).

FIG. 6 presents three-day-old Swiss mice inoculated intracerebrally with 2000 pfu of either parental or chimeric dengue virus, in the form of a diluted lysate of infected LLC-MK$_2$ cells. The number of mice injected was: dengue 2 (NGC), 10 mice; v2A (D2 NGC), 15; dengue 4 814669, 12; v2A (Xho I), 18. Negative controls (11 mice) were injected with a diluted lysate of uninfected cells. Mice were then monitored daily for signs of encephalitis and for death.

The difference in survival distributions is significant (p=00001, Smirnov two-point statistic). Parental virus dengue 4 814669 were also compared to its progeny v2A (Xho I). Five of 12 mice inoculated with the parental virus died of encephalitis, the first death occurring on day 11, while only one of 18 mice inoculated with v2A (Xho I) died, 16 days after inoculation; the rest remained healthy. Although the survival distributions do not differ significantly according to the Smirnov statistic (p>0.14), the percent survival of the two groups differs by Fisher's exact test (p=0.0256). This suggests that dengue 4 814669, or a subset of virions in the virus preparation, possesses a degree of neurovirulence, and that progeny virus v2A (Xho I) may represent a non-neurovirulent sub-population, or may contain nucleotide changes which arose during cloning or virus propagation. None of 1 2 mice inoculated with parental dengue type 1 virus (WP), or 18 injected with its chimeric progeny v2A (D1 WP), or 11 which received a lysate of uninfected cells developed encephalitis or died.

Mutational Analysis

We have cloned a series of dengue cDNA inserts that spanned the entire length of the dengue type 4 virus genome. These were used in an initial attempt to clone a full-length dengue DNA, as in Example 4.

Example 4

Figure 7:
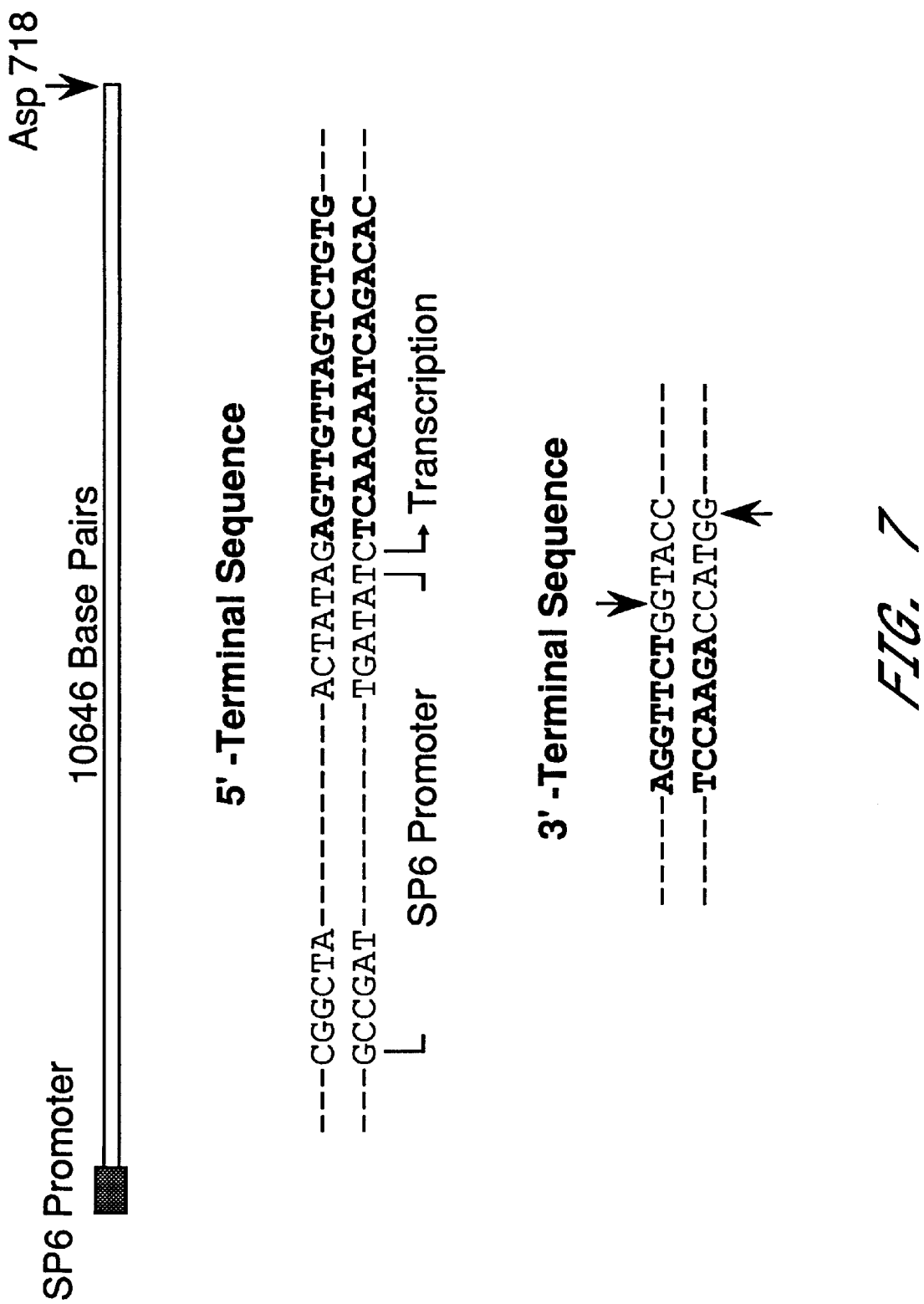
FIG. 7 provides the terminal sequences of cloned full-length dengue virus cDNA used for transcription of infectious RNA The full-length dengue virus cDNA totaling 10646 nucleotides in length was cloned adjacent to the promoter sequence for SP6 polymerase and the unique Asp 718 cleavage site as diagrammed. Note that there is an additional C residue at the position between 10448 and 10449 and an additional G residue between 10470 and 10471, which were missing in the original dengue type 4 virus sequence. The sequences near the predicted 5'-terminus and 3'-terminus of the RNA transcript are also shown. Transcription initiating G was placed preceding the 3'-dengue sequence as shown in bold letters. The Asp 718 cleavage sequence GGTACC was positioned immediately following the 3'-dengue sequence as shown in bold letters.

Initial Attempt to Clone a Full-Lenath denaue DNA in Plasmid pBR322 Containing the SP6 Promoter The various dengue type 4 cDNA inserts were joined at shared restriction enzyme sites to form a full-length dengue DNA copy using the same Pst I cloning site of PBR322. For in vitro transcription, the SP6 polymerase promoter sequence was placed at the 5'-end preceding the dengue sequence. The predicted 5'-sequence of the RNA transcripts is shown in FIG. 7. The A residue of the first dengue nucleotide is positioned immediately following the normal SP6 polymerase transcription initiating G. The m7G cap structure that is present at the 5'-end of the genomic RNA was provided by incorporation of a m7G pppG analog in the transcription reaction. Such a DNA structure would generate dengue RNA containing an additional nucleotide at the 5'-terminus. To produce run-off transcripts, a unique Asp 718 cleavage sequence was introduced at the 3'-end of the dengue sequence. As shown in FIG. 7, in the template strand 5 additional nucleotides are present preceding the Asp 718 cleavage site. If transcription proceeds to the last nucleotide, the RNA transcripts would contain these 5 additional residues at their 3'-terminus.

During this study employing *E. coli* strain HB101 as the host for transformation, it was noticed that plasmid containing the full-length dengue DNA were often unstable as plasmid in many transformants underwent rearrangement and many colonies had to be screened in order to isolate a clone DNA with the predicted restriction enzyme pattern. We sought to examine the stability of plasmid produced by different strains of *E. coli*. The highly transformation-competent, commercially available *E. coli* strain DH5α and *E. coli* strain DB1 528 used earlier in the laboratory were compared with E. coli strain HB101. It was found that strain DB1528 produced transformants exhibiting a colony size 3–4 times larger than HB101 transformants. Above all, transformants of DB1528 generally yielded plasmid with the predicted restriction enzyme pattern suggesting that *E. coli* DB1528 is the strain of choice to produce stably cloned dengue full-length DNA. However, the in vitro RNA transcripts made from this first full-length dengue DNA clone failed to produce dengue virus when tested on transfected cells where virion RNA as the positive control at 100-times less concentration yielded dengue virus as detected by an indicated immunofluorescence assay.

Example 5

Figure 8:
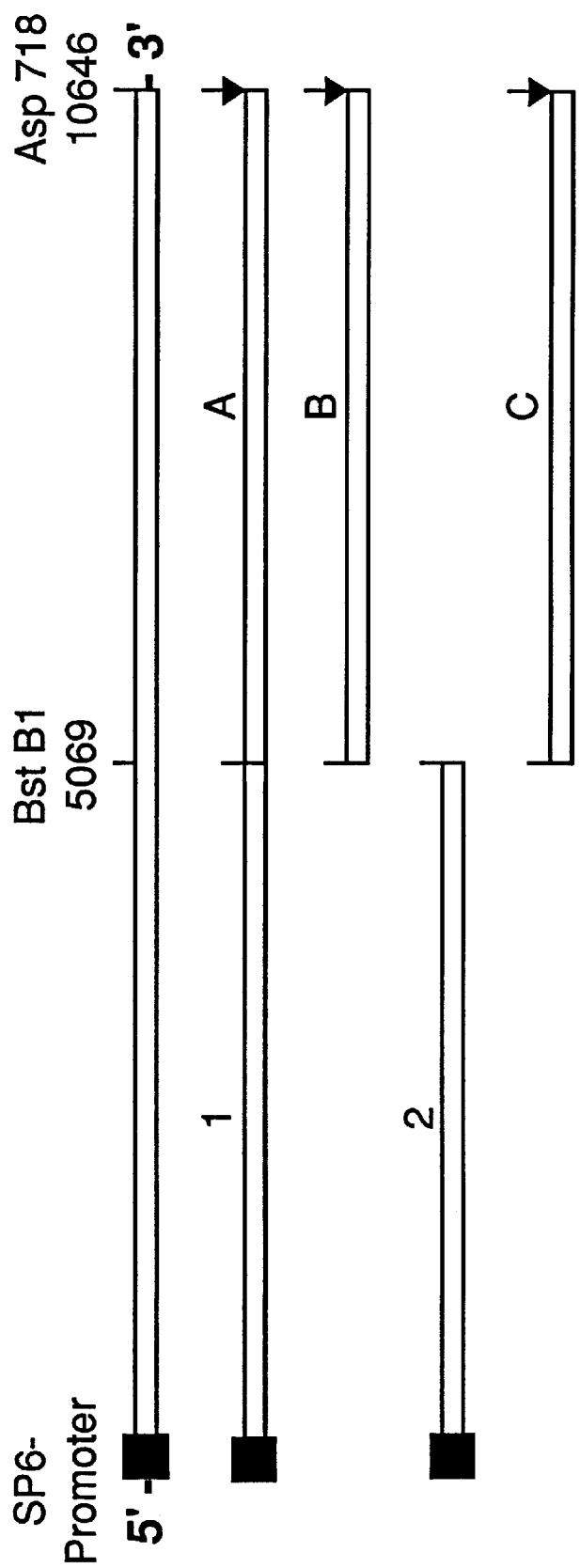
FIG. 8 diagrams the full-length dengue cDNA clones and the restriction endonuclease digestion pattern.

Replacement of Dengue DNA Segments in the Full-Length Construct with Independently Derived DNA Clones It was reasoned that the failure to produce infectious RNA transcripts was due to the presence of defective mutations in the full-length clone. Such mutations could presumably arise from cloning of a defective population in the virus stock or a coupling error during cloning or propagation of plasmid. We decided to carry out replacement of dengue DNA segments that might contain one or more defective mutations with the corresponding segments from independently cloned dengue DNA constructs. In order to provide a framework for a systematic replacement experiment the 5' and 3' fragments of the dengue sequence were cloned separately. The unique Bst B1 site at nucleotide 5069 was used to separate the full-length dengue sequence into two fragments each representing approximately 50% of the genome. The 5'-fragment of the first full-length clone containing the SP6 promoter was designated 5'-1 and the remaining 3' sequence between Bst B1 and Asp 718 designated 3'-A. A plasmid containing the second 5'-fragment, 5'-2, was constructed from an independently derived set of dengue CDNA inserts. A unique Asp 718 site was introduced at the Pst I site of pBR 322 downstream of the Bst B1 site of the dengue sequence. Thus, this plasmid was also suitable for use as a cloning vector for insertion of the 3' fragment in the full-length DNA construction. Two additional 3'-fragments, 3' -B and 3'-C were also constructed from an independent series of dengue cDNA inserts (FIG. 8). Replacement of the 3' fragment in the first full-length clone 1A with 3'-B or 3'-C fragments produced two other full-length clones, 1 B and 1 C. Similarly, substitution of the 5'-fragment in all three full-length DNA constructs with the 5'-2 fragment yielded three other full-length DNA clones, i.e., 2A, 2B and 2C. Digestion of these plasmids with Bgl II. Nsi I, and Asp 718 showed a pattern of predicted DNA fragments that was indistinguishable among all six full-length clones as shown in FIG. 9. Thus, the successful propagation of plasmid containing apparently full-length dengue DNA sequence in *E. coli* train DB1528 allowed the production of RNA transcripts in vitro for evaluation of their infectivity in cultured cells.

Example 6

Initial Evidence for the Infectivity of RNA Transcripts Made In Vitro

RNA transcripts produced from the constructed full-length dengue DNA templates were each tested for infectivity by transfection of LLC-MK$_2$ cells. Dengue infected cells were readily observed 10 days following transfection with 2A RNA as detected by an indirect immunofluorescence assay. RNA transcripts from other four full-length DNA clones were negative by this assay indicating that these DNA clones, like clone 1A, contained lethal mutations that were not detected by restriction enzyme analysis.

In addition to positive identification of dengue virus infected cells as described above, infectious dengue virus was recovered from the medium or the cell lysate of 2A RNA transfected cells. The titer of dengue virus present in the transfected cell lysate was $10^5$ pfu/ml. Treatment of 2A RNA transcripts with DNase I did not affect their infectivity while RNase treatment completely abolished their infectivity. Since plaguing of dengue virus was not carried out following transfection of cell monolayers with RNA, production of virus was identified following an extended incubation for virus amplification. Using this indirect immunofluorescence assay procedure, infectivity was detected at a minimum concentration with 1 ng genomic RNA or with 10 ng 2A RNA transcripts. These results of this test indicate that the RNA transcripts made from clone 2A were infectious following transfection of permissive cultured cells.

Example 7

Other Evidence for Infectivity of RNA Transcripts

In order to provide a formal proof that infectious dengue virus was produced by cells transfected with clone 2A RNA transcripts, two mutations (G3473→>T and C3476→>T) that created a new Pst I site at nucleotide 3473 in the dengue genome but did not affect amino acid sequence, were introduced into the full-length dengue clone 2A DNA. The RNA transcripts prepared from this mutant DNA, after complete removal of the DNA template by exhaustive digestion with DNase I, were used for transfection of cells. The transfected cells produced infectious dengue virus. Genomic RNA extracted from the progeny virus was reverse transcribed and the cDNA product was used as a template for PCR to generate a DNA fragment between nucleotides 3193–4536. As shown in FIG. 10, Pst I digestion of the PCR DNA product yielded two fragments 280 and 1063 base pairs in length as predicted by the presence of the Pst I cleavage sequence. The control PCR DNA product of virus derived from 2A RNA was insensitive to Pst I digestion. This observation provided evidence that the progeny virus derived from the RNA transcripts of the mutant 2A DNA containing the Pst I site.

Example 8

Denaue Virus Recovered from Infectious RNA Transcribed In Vitro

The progeny dengue virus was isolated from the lysate of cells transfected with RNA transcripts made from the clone 2A or clone 2A (Pst) template, and compared with the parental wild type virus for their ability to plaque on LLC-MK$_2$ cell monolayers. Six days after infection both progeny virus and parental virus produced characteristic dengue plaques of variable sizes. Although the parental virus grown by passages in mosquito cells showed predominantly small plaques, progeny virus mixed but yielded mostly large plaques, suggesting that recovered virus may represent a cloned population. Dengue specific proteins produced in progeny virus infected cells and in parental virus infected cells were also compared. As shown in FIG. 11, the profile of protein bands including PreM, E, NS1, NS2, and other unassigned dengue protein bands precipitated by dengue hyperimmune ascetic fluid appeared to be indistinguishable for both progeny virus and for parental virus. This result indicates that the recovered dengue virus exhibited the same genotype and phenotype of virus from which the cDNA clone was derived.

Engineering Viable Dengue Virus by Amino Acid Substitution at the NS1–NS2A Cleavage Junction

Example 9

Construction of NS1–NS2A DNA Specifing Amino Acid Substitutions at the Cleavage Site Seguence Intermediate recombinant pSC11-NS1-NS2A DNA constructed for expression of authentic NS1 was used in this study. The dengue virus DNA contained the coding sequence for the 24-amino-acid N-terminal signal and the entire polypeptide sequences of NS1 and NS2A. Initially, this plasmid DNA was modified to facilitate replacement of DNA segments containing mutations. Two silent mutations were introduced into NS1–NS2A DNA ($G_{3473}$→T and $C_{3476}$→A) by oligonucleotide directed mutagenesis. These changes created a new PstI site at nucleotide (nt) 3476. The recombinant plasmid contained a unique NcoI site at nt 3320 within the dengue NS1 coding sequence. The NS1–NS2A cleavage junction is located at nt 3477. In order to introduce amino acid substitutions at the cleavage site sequence, nucleotide changes were created by oligonucleotide directed mutagenesis. A series of oligonucleotide were synthesized and used as negative strand primers in a polymerase chain reaction (PCR). The positive strand primer was 5' AAGGC-TATGCCACGCAAA 3' (SEQ ID NO: 1) which is located upstream of the NcoI site. For example, at cleavage position −2 ($Thr_{1124}$) oligo GCC CTG GCC GGC CTT CAC CTG TGA TTT GAC CAT (SEQ ID NO: 2) was used to substitute Lys for Thr. In the same manner, oligo GCC CTG GCC GGC CTG CAC CTG TGA TTT GAC CAT (SEQ ID NO: 3) was used to substitute Gin for Thr, and oligo GCC CTG GCC GGC CAG CAC CTG TGA TTT GAC CAT (SEQ ID NO: 4) was used to substitute Leu for Thr. Similarly, oligo TTC TGA TGT GCC CTG TTC GGC CGT CAC CTG TGA (SEQ ID NO: 5) was used to substitute Glu for $Gly_{1120}$ at cleavage position +1, or oligo TTC TGA TGT GCC CTG CCA GGC CGT CAC CTG TGA (SEQ ID NO: 6) was used to substitute Trp for the same Gly at cleavage position +1.

For construction of intermediate recombinant DNA containing the specified mutation, the DNA fragment between the newly created PstI site and the unique NcoI site was replaced with the series of PCR DNA products that were cleaved with NcoI and PstI. Recombinant vaccinia viruses expressing these mutant NS1–NS2A sequences were made according to the procedure previously described (Zhao, B., Prince, G., Horswood, R., Eckels, K., Summers, P., Chanock, R. and Lai, C.J. (1987). Expression of dengue virus structural proteins and nonstructural protein NS1 by a recombinant vaccinia virus. *J. Virol.* 61:4019–4022).

Example 10

Analysis of Cleavaae at the NS1–NS2A Junction

Confluent CV-1 cells in a 6-well plate were infected with recombinant vaccinia virus at 5 PFU per cell and maintained in minimum essential medium plus 2% fetal calf serum (MEM2). AT 16–20 hours after infection, the medium was removed and placed with methionine-free MEM2 and after 1 hour of incubation, this medium was replaced with 0.7 ml of methionine-free MEM2 containing 1 00ici of $^{35}$S-methionine (specify activity >800 µci/mol). After a two-hour labelling period, cells were lysed in RIPA buffer (1% sodium deoxycholate, 1% Nonidot P-40, 0.1% sodium dodecyl sulfate [SDS]), 0.1 M Tris-HCl, pH 7.5, 0.15 M NaCl) and the lysate centrifuged to remove cell debris. The clear supernatant of the lysate was used for analysis of dengue virus proteins by immunoprecipitation using dengue hyper immune mouse ascitic fluid (HMAF). The immunoprecipitates were analyzed by electrophoretic separation on an SDS-12% polyacrylamide gel (acrylamide/bis ration-60:1.6). Labelled protein bands were visualized by fluorgraphy. The gel bands corresponding to the uncleaved NS1–NS2A precursor and the cleaved NS1 product were excised and the radio-activity counted in a liquid scintillation counter.

To determine the extent of cleavage at the NS1–NS2A junction, the differential immunoprecipitability between NS1–NS2A and NS1 was corrected on the assumption that the total label of the expressed NS1–NS2A was the same in cells infected with each mutant at the same pfu input. Wild-type NS1–NS2A expressed predominantly cleaved NS1 and the NS1–NS2A precursor was not detected. The extent of cleavage for wild-type virus was assigned 100%.

Example 11

Construction of Full-Length Dengue Type 4 cDNA Specifying Amino Acid Substitutions at the NS1–NS2A Cleavage Sequence Mutants of NS1–NS2A DNA that showed a range of reduced cleavage at the NS1–NS2A junction as constructed and analyzed in the previous section were selected for construction of dengue virus mutants containing such amino acid substitutions. Four such mutations established earlier were employed: (1) Gly at cleavage positive +1 Glu, (2) Thr at position −2 to Lys, (3) Thr at position −2 to Gin, and (4) Thr at position −2 to Leu. Mutant pscl1-NS1–NS2A DNA was digested with SpeI at nt 3338 and StuI at nt 3616 to isolate 278 at fragment. This DNA fragment containing the mutation was used for replacement of the corresponding wild-type DNA fragment in plasmid p5'-2 which contains the 5'-half of the dengue cDNA sequence. The remaining 3' dengue cDNA fragment between BstE1 (nt 5069) and Asp718 at the 3' end was joined to the p5'-2 DNA at the shared restriction enzyme cleavage sites. In this manner, full-length cDNA was created and cloned using the pBR 322 vector. This series of cDNA contained mutated sequences coding for amino acid substitutions at the NS1–NS2A cleavage junction.

Example 12

Dengue Virus Type 4 Virus Mutants Exhibitina Suboptimal Cleavage at the NS1–NS2A Junction A major emphasis is now being placed on the application of the molecular understanding of dengue virus to the development of safe and effective, attenuated live virus vaccines against dengue disease. Restriction of dengue virus replication should cause attenuation. Modification of a cleavage sequence or viral protease components may result in suboptimal cleavage of the viral polyprotein thus restricting viral growth.

The polyprotein NS1–NS2A cleavage site has been chosen as the first target for constructing dengue virus mutants that are growth-restricted because of inefficient cleavage. We have shown that NS1–NS2A cleavage of dengue type 4 virus requires an 8 amino-acid sequence at the C-terminus of NS1 preceding the cleavage junction (Hori, H. and Lai, C. J. (1990). Cleavage of dengue virus NS1–NS2A requires an octapeptide sequence at the C terminus of NS1. *J. Virol.* 64:4573–4577).

Comparison of the 8 amino-acid sequence among flaviviruses revealed an interesting motif in which Ala(−1), Val(−3), Ser(−5), Val(−7), and Met/Leu−8) are strictly conserved, whereas Thr(−2), Gln(−4), and Lys(−6) vary. The effect of amino-acid substitutions of Ala at position −1, Thr at position −2, Val at position −3, and Gly at position +1 has been analyzed. The result of this analysis is shown in FIG. 16. Amino acid substitution at conserved position −1, or −3 yielded a low level of cleavage. Substitutions of amino acids at non-conserved position −2, or +1 showed no effect or only moderate reduction of cleavage.

A panel of amino acid substitutions that produced a range of cleavage efficiencies were selected for incorporation into the full-length cDNA and the in vitro derived RNA transcripts were used for the construction of dengue virus mutants. One dengue virus mutant designated DEN4(Gly, $_{1120}\to$Glu) that contained Glu substituting for Gly (+1), and three other mutants designated DEN4 (Thr$_{1124}\to$Lys), DEN4 (Thr,$_{1124}\to$Gln), and DEN4 (Thr,$_{1124}\to$Leu), containing substitutions of Thr(2), were recovered from transfected LLC-MK$_2$ cells.

The growth properties of these mutants were characterized by plaque assay on mosquito C6/36 cells, as described below. FIG. 12 shows the result of this assay DEN4 (Gly, $_{1124}\to$Glu) and the control parent virus. The plaque size of the mutant virus measured approximately 0.1 cm in diameter was greatly reduced compared to the plaque size of 1.1 cm for the parent virus; other dengue virus mutants also showed reduced plaque size suggesting that these viruses exhibited growth restriction in cultured cells. It is likely that the growth restriction resulting from suboptimal cleavage may have a profound effect on viral virulence in the infected host.

Engineering Viable Dengue Virus 3' Noncoding Region Deletion Mutants

Example 13

Construction of Dengue cDNA Containing Deletions in the 3' Noncoding Region

To facilitate introduction of deletion mutations into the 384-nucleotide 3' non-coding region, the 540 nt subfragment of dengue 4 cDNA between the unique BamHI site at nt 10104 and the Asp718 site at the 3' end was initially inserted into the pGEM3 cloning vector. In this recombinant plasmid the unique ApaI site at nt 10470 of the dengue 4 sequence is located approximately at the midpoint of the 3' non-coding sequence. Using the conveniently located ApaI site two series of deletion mutations were constructed: one series of the constructs contained deletions downstream of the ApaI site and the other series of deletions was placed upstream of the ApaI site. Oligonucleotide-directed mutagenesis was performed to engineer the first series of deletion mutations ranging from 30 to 90 nucleotides in length.

The following oligonucleotide that contain the ApaI cleavage site, the appropriate deletions as indicated, followed by the downstream sequence were used as positive strand primers in a PCR.

oligo CAA AAG GGG GCC CAA GAC TAG AGG TTA CAG GAG ACC—(Δ3' 172-143) (SEQ ID NO: 7)

oligo CAA AAG GGG GCC CAA AAA CAG CAT ATT GAC GCT GGG—(Δ3', 172-113) (SEQ ID NO: 8)

oligo CAA AAG GGG GCC CAA CAG AGA TCC TGC TGT CTC TGC—Δ3' 172-83) (SEQ ID NO: 9)

The negative strand primer was oligo GAG CTG GTA CCA GAA CCT GTT GGA TCA A (SEQ ID NO: 10) which contains the 3' dengue sequence followed by the Asp718 cleavage sequence. The full-length dengue 4 cDNA (clone 2A) was used as the template. To introduce these deletion mutations into the dengue 4 sequence, the wild-type virus DNA fragment between the ApaI and the Asp718 sites in the pGEM3 recombinant plasmid was replaced with the PCR DNA products which were cleaved with ApaI and Asp718.

Similarly, oligonucleotide-directed mutagenesis was also performed to engineer the second series of deletion mutations ranging from 61 to 202 nucleotides in length and place upstream of the ApaI site. The following oligonucleotide were synthesized and uses as negative strand primers in a PCR.

oligo CCT GGC TTG GGC CCC CGC GTA CAG CTT CCG TGG CGC—(Δ3', 243-183) (SEQ ID NO: 11)
oligo CCT GGC TTG GGC CCC GGA GCT ACA GGC AGC ACG GTT—(Δ3', 303-183) (SEQ ID NO: 12)
oligo CCT GGC TTG GGC CCC CGT GGC ACA AGT GGC CTG ACT—(Δ3', 333-183) (SEQ ID NO: 13)
oligo CCT GGC TTG GGC CCC TTA CAG AAC TCC TTC ACT CTC TGA—(Δ3', 384-183) (SEQ ID NO: 14)

The positive strand primer was oligo GCC TCC ATG GCC ATA TGC TCA GC (SEQ ID NO: 15) which is located between nucleotides 9885–9907 upstream of the BamHI site. The full length dengue 4 cDNA was used as the template. As was described earlier, to introduce these deletion mutations into the dengue 4 sequence the wild-type virus DNA fragment between the BamHI and the ApaI sites in the intermediate pGEM3 plasmid was replaced with the PCR DNA products which were cleaved with BamH1 and ApaI. In the last stage of engineering the cDNA template, the BamH 1-Asp718 fragments from both series of constructs were isolated and cloned with the remaining dengue 4 sequence.

Example 14

RNA Transcription, Transfection and Recovery of Virus

Dengue virus cDNA clones were linearized by digestion with Asp718 at the 3' end and the linear DNA was used as templates for in vitro transcription by SP6 polymerase. Transfection of cells with RNA transcripts was performed as described (Lai, et al., *Proc. Natl. Acad. Sci. USA* 88:5139–5143 (1991)). Ten days after transfection, cells were trypsinized and transferred to a 6-well plate and to a chamber slide. Two days later, cells on the slide were tested by immunofluorescence (IFA) for evidence of dengue virus antigens. If IFA showed most cells were infected, the infected cells in the 6-well plate were harvested by removing the medium, scraping the cells, resuspending them in a standard volume of 50% Eagle's minimal essential medium/ 50% sera, and then freezing. On the other hand, if a small percentage of cells were positive, the cells were trypsinized, diluted in 1:3 in fresh medium, and allowed to grow. The percentage of infected cells were then estimated on a weekly basis, and cell lysates were harvested.

Example 15

Plague Morpholoay

Viruses were characterized for plaque morphology on primate-derived LLC-MK$_2$ cells or on mosquito C6/36 cells (Bankcroft, et al., *Pan Am. Health Organ. Sci. Publ.* 375:175–178 (1979); Hoke, et al., *Am. J. Trop. Med. Hyg.* 43:219–226 (1990)). Parental wild-type virus was passaged once in LLC-MK$_2$ cells prior to analysis of plaque morphology. Specifically, LLC-MK$_2$ cells in a 25-cm$^2$ flask were injected with 0.2 ml of dengue virus to be tested in a serial 10-fold dilutions in medium 1 99 containing 2% fetal bovine serum. After absorption for 1 hour at 35° C., each monolayer was added with 7 ml of an agarose overlay containing 1×medium 199, 0.3% sodium bicarbonate ½×, Eagle basal medium vitamins and ½× Eagle basal medium amino acids 10% fetal bovine serum, 0.5% agarose. After incubation for six days at 35° C., the flasks were overlaid a second time with 4.0 ml of normal saline containing 0.5% ME agarose and 1:7,500 neutral red. Virus plaques appeared within 24 hours after staining. Plaque morphology on C6/36 cells was carried out to characterize all viruses mutants isolated. For this purpose, confluent C6/36 cells in a 75 -cm$^2$ flask were inoculated with 0.5 ml of virus serially diluted in MEM plus 2% fetal bovine serum, allowed to absorb at 35° C. for 1–2 hours. The infected cells were then added with 20 ml/flask of an agarose overlay (1× Hanks' balanced salt solution, 0.5% lactalbumin hydrolysate, 10% fetal bovine serum, 0.12% sodium bicarbonate, 0.75% Seakem™ GTG agarose). Cultures were incubated for 7 days at 35° C. Cultures were then stained with 5 ml of a liquid neutral red stain solution consisting of NaCl 8.0 g/l, KCI 0.4 g/l, glucose 1.0 g/l, Na$_2$HCO2, 22.5 mg/l, and neutral red 3.3 mg/l. After 3-5 hours incubation at 35° C. the excess stain was removed and the cultures returned to the incubator. Plaques were generally visible following 24–36 hours in the incubator.

Example 16

Dengue Type 4 Virus Mutants Containing Deletion in the 3' Noncoding Region

The dengue recombinant DNA system now also allows us to construct dengue virus mutants containing deletions in the 5' and 3' noncoding regions of the viral RNA as well as the coding region. Deletion mutants would offer the advantage of being less subject to reversion of phenotype than amino acid substitution mutants. Progress has been made in engineering deletion mutations in the 3' noncoding region of the dengue type 4 virus genome. Like other mosquito-borne flaviviruses, dengue type 4 virus contains stretches of conserved sequences, termed conserved sequence 1 (CS-1) and conserved sequence 2 (CS-2), and a potential terminal stem-and-loop structure in the 3' noncoding region.

Deletions ranging from 30–120 nucleotides have been produced in various locations in the 385 nucleotide 3' non-coding sequence of dengue type 4 virus RNA. Mutant RNA transcribed from a cDNA clone lacking sequences in the CS-1 region, but retaining the stem-and-loop structure did not produce progeny virus suggesting that the deletion virus has been recovered from most other deletion constructs (FIG. 13). Plaque assay of these mutants and the wild type virus control was performed on C6/36 cells.

The results of this analysis showed that most of these mutants formed plaques that were reduced in size, ranging from 1.0 to 0.3 cm, dependent on the location and the extent of deletion (FIG. 14 and 15). The altered plaque morphology indicates that these deletion mutants exhibited a growth-restriction phenotype. This panel of deletion mutants may exhibit other interesting and potentially important properties such as reduced virulence for experimental animals and humans.

Example 17

Full-Length Chimeric TBEV/DEN4 cDNA and Production of Chimeric Viruses

Previously, subgenomic cDNA fragments of the TBEV (strain Sofjin) were cloned and the nucleotide sequence determined (see Pletnev et al., *Virology* (1990), supra.). Plasmids pGEM2-CME containing nucleotides (nt) 76–1977 and pGEM2-ENS1 containing nucleotides 966–3672 of the TBEV sequence were provided by Dr. E. Yu. Dobricova (Novosibirsk Institute of Bioorganic Chemistry, Russia) from plasmids p10, p4, p18, p2, p11 (Pletnev et al., supra) by joining the TBEV segments at shared restriction enzyme sites. Plasmids DEN4 p5'-2 and p5'-2(ΔPStI,XhoI), and a derivative p5'-2 (ΔPStI,XhoI, ΔHindIII) (Bray et al., *Proc. Natl. Acad. Sci. USA*, (1991) supra) were used as the recombinant cDNA construct for the substitution of one or more TBEV genes in place of the corresponding DEN4 genes. Synthetic oligonucleotides (oligos) were used as negative or positive-strand primers to generate double-stranded DNAs by polymerase chain reaction (PCR). Restriction enzyme cleavage sequences were introduced at or near the TBEV and DEN4 intergenic junctions by PCR-directed site-directed mutagenesis (FIG. 1 7). Seven intermediate chimeric plasmids containing the indicated TBEV genes were initially constructed and stable full-length TBEV/DEN4 cDNAs were identified after transforming *E. coli* strain BD1528 (described by Lai et al., (1991) supra). The sequences surrounding the junctions between TBEV and DEN4 genes in each plasmid were confirmed by nucleic acid sequencing using techniques well known in the art of molecular biology. All chimeric plasmids contained the SP6 promoter positioned upstream of a transcription initiating G followed by an A residue representing the first DEN4 nucleotide. Prior to in vitro transcription, plasmids were linearized at the unique Asp718 cleavage site immediately following the 3' end of the DEN4 sequence (using techniques provided by Lai et al., *Proc. Natl. Acad. Sci. USA* (1991) supra.). Recovery of chimeric viruses and subsequent study of their properties was conducted in a BL-3 containment facility. Transcription reactions were performed essentially as described by Lai et al., *Proc. Nal. Acad. Sci. USA* (1991) supra. Prior to transfection, the transcription mixture was treated with 40 u/ml DNase I at 37° C. for 15 min. The RNA transcripts were then used to transfect semiconfluent simian LLC-MK$_2$ cells in the presence of (i) Lipofectin™ (Bethesda Research Laboratories, Inc.) as described previously by Lai et al. supra or (ii) N-[1-(2, 3-dioleoyloxy)propyl]-N, N, N-trimethylammoniummethylsulfate (DOTAP) (Boehringer Manneheim). Under DOTAP transfection conditions, the transfection mixture contained RNA transcripts (2 μg) in 40 μl of 0.02 mM Hepes buffer, pH 7.05, and 12 μl DOTAP in 30 μl Hepes buffer. After incubation at room temperature for 10 min., 2 ml medium 199 containing 10% fetal bovine serum (FBS) was added; 0.5 ml of the mixture was distributed to subconfluent cells in 4 wells of a 24-well plate. Ten days later, cells were trypsinized and transferred to a 6-well plate and to chamber slides for an additional 2 days of incubation in growth medium. Cells on the slides were tested by immunofluorescence assay (IFA) to detect the presence of DEN4 or TBEV antigens using a 1:100 dilution of DEN4-specific hyperimmune mouse ascitic fluid (HMAF), TBEV-specific HMAF, or TBEV-specific rabbit serum (kindly supplied by Dr. A. S. Karavanov, Institute of Poliomyelitis, Moscow, Russia). Fluorescein-conjugated anti-mouse or anti-rabbit serum (Kirkegaard-Perry, Gatithersberg, Maryland) was used at the same dilution. When IFA indicated that 50–80% of cells were infected, cells in the 6-well plate were trypsinized, mixed with 2-fold excess uninfected cells, and grown in a T$_{75}$ flask for 6 days. The infected cells were then harvested together with the medium, mixed with an equal volume of fetal bovine serum, and frozen as a cell suspension. The thawed cell lysate was used as the source of progeny chimeric virus. Only TBE (ME)/DEN4 and TBE(CME)/DEN4 were identified by transfection experiments using Lipofectin™ or DOTAP. Progeny virus was identified by immunofluorescent assay.

To verify the genomic structure of progeny chimeric TBE(ME)/DEN4 virus designated vTBEV(ME)/DEN4, the total cellular RNA was isolated from infected LLC-MK$_2$ cells by phenol extraction using techniques provided by Mackow et al., *Virology* 159:217–228, 1987. Oligo 5'GCTC-CGGGGTGTAAGTCCATT3' (SEQ ID NO: 16) complementary to nucleotide (nt) positions 5090–5110 (see Mackow, et al., *Virology* 159:217–228, 1987) of the DEN4 sequence was used as a primer for reverse transcription. Single-strand cDNA was used as a template and oligo 5'GACCGACAAGGACAGTTCCAAATCGGA3' (SEQ ID NO: 17) at nt positions 18–44 of the DEN4 sequence served as the positive strand primer, and oligo 5'CTTTTTGGAAC-CATTGGTGACT3' (SEQ ID NO: 18)at nt positions 2130–2152 of the TBEV sequence as the negative strand primer for PCR. For nucleotide positions relating to dengue virus see Zhao, et al., *Virology* 1 55:77–88, 1986 and for nuctotide positions relating to tick-borne encephalitis virus see Pletnev et al., *Virology*, (1990), supra. The PCR DNA product of 2118 base-pairs (bp) was digested with PstI, BglII or EcoRI to verify the presence of restriction enzyme sites. Similarly, oligo 5'GTCCGGCCGTCACCTGTGATT3' (SEQ ID NO: 19) and oligo 5'TCACGGTGCACA-CATTTGGAAAAC3' (SEQ ID NO: 20) (complementary to DEN4 genome at 3459–3480 nt and complementary to the negative strand of TBEV genome at 967–985 nt, respectively) were also used in PCR. The PCR product was digested with EcoRI, PstI, BamHI, XhoI or SphI to verify the DNA sequence. The PCR DNA product (2118 bp) from the vTBE(ME)/DEN4 genome was digested with HindIII and BamHI restriction endonuclease enzymes. The HindIII-BamHI-subfragment (1922 bp) was purified by PAGE and cloned into the pGEM3 vector at the complementary restriction sites. The sequence of the junction between the C gene of DEN4 (300–398 nt) and the preM gene of TBEV (418–460 nt) was confirmed by nucleic acid sequencing Oligonucleotides used for the Construction of TBE/DEN4 Chimeric DNA Included
TBEV-specific Oligos
5'CCGGTTTATAGATCTCGGTGCACACATTTGGAAAA C+(SEQ ID NO: 21)
5'CTCCATTGTCTGCATGCACCATrGAGCGGACAAGC CC–(SEQ ID NO: 22)
5'CTTAGGAGAACGGATCCTGGGGATGGC-CGGGAAG
GCCATTCTG+(SEQ ID NO: 23)
5'GGCAAAAGAAGGTCTGCAGTAGACTGGACAGGT TGG+(SEQ ID NO: 24)
5'GAAGGAAGCTCATGGACATGGTCGGATTCCTCGA GTrCAGGCCCAACCAGGC–(SEQ ID NO:25)
5'CCTGGCCTGGTTGGGCCGAACTCGAGGAATCCGA CCATGTC+(SEQ ID NO: 26)
5'GTCCAGTCTACTGCAGACCTTCTTTTGCCACGTCT TTG–(SEQ ID NO: 27)
DEN4-specific Oligos
5'TACGCATCGGGATCCGTAGGATGGGGCGACCAGC AT–(SEQ ID NO: 28)
5'TCACAGGTGCATGCCGGACAGGGCACAT-CAGAAA
CT+(SEQ ID NO: 29)
5'CAGCAATGTTACTGCAGACCTTTTCTCCCGTTC– (SEQ ID NO: 30)

5'GGGAGAAAAAGGTCTGCAGTAACAT-TGCTGTGCTTGATCCC +(SEQ ID NO: 31)

ID SEQ NO: 23 was used to prepare the DEN4 5' noncoding region/TBEV capsid junction to form a Bgl II/Bam H1 site. ID SEQ NOS: 30 and 24 were used to prepare the DEN4 C/TBEV PreM junction to form Pst1/Pst1 sites. SEQ ID NOS: 28 and 21 were used to prepare the DEN4 Pre M/TBEV E junction to form Bam H1/Bg1 II sites. The DEN4 NS1/TBEV NS1 junction was prepared using SEQ ID NO: 26 to form Xho1/Xho1 sites. The TBEV E/DEN4 NS1 junction was prepared using SEQ ID NO:25 to form Xho1/Xho1 sites. The TBEV C/DEN4 Pre M junction was prepared using SEQ ID NOS: 27 and 31 to generate PST1/Pst1 sites and the TBEV NS1/DEN4 NS2A junction was prepared using SEQ ID NOS: 22 and 29 to generate Sphl/Sphl sites. The + and − signs associated with the sequences identify upstream and downstream primers respectively.

Example 18

Protein Analysis of Chimeric Virions

To analyze proteins produced by DEN4 v2A(XhoI), the full length dengue 4 virus cDNA construct, or vTBE(ME)/DEN4, confluent LLC-MK$_2$ cells in a 6-well plate were infected with the respective virus at an MOI of 1.0. Six days after infection, cells were labeled with [$^{35}$S]-methionine (60 µCi per well, specific activity 600 Ci/mmole) in methionine-free MEM (Eagle's minimal essential medium) for 4 hr as described by Lai et al., Proc. Natl. Acad. Sci. USA, (1991), supra. Lysates were immunoprecipitated with 1) TBEV-specific HMAF; 2) DEN4-specific HMAF; 3) rabbit serum raised against TBEV E, or 4) rabbit antiserum specific to DEN4 preM, E, NS3, or NS5 protein. Immunoprecipitates were analyzed by PAGE under denaturation conditions using the techniques described by Laemmli, supra.

Analysis of Protein Synthesis Over Time

LLC-MK$_2$ or C6/36 cell monolayers in T$_{25}$ flasks were infected with vTBE(ME)/DEN4 or DEN4 (v2A(XhoI)) at an MOI of 1. After adsorption at 37° C. for 1 hr, the virus inoculum was removed and fresh medium was added to the cells. For analysis of protein synthesis, infected cells at various times (0, 4, 8, 24 and 48 hr) following virus adsorption were incubated with methionine-free MEM for 20 min and labeled with [$^{35}$S]-methionine in the same medium for 2 hr. The lysate of labeled cells was precipitated with DEN4-specific HMAF and analyzed by PAGE and autoradiography.

Example 19

Growth Analysis of Chimeric Construct

Parental DEN4 and its chimeric viruses were characterized by plaque assay on simian LLC-MK$_2$ and mosquito C6/36 cells. The techniques for plaque assay are described by Bancroft, et al., supra. Growth analysis as provided in FIG. 19 was performed by quantitating the amount of virus present in DEN4 or TBE(ME)/DEN4 infected LLC-MK$_2$ and C6/36 cultures at various days postinfection. Following infection and virus adsorption, cultures were harvested and each culture was sampled by plaque assay. The changing virus titer in Log (pfu/ml) is presented as growth curves over time.

Example 20

Analysis of Viral RNA Synthesis

For analysis of viral RNA synthesis, infected LLC-MK$_2$ or C6/36 cells (approximately 10$^6$ cells) were collected at various times (0, 4, 8, 24, 48 hr) following virus adsorption, rinsed with 0.5 ml phosphate-buffered saline (PBS), pH 7.4, and then lysed in buffer containing 0.3M NaAc, pH 5.2, 5 mM EDTA and 1% SDS. Total RNA was isolated from the cell lysate and the medium by phenol extraction using techniques provided Maniatis, et al., supra. RNA samples were denatured by incubation in 6×SSC (1×SSC is 0.15M NaCl and 0.015M sodium citrate) containing 7.5% (wt/vol) formaldehyde at 60° C. for 15 min and bound to a nitrocellulose filter BA85 (Schleicher and Schuell). Filters were baked at 80° C. for 1 hr and prehybridized in a solution containing 6×SSC, 3×Denhardt solution, 25 mM Na$_2$HPO$_4$ (pH 6.5), 0.1% SDS and salmon sperm DNA 25 µg/ml at 65° C. for 1 hr. Hybridization was continued overnight at 65° C. in the same solution containing a nick-translated, [$^{32}$P]-labeled pTBE(ME)/DEN4 DNA probe (50 ng/ml, specific activity 3,4×10$^3$ cpm/µg). After hybridization, the filters were washed five times in 0.1×SSC containing 0.1% SDS at 65° C., dried and exposed to an X-ray film at 70° C. The radioactivity of [$^{32}$P]DNA hybridized to RNA was also measured in a liquid scintillation counter. RNA transcripts made in vitro from pTBE(ME)/DEN4 were used as a positive control.

Example 21

Testing Protective Efficacy of the Vaccine Pregaration and Neurovirulence of Chimeric Viruses vTBE(ME)/DEN4 and parental dengue virus were analyzed for neurovirulence by inoculating mice by intracerebral (IC), intradermal (ID) or intraperitoneal (IP) routes. Three-day-old suckling BALB/c mice were injected IC with a dose of 10$^2$ pfu of virus in 0.02 ml of MEM/0.25% human serum albumin. Six-week-old BALB/c female mice were (i) inoculated IC with a dose of 10$^3$ pfu of virus, diluted as above, in a volume of 0.03 ml, or (ii) inoculated ID or IP with 10$^3$ pfu of a virus, diluted in a volume 0.10 ml. Mice were observed for 21 days for symptoms of encephalitis or death, and surviving adult mice were bled 20 days after infection to evaluate antibody responses to the inoculated virus. Surviving mice were challenged IP at 21 days with 10$^3$ LD$_{50}$ TBEV (strain Sofjin) in a BL-4 containment facility.

Example 22

Construction and Sequencing of Chimeric Viral Mutants

Mutations were introduced into the TBEV(ME)/DEN4 construct using site-directed mutagenesis according to the standard oligo, PCR-drive procedure well known by those with skill in molecular biology (see oligo sequences below). The resulting constructs were transfected into LLC-MK$_2$ cells using techniques disclosed in Example 17. Progeny virus that was recovered from the mutagenized constructs was assessed for alterations in plaque morphology using the techniques provided in Example 19. Strategic mutations were introduced into the full-length TBE(ME)/DEN4 cDNA construct in order to systematically achieve modifications in predetermined regions of the chimeric viral genome. Six mutant chimeras were recovered from the transfected LLC-MK$_2$ cells and the virus progeny were analyzed for their ability to induce mouse neurovirulence. Other viral growth properties were additionally assessed in cultured cells. As provided in FIG. 23, four virus mutants that contained an ablated glycosylation site in the PreM, E, or NS1 glycoprotein were predicted to exhibit a glycosylation defect at the site indicated. Mutant *PreM/M⁻ contained a defective cleavage sequence at the PreM/M intergenic junction. Mutant *E contained two amino acid substitutions these substitutions were chosen because these amino acids are found only in mosquito-borne flaviviruses.

Mutations were introduced into the TBE(ME)/DEN4 construct by site-directed mutagenesis according to the standard oligo, PCR-driven procedure. Briefly, a positive strand oligo and its complementary negative strand oligo, each containing the mutation sequence and a unique restriction enzyme site, were used together with the oligo of the respective downstream or upstream primer pair in a PCR. Both PCP products were joined at the shared unique restriction enzyme site. In this manner, the resulting DNA fragment containing the mutated sequence was made to substitute for the corresponding wildtype DNA fragment in full-length TBE(ME)/DEN4 cDNA. Following is a list of specific mutant chimeric DNA's and oligonucleotides used in the construction.

(1) Mutant PreM/M-Glc:
5'GCGGCAACCCAGGTGCGTGTCGATCGTG-GCACCTGTGTGATCCTGG +(SEQ ID NO: 32)
5'CCAGGATCACACAGGTGCCACGATCGA-CACGCACCTGGGTTGCCGC −(SEQ ID NO: 33)
(2) Mutant E-Glc:
5'GGGGGATTACGTCGCTGCTCTAGAGACT-CACAGTGGAAGAAAA +(SEQ ID NO: 34)
5'TTTTCTTCCACTGTGAGTCTCTAGAG-CAGCGACGTAATCCCCC −(SEQ ID NO: 35)
(3) Mutant NS1(1)-Glc:
5'TTCACCCCAGAAGCAAGGATCCGCA-CATTTTTAATAGACGGAC +(SEQ ID NO: 36) 5'GTC-CGTCTATTAAAAATGTGCGGATCCT-TGCTTCTGGGGTGAA −(SEQ ID NO: 37)
(4) Mutant NS1 (2)-Glc:
5'TGGATAGAGAGCTCAAGGATCCAGACT-TGGCAGATAGAGA +(SEQ ID NO: 38)
5'TCTCTATCTGCCAAGTCTGGATCCT-TGAGCTCTCTATCCA −(SEQ ID NO: 39)
(5) Mutant PreM/M:
5'GGATCAAGAACAAGACGCGTAGTGCT-GATCCCATCCCAC +(SEQ ID NO: 40) 5'GATGGGAT-CAGCACTACGCGTCTTGTTCTTGATCCTFCTTG (SEQ ID NO: 41)
(6) Mutant E:
5'AGAGACCAGAGCGATCGAG-GCTGGGGCAACGGGTGTGGATTTTTTGGAAAA +(SEQ ID NO: 42)
5'GCCCCAGCCTCGATCGCTCTG-GTCTCTCTTACACACTTACGACGG −(SEQ ID NO: 43)
Also, the upstream primer was (SEQ ID NO: 44)
5'GACCGACAAGGACAGTTCCAAATCGGA +
and the downstream primer was (SEQ ID NO: 45)
5'CTTTGAACTGTGAAGCCCAGAAACA-GAGTGATTCCTCCAACAGCTATGCA −

Example 23

Analysis of Neurovirulence in Mice

In addition the mutated chimeric virus preparations were inoculated IC into mice and compared with DEN4, TBE (ME)/DEN4 and TBE(CME)/DEN4 using the techniques provided in Example 21. The lethal dose required to kill one half of the animals tested was compared for each of the mutated chimeric viruses. Six-week old BALB/c mice in groups of 8 were inoculated intracerebrally with various mutant chimeras, TBE(ME)/DEN4, TBE(CME)/DEN4, or DEN4 at a dose of 1000, 100, 10, 1, and 0.1 pfu. Infected mice were observed for signs of encephalitis and death for 31 days. The 50% lethal dose (LD50) was calculated for each virus and the value was used as the basis for mouse neurovirulence. As can be seen in FIG. 23, the LD50 of the parental TBE(ME)/DEN4 virus was approximately 10 pfu. This level of LD50 was also observed for several mutant viruses. At least two mutants, *NS1 (1)-Glc⁻ and *PreM/M⁻, showed an LD50 greater than 100 pfu indicating that these mutants exhibited a greater than 100-fold reduction of mouse neurovirulence. This finding indicates that the NS1 (1)-Glc⁻ or PreM/M⁻ mutation in the chimeric viral genome can each confer attenuation of mouse neurovirulence. These mutant viruses separately or together should be valuable for further evaluation of their usefulness as candidate vaccines.

Example 24

Testing Optimized Chimeric Constructs in Primates

It has been established that subhuman primates, but not other animals, are readily infected with dengue virus by the peripheral route (Simmons, et al., Philipp. *J. Sci.* 44:1–247, 1931 and Rosen, *Am. J. Trop. Med. Hyg.* 7:406–410, 1958). Infection of monkeys represents the closest experimental system to dengue virus infection of humans. The response of rhesus monkeys to dengue infection is similar to that of humans in that there is a four to six day viremia, although lower primates do not develop clinical dengue symptoms. The objectives of dengue or other flavivirus studies in monkeys are: (1) to evaluate the immunogenicity of various candidate vaccines; (2) to evaluate the infectivity and virulence (attenuation phenotype) of candidate live dengue or chimeric dengue virus vaccines as measured by the duration of viremia in days and the peak virus titer in pfu/ml; and (3) to evaluate the protective efficacy of the above-mentioned vaccines against challenge by homotypic dengue virus or other flavivirus of the same chimeric virus specificity.

(1) Inoculation: Each rhesus monkey is inoculated with a total of $3 \times 10^6$ pfu of virus diluted in Eagle's minimal essential medium/0.25% human serum albumin. Normally, two subcutaneous doses are given to anesthetized animals.

(2) Blood collection: Following inoculation of dengue virus or chimeric dengue virus, blood sample of 3.0 ml are taken daily for two weeks and 5.0 ml at 3 weeks, 4 weeks, 6 weeks, and 8 weeks.

(3) Challenge dengue virus or other flavivirus: Where virus challenge is deemed appropriate to evaluate the protective efficacy, monkeys are inoculated with non-attenuated virus at $10^5$ pfu/dose in a 0.5 ml volume subcutaneously in the upper arm area.

(4) Laboratory assays: Serum samples are used to determine: (a) the viremic duration by direct viral plaguing assay; (b) the titer of dengue or other flavivirus specific antibodies by radio-immunoprecipitation and ELISA; and (c) the titer of neutralization antibodies by plaque reduction neutralization test, all tests well known to those skilled in the art of vaccine development.

While particular embodiments of the invention have been described in detail, it will be apparent to those skilled in the art that these embodiments are exemplary rather than limiting, and the true scope of the invention is to be interpreted in view of the following claims.

What is claimed is:

1. A recombinant genetic construct, adapted to encode a chimeric flaviviral genome, comprising:

a full genome-length nucleic acid clone of a flavivirus genome having a region of nucleic acid encoding structural protein of a first flavivirus linked to a region of nucleic acid encoding non-structural protein of a second flavivirus, wherein said second flavivirus is a different flavivirus from said first flavivirus, and wherein said flavivirus is defined as an approximately 11-kilobase positive strand RNA virus having a genome that codes in one open reading frame for three structural proteins, capsid (C), premembrane (preM) and envelope (E), followed by seven non-structural proteins, NS1, NS2A, NS2B, NS3, NS4A, NS4B and NS5.

2. The genetic construct of claim 1, wherein said second flavivirus is a dengue virus.

3. The genetic construct of claim 2, wherein said first flavivirus is a member selected from the group consisting of dengue type 1 virus, dengue type 2 virus, and dengue type 3 virus, and said second flavivirus is dengue type 4 virus.

4. The genetic construct of claim 2 further comprising at least one mutation that is introduced into the viral genome.

5. The genetic construct of claim 4, wherein said mutation is a member selected from the group consisting of one or more mutations that reduce glycosylation of premembrane protein, envelope protein or NS1(1) protein; one or more mutations that reduce cleavage of premembrane protein to membrane protein; one or more substitutions at a site encoding glycine, which site is at position +1 following polyprotein NS1–NS2A cleavage site; one or more deletions comprising at least 30 nucleotides between nucleotide 113 and 384 inclusive, number 1 being a 3'-most nucleotide of a 3'-non-coding end; and one or more mutations in a sequence encoding one or more of eight amino acids at the carboxy terminus cleavage site of NS1.

6. The genetic construct of claim 1, wherein said first flavivirus is a member selected from the group consisting of type 1 dengue virus, type 2 dengue virus, type 3 dengue virus, yellow fever virus, Japanese encephalitis virus, and tick-borne encephalitis virus, and said second flavivirus is type 4 dengue virus.

7. The genetic construct of claim 1, wherein said first flavivirus is a member selected from the group consisting of type 1 dengue virus, type 2 dengue virus, type 3 dengue virus, type 4 dengue virus, yellow fever virus, Japanese encephalitis virus, and tick-borne encephalitis virus, and said second flavivirus is a member selected from the group consisting of type 1 dengue virus, type, 2 dengue virus, and type 3 dengue virus.

8. The genetic construct of claim 1, wherein said first flavivirus is a member selected from the group consisting of type 1 dengue virus, type 2 dengue virus, type 3 dengue virus, type 4 dengue virus, yellow fever virus, Japanese encephalitis virus, and tick-borne encephalitis virus, and said second flavivirus is a member selected from the group consisting of yellow fever virus, Japanese encephalitis virus, and tick-borne encephalitis virus.

9. The genetic construct of claim 1, wherein said region of nucleic acid encoding structural protein recodes premembrane protein and enevlope protein of tick-borne encephalitis virus, and further comprising a region of nucleic acid encoding capsid protein from said second flavivirus.

10. The genetic construct of claim 9, wherein said second flavivirus is a dengue virus.

11. The genetic construct of claim 1, wherein said region of nucleic acid encoding structural protein encodes premembrane protein and envelope protein of Japanese encephalitis virus, and further comprising a region of nucleic acid encoding capsid protein from said second flavivirus.

12. The genetic construct of claim 11, wherein said second flavivirus is a dengue virus.

13. A method of inducing an immune response in a host against a first flavivirus comprising:
(a) preparing the genetic construct of any of claims 1–12, wherein said genetic construct comprises DNA;
(b) generating infectious RNA transcripts from said DNA construct;
(c) introducing said RNA transcripts into a cell;
(d) expressing said RNA transcripts in said cell to produce virus;
(e) harvesting said virus from said cell;
(f) testing said virus in an animal model; and
(g) inoculating said host with virus produced by repeating steps (a)–(e).

14. The genetic construct of claim 1, comprising DNA.

15. A chimeric virus having a genome comprising:
a full genome-length nucleic acid clone of a flavivirus genome having a region of nucleic acid encoding structural protein of a first flavivirus linked to a region of nucleic acid encoding non-structural protein of a second flavivirus, wherein said second flavivirus is a different flavivirus from said first flavivirus, and wherein said flavivirus is defined as an approximately 11 -kilobase positive strand RNA virus having a genome that codes in one open reading frame for three structural proteins, capsid (C), premembrane (preM) and envelope (E), followed by seven non-structural proteins, NS1, NS2A, NS2B, NS3, NS4A, NS4B and NS5.

16. The chimeric virus of claim 15, wherein said second flavivirus is a dengue virus.

17. The chimeric virus of claim 16, wherein said first flavivirus is a member selected from the group consisting of dengue type 1 virus, dengue type 2 virus, and dengue type 3 virus, and said second flavivirus is dengue type 4 virus.

18. The chimeric virus of claim 15 further comprising at least one mutation that is introduced into the viral genome.

19. The chimeric virus of claim 18, wherein said mutation is a member selected from the group consisting of one or more mutations that reduce glycosylation of premembrane protein, envelope protein or NS1(1) protein; one or more mutations that reduce cleavage of premembrane protein to membrane protein; one or more substitutions at a site encoding glycine, which site is at position +1 following polyprotein NS1–NS2A cleavage site; one or more deletions comprising at least 30 nucleotides between nucleotide 113 and 384 inclusive, number 1 being a 3'-most nucleotide of a 3'-non-coding end; and one or more mutations in a sequence encoding one or more of eight amino acids at the carboxy terminus cleavage site of NS1.

20. The chimeric virus of claim 15, wherein said first flavivirus is a member selected from the group consisting of type 1 dengue virus, type 2 dengue virus, type 3 dengue virus, yellow fever virus, Japanese encephalitis virus, and tick-borne encephalitis virus, and said second flavivirus is type 4 dengue virus.

21. The chimeric virus of claim 15, wherein said first flavivirus is a member selected from the group consisting of type 1 dengue virus, type 2 dengue virus, type 3 dengue virus, type 4 dengue virus, yellow fever virus, Japanese encephalitis virus, and tick-borne encephalitis virus, and said second flavivirus is a member selected from the group consisting of type 1 dengue virus, type 2 dengue virus, and type 3 dengue virus.

22. The chimeric virus of claim 15, wherein said first flavivirus is a member selected from the group consisting of type 1 dengue virus, type 2 dengue virus, type 3 dengue virus, type 4 dengue virus, yellow fever virus, Japanese encephalitis virus, and tick-borne encephalitis virus, and said second flavivirus is a member selected from the group consisting of yellow fever virus, Japanese encephalitis virus, and tick-borne encephalitis virus.

23. The chimeric virus of claim 15, wherein said region of nucleic acid encoding structural protein encodes premembrane protein and envelope protein of tick-bome encephalitis virus, and further comprising a region of nucleic acid encoding capsid protein from said second flavivirus.

24. The chimeric virus of claim 23, wherein said second

25. The chimeric virus of claim 15, wherein said region of nucleic acid encoding structural protein encodes premembrane protein and envelope protein of Japanese encephalitis virus, and further comprising a region of nucleic acid encoding capsid protein from said second flavivirus.

26. The chimeric virus of claim 25, wherein said second flavivirus is a dengue virus.

27. An immunogenic composition against a first flavivrus comprising the chimeric virus of any of claims 15–26 and a pharmaceutically acceptable carrier.

28. An isolated recombinant DNA construct that encodes stable, full-length infectious dengue type 4 viral RNA.

29. The DNA construct of claim 28, further comprising a vector.

30. The DNA construct of claim 29, wherein said vector is a plasmid.

31. A host cell stably transformed with the DNA construct of claim 29, in a manner allowing expression of said DNA construct.

32. The host cell of claim 31, wherein said host cell is a prokaryotic cell.

33. The DNA construct of claim 28, further comprising at least one mutation that is introduced into the viral genome.

34. The DNA construct of claim 33, wherein said mutation is a member selected from the group consisting of one or more mutations that reduce glycosylation of premembrane protein, envelope protein or NS1(1) protein; one or more mutations that reduce cleavage of premembrane protein to membrane protein; one or more substitutions at a site encoding glycine, which site is at position +1 following polyprotein NS1–NS2A cleavage site; one or more deletions comprising at least 30 nucleotides between nucleotide 113 and 384 inclusive, number 1 being a 3'-most nucleotide of a 3'-non-coding end; and one or more mutations in a sequence encoding one or more of eight amino acids at the carboxy terminus cleavage site of NS1.

35. An immunogenic composition against dengue type 4 virus comprising a dengue type 4 virus, having a stable, full-length infectious dengue type 4 viral genome comprising at least one mutation that is introduced into the viral genome, and a pharmaceutically acceptable carrier.

36. The immunogenic composition of claim 35, wherein said mutation is a member selected from the group consisting of one or more mutations that reduce glycosylation of premembrane protein, envelope protein or NS1(1) protein; one or more mutations that reduce cleavage of premembrane protein to membrane protein; one or more substitutions at a site encoding glycine, which site is at position +1 following polyprotein NS1–NS2A cleavage site; one or more deletions comprising at least 30 nucleotides between nucleotide 113 and 384 inclusive, number 1 being a 3'-most nucleotide of a 3'-non-coding end; and one or more mutations in a sequence encoding one or more of eight amino acids at the carboxy terminus cleavage site of NS1.

37. An isolated RNA segment comprising stable, full-length infectious dengue type 4 viral genome transcribed from a recombinant DNA construct.

38. The RNA segment of claim 37, further comprising at least one mutation that is introduced into the viral genome.

39. The RNA segment of claim 38, wherein said mutation is a member selected from the group consisting of one or more mutations that reduce glycosylation of premembrane protein, envelope protein or NS1(1) protein; one or more mutations that reduce cleavage of premembrane protein to membrane protein; one or more substitutions at a site encoding glycine, which site is at position +1 following polyprotein NS1–NS2A cleavage site; one or more deletions comprising at least 30 nucleotides between nucleotide 113 and 384 inclusive, number 1 being a 3'-most nucleotide of a 3'-non-coding end; and one or more mutations in a sequence encoding one or more of eight amino acids at the carboxy terminus cleavage site of NS1.

40. A baculovirus, comprising:
a 4.0 kilobase recombinant dengue cDNA sequence that encodes dengue virus capsid protein, pre-matrix protein, envelope glycoprotein, and NS1 and NS2a nonstructural proteins.

41. An immunogenic composition consisting essentially of dengue type 4 virus envelope glycoprotein and NS1 nonstructural protein.

42. An immunogenic composition consisting essentially of dengue type 4 virus capsid protein, pre-matrix protein, envelope glycoprotein and NS1 nonstructural protein.

43. A baculovirus comprising the dengue cDNA coding sequence for: (1) only dengue envelope glycoprotein or (2) only dengue non-structural proteins NS1 and NS2a.

44. An immunogenic composition consisting essentially of:
a pharmaceutically acceptable carrier; and
an amount of dengue type 4 virus proteins effective to induce a dengue type 4 virus specific immunological response.

45. The composition of claim 44, wherein said dengue type 4 virus proteins are a member selected from the group consisting of dengue type 4 virus capsid protein, pre-matrix protein, envelope glycoprotein, NS1 nonstructural protein, NS2a nonstructural protein, and mixtures of these.

46. A method for producing an immunogenic composition, comprising:
culturing cells infected with a baculovirus comprising a nucleotide sequence encoding at least one dengue type 4 virus protein under conditions such that said dengue type 4 virus protein is produced;
separating said dengue type 4 virus protein from said cells; and
formulating said separated dengue type 4 virus protein in a therapeutically effective concentration with a pharmaceutically effective carrier.

47. The method of claim 46, wherein said dengue type 4 virus protein is a member selected from the group consisting of dengue type 4 virus capsid protein, pre-matrix protein, envelope glycoprotein, NS1 nonstructural protein, NS2a nonstructural protein, and mixtures of these.

48. The method of claim 46, wherein said infected cells are *Spodoptera frugiperda* cells.

49. A baculovirus comprising the Japanese B encephalitis virus cDNA coding sequence for the 3 structural proteins (C-M-E) and non-structural proteins NS1 and NS2a.

50. A method for producing an immunogenic composition, comprising:
culturing a recombinant baculovirus in infected cells to express Japanese B encephalitis protein;
separating said Japanese B encephalitis protein; and
formulating said Japanese B encephalitis protein in a therapeutically effective concentration with a pharmaceutically effective carrier.

51. The method of claim 50, wherein said Japanese B encephalitis protein is a member selected from the group consisting of Japanese B encephalitis capsid protein, pre-matrix protein, envelop glycoprotein, NS1 nonstructural protein, NS2a nonstructural protein, and mixtures of these.

52. The method of claim 50, where said infected cells are *Spodoptera frugiperda* cells.

* * * * *

UNITED STATES PATENT AND TRADEMARK OFFICE
CERTIFICATE OF CORRECTION

PATENT NO. : 6,184,024 B1
DATED : February 6, 2001
INVENTOR(S) : Ching-Juh Lai, Michael Bray, Alexander G. Pletnev, Ruhe Men, Yi-Ming Zhang, Kenneth H. Eckels, and Robert Chanock It is certified that error appears in the above-identified patent and that said Letters Patent is hereby corrected as shown below:

Column 65, claim 9,
Line 46, please replace "protein recodes" with "protein encodes."

Column 66, claim 23,
Line 63, please replace tick-bome" with "tick-borne."

Signed and Sealed this

Thirteenth Day of November, 2001

Attest:

NICHOLAS P. GODICI
Attesting Officer
Acting Director of the United States Patent and Trademark Office